(12) United States Patent
Wilson et al.

(10) Patent No.: US 10,130,581 B2
(45) Date of Patent: *Nov. 20, 2018

(54) METHOD FOR IMPROVING THE PHARMACEUTIC PROPERTIES OF MICROPARTICLES COMPRISING DIKETOPIPERAZINE AND AN ACTIVE AGENT

(71) Applicant: MannKind Corporation, Valencia, CA (US)

(72) Inventors: Bryan R. Wilson, Brewster, NY (US); Marshall Grant, Newtown, CT (US)

(73) Assignee: MannKind Corporation, Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/971,785

(22) Filed: Dec. 16, 2015

(65) Prior Publication Data

US 2016/0101049 A1    Apr. 14, 2016

Related U.S. Application Data

(63) Continuation of application No. 13/942,482, filed on Jul. 15, 2013, now Pat. No. 9,241,903, which is a continuation of application No. 13/239,696, filed on Sep. 22, 2011, now Pat. No. 8,512,932, which is a continuation of application No. 11/678,046, filed on Feb. 22, 2007, now Pat. No. 8,039,431.

(60) Provisional application No. 60/776,605, filed on Feb. 22, 2006.

(51) Int. Cl.
| | |
|---|---|
| *A61K 9/00* | (2006.01) |
| *A61K 9/14* | (2006.01) |
| *A61K 9/16* | (2006.01) |
| *A61K 38/28* | (2006.01) |

(52) U.S. Cl.
CPC ............ *A61K 9/0075* (2013.01); *A61K 9/145* (2013.01); *A61K 9/1617* (2013.01); *A61K 9/1694* (2013.01); *A61K 38/28* (2013.01)

(58) Field of Classification Search
None
See application file for complete search history.

(56) References Cited

U.S. PATENT DOCUMENTS

| | | |
|---|---|---|
| 2,549,303 A | 4/1951 | Friden |
| 2,754,276 A | 7/1956 | Joseph et al. |
| D189,076 S | 10/1960 | Altman |
| 3,337,740 A | 8/1967 | Gray et al. |
| 3,407,203 A | 10/1968 | Buijle |
| 3,518,340 A | 6/1970 | Raper |
| 3,622,053 A | 11/1971 | Ryden |
| 3,673,698 A | 7/1972 | Guerard |
| 3,669,113 A | 8/1972 | Altounyan et al. |
| 3,823,816 A | 7/1974 | Controullis et al. |
| 3,823,843 A | 7/1974 | Stephens et al. |
| 3,856,142 A | 12/1974 | Vessalo |
| 3,873,651 A | 3/1975 | Mosley, Jr. et al. |
| 3,906,950 A | 9/1975 | Cocozza |
| 3,921,637 A | 11/1975 | Bennie et al. |
| 3,976,773 A | 8/1976 | Curran et al. |
| 3,980,074 A | 9/1976 | Watt et al. |
| 3,998,226 A | 12/1976 | Harris |
| 4,013,075 A | 3/1977 | Cocozza |
| 4,018,619 A | 4/1977 | Webster et al. |
| 4,022,749 A | 5/1977 | Kuechler |
| 4,040,536 A | 8/1977 | Schwarz |
| 4,047,525 A | 9/1977 | Kulessa et al. |
| 4,066,756 A | 1/1978 | Orr et al. |
| 4,078,128 A | 3/1978 | Hoyt et al. |
| 4,091,077 A | 5/1978 | Smith et al. |
| 4,098,273 A | 7/1978 | Glenn |
| 4,102,953 A | 7/1978 | Johnson et al. |
| 4,110,240 A | 8/1978 | Leo et al. |
| 4,148,308 A | 4/1979 | Sayer |
| 4,153,689 A | 5/1979 | Hirai |
| D252,707 S | 8/1979 | Besnard |
| 4,168,002 A | 9/1979 | Crosby |
| 4,171,000 A | 10/1979 | Uhle |
| 4,175,556 A | 11/1979 | Freezer |
| 4,187,129 A | 2/1980 | Bost et al. |
| 4,196,196 A | 4/1980 | Tiholiz |

(Continued)

FOREIGN PATENT DOCUMENTS

| | | |
|---|---|---|
| CA | 2536047 A1 | 3/2005 |
| CA | 2551182 C | 8/2010 |

(Continued)

OTHER PUBLICATIONS

Website: http://medical-dictionary.thefreedictionary.com/medicament, retrieved on Mar. 20, 2015, 1 page.*
Wilson, et al., at http://www.aapsj.org/abstracts/AM_2004/AAPS2004-002724.PDF.*
Amodeo et al., Pain peptides. Solution structure of orphanin FQ2. FEBS Letters, vol. 473, Issue 2, pp. 157-160 (2000).
Vanderah et al., FE200041 (D-Phe-D-Phe-D-Nle-D-Arg-NH2): A peripheral efficacious k opioid agonist with unprecedented selectivity. The Journal of Pharmacology and Experimental Therapeutics, vol. 310, No. 1, pp. 326-333 (2004).

(Continued)

*Primary Examiner* — Satyanarayana R Gudibande
(74) *Attorney, Agent, or Firm* — K&L Gates LLP; Louis C. Cullman; Hal Gibson

(57) ABSTRACT

Methods are provided for drying a particle. Specifically, there is provided a spray-dried diketopiperazine-insulin particle formulation having improved aerodynamic performance and in which the active agent is more stabile and efficiently delivered as compared to that of the lyophilized diketopiperazine-insulin formulation. The dry powders have utility as pharmaceutical formulations for pulmonary delivery.

14 Claims, 17 Drawing Sheets

(56) References Cited

U.S. PATENT DOCUMENTS

| | | | |
|---|---|---|---|
| 4,206,758 | A | 6/1980 | Hallworth et al. |
| 4,210,140 | A | 7/1980 | James et al. |
| 4,211,769 | A | 7/1980 | Okada |
| 4,268,460 | A | 5/1981 | Boiarski et al. |
| 4,272,398 | A | 6/1981 | Jaffe |
| 4,275,820 | A | 6/1981 | LeBlond |
| 4,289,759 | A | 9/1981 | Heavener |
| 4,294,829 | A | 10/1981 | Suzuki |
| 4,300,546 | A | 11/1981 | Kruber |
| 4,356,167 | A | 10/1982 | Kelly |
| D269,463 | S | 6/1983 | Young et al. |
| 4,407,525 | A | 10/1983 | Hoppe |
| 4,456,007 | A | 6/1984 | Nakao et al. |
| 4,481,139 | A | 11/1984 | Folkers et al. |
| 4,483,922 | A | 11/1984 | Carpenter |
| D276,654 | S | 12/1984 | Snellman-Wasenius et al. |
| 4,487,327 | A | 12/1984 | Grayson |
| 4,524,769 | A | 6/1985 | Wetterlin |
| 4,526,804 | A | 7/1985 | Escallon |
| 4,534,345 | A | 8/1985 | Wetterlin |
| D282,209 | S | 1/1986 | Newell et al. |
| 4,581,020 | A | 4/1986 | Mittleman |
| 4,592,348 | A | 6/1986 | Waters, IV et al. |
| 4,613,500 | A | 9/1986 | Suzuki |
| 4,615,817 | A | 10/1986 | McCoy |
| 4,624,861 | A | 11/1986 | Yale et al. |
| 4,637,996 | A | 1/1987 | Konishi |
| D288,852 | S | 3/1987 | Miyoshi |
| 4,659,696 | A | 4/1987 | Hirai et al. |
| 4,668,218 | A | 5/1987 | Virtanen |
| 4,671,954 | A | 6/1987 | Goldberg et al. |
| 4,681,752 | A | 7/1987 | Melillo |
| D295,321 | S | 4/1988 | Hallworth |
| 4,742,156 | A | 5/1988 | Wright |
| 4,757,066 | A | 7/1988 | Shiokari et al. |
| 4,792,451 | A | 12/1988 | Kim |
| 4,811,731 | A | 3/1989 | Newell et al. |
| D301,273 | S | 5/1989 | Leonard |
| 4,835,312 | A | 5/1989 | Itoh et al. |
| 4,841,964 | A | 6/1989 | Hurka et al. |
| 4,847,091 | A | 7/1989 | Illum |
| 4,849,227 | A | 7/1989 | Cho |
| 4,861,627 | A | 8/1989 | Mathiowitz |
| 4,866,051 | A | 9/1989 | Hunt et al. |
| 4,873,087 | A | 10/1989 | Morishita et al. |
| 4,887,722 | A | 12/1989 | Greenward, Sr. |
| 4,900,730 | A | 2/1990 | Miyauchi |
| 4,907,583 | A | 3/1990 | Wetterlin et al. |
| 4,925,673 | A | 5/1990 | Steiner |
| 4,926,852 | A | 5/1990 | Zoltan et al. |
| 4,927,555 | A | 5/1990 | Colarusso, Jr. |
| 4,927,928 | A | 5/1990 | Shroot et al. |
| 4,946,828 | A | 8/1990 | Markussen |
| 4,981,295 | A | 1/1991 | Belman et al. |
| 4,981,625 | A | 1/1991 | Rhim et al. |
| 4,983,402 | A | 1/1991 | Steiner et al. |
| 4,984,158 | A | 1/1991 | Hillsman |
| 4,991,605 | A | 2/1991 | Keritsis |
| 4,998,624 | A | 3/1991 | Capes et al. |
| 5,006,343 | A | 4/1991 | Benson |
| D316,902 | S | 5/1991 | Hoefling |
| 5,017,383 | A | 5/1991 | Ozawa et al. |
| 5,019,400 | A | 5/1991 | Gombotz et al. |
| 5,021,376 | A | 6/1991 | Nienburg et al. |
| 5,027,806 | A | 7/1991 | Zoltan et al. |
| 5,042,975 | A | 8/1991 | Chien |
| D321,570 | S | 11/1991 | Blasdell et al. |
| 5,067,500 | A | 11/1991 | Keritsis |
| 5,069,204 | A | 12/1991 | Smith et al. |
| 5,074,418 | A | 12/1991 | Buan et al. |
| 5,075,027 | A | 12/1991 | Dixit et al. |
| 5,098,590 | A | 3/1992 | Dixit et al. |
| 5,105,291 | A | 4/1992 | Matsumoto et al. |
| D326,517 | S | 5/1992 | Funai et al. |
| 5,110,007 | A | 5/1992 | Law et al. |
| 5,110,823 | A | 5/1992 | Hamaguchi et al. |
| 5,118,666 | A | 6/1992 | Habener |
| 5,120,712 | A | 6/1992 | Habener |
| 5,124,291 | A | 6/1992 | Bremer et al. |
| 5,131,539 | A | 7/1992 | Karita et al. |
| 5,139,878 | A | 8/1992 | Kim |
| 5,145,684 | A | 9/1992 | Liversidge et al. |
| 5,152,284 | A | 10/1992 | Valentini et al. |
| D331,106 | S | 11/1992 | Fuchs |
| 5,167,506 | A | 12/1992 | Kilis et al. |
| 5,170,801 | A | 12/1992 | Casper et al. |
| 5,188,837 | A | 2/1993 | Domb |
| 5,196,049 | A | 3/1993 | Coombs et al. |
| 5,201,308 | A | 4/1993 | Newhouse |
| 5,203,768 | A | 4/1993 | Haak et al. |
| 5,204,108 | A | 4/1993 | Ilium |
| 5,208,998 | A | 5/1993 | Dyler, Jr. |
| 5,215,739 | A | 6/1993 | Kamishita et al. |
| D337,636 | S | 7/1993 | Kocinski |
| D338,062 | S | 8/1993 | Yair |
| D338,268 | S | 8/1993 | Kobayashi et al. |
| 5,239,992 | A | 8/1993 | Bougamont et al. |
| 5,239,993 | A | 8/1993 | Evans |
| 5,244,653 | A | 9/1993 | Berke et al. |
| 5,250,287 | A | 10/1993 | Cocozza |
| D340,975 | S | 11/1993 | Sladek |
| 5,260,306 | A | 11/1993 | Boardman et al. |
| 5,270,305 | A | 12/1993 | Palmer |
| 5,287,850 | A | 2/1994 | Haber et al. |
| D344,796 | S | 3/1994 | Sochon et al. |
| D344,797 | S | 3/1994 | Sochon et al. |
| D345,013 | S | 3/1994 | Huck et al. |
| 5,301,666 | A | 4/1994 | Lerk et al. |
| 5,306,453 | A | 4/1994 | Shulman |
| D347,057 | S | 5/1994 | Yair |
| D348,100 | S | 6/1994 | Clarke |
| 5,320,094 | A | 6/1994 | Laube et al. |
| D348,928 | S | 7/1994 | Ashley et al. |
| D348,929 | S | 7/1994 | Paton |
| 5,327,883 | A | 7/1994 | Williams et al. |
| 5,328,464 | A | 7/1994 | Kriesel et al. |
| 5,331,953 | A | 7/1994 | Andersson et al. |
| 5,333,106 | A | 7/1994 | Lanpher et al. |
| D349,572 | S | 8/1994 | Jagnandan et al. |
| D350,193 | S | 8/1994 | Huck et al. |
| 5,337,740 | A | 8/1994 | Armstrong et al. |
| D350,602 | S | 9/1994 | Hobbs et al. |
| D350,821 | S | 9/1994 | Wright et al. |
| 5,351,683 | A | 10/1994 | Chiesi et al. |
| 5,352,461 | A | 10/1994 | Feldstein et al. |
| 5,354,562 | A | 10/1994 | Platz |
| 5,358,734 | A | 10/1994 | Lenox et al. |
| D352,107 | S | 11/1994 | Meier et al. |
| 5,360,614 | A | 11/1994 | Fox et al. |
| 5,363,842 | A | 11/1994 | Mishelevich et al. |
| 5,364,838 | A | 11/1994 | Rubsamen |
| 5,372,128 | A | 12/1994 | Haber et al. |
| D355,029 | S | 1/1995 | Kinneir et al. |
| 5,385,904 | A | 1/1995 | Andersson et al. |
| 5,394,868 | A | 3/1995 | Ambrosio et al. |
| 5,401,516 | A | 3/1995 | Milstein et al. |
| D357,603 | S | 4/1995 | Wolff |
| 5,404,871 | A | 4/1995 | Goodman et al. |
| D358,880 | S | 5/1995 | Mulhauser et al. |
| 5,413,804 | A | 5/1995 | Rhodes |
| 5,415,162 | A | 5/1995 | Casper et al. |
| D359,153 | S | 6/1995 | Viggiano |
| D359,555 | S | 6/1995 | Funai et al. |
| 5,424,286 | A | 6/1995 | Eng |
| 5,437,271 | A | 8/1995 | Hodson et al. |
| 5,443,841 | A | 8/1995 | Milstein et al. |
| D362,500 | S | 9/1995 | Cook et al. |
| 5,447,150 | A | 9/1995 | Bacon |
| 5,447,151 | A | 9/1995 | Bruna et al. |
| 5,447,728 | A | 9/1995 | Milstein et al. |
| 5,451,410 | A | 9/1995 | Milstein et al. |
| D363,775 | S | 10/1995 | Hobbs |
| 5,454,871 | A | 10/1995 | Liaw et al. |
| 5,455,335 | A | 10/1995 | Kahne et al. |

(56) References Cited

U.S. PATENT DOCUMENTS

| | | |
|---|---|---|
| 5,458,135 A | 10/1995 | Patton et al. |
| 5,469,750 A | 11/1995 | Lloyd et al. |
| 5,469,971 A | 11/1995 | Chilton et al. |
| 5,476,093 A | 12/1995 | Laniken |
| 5,477,285 A | 12/1995 | Riddle et al. |
| D365,876 S | 1/1996 | Chawla |
| 5,482,032 A | 1/1996 | Smith et al. |
| 5,482,927 A | 1/1996 | Maniar et al. |
| 5,483,954 A | 1/1996 | Mecikalski |
| 5,484,606 A | 1/1996 | Dhaber et al. |
| 5,487,378 A | 1/1996 | Robertson et al. |
| 5,492,112 A | 2/1996 | Mecikalski et al. |
| D368,364 S | 4/1996 | Reitano et al. |
| 5,503,144 A | 4/1996 | Bacon |
| 5,503,852 A | 4/1996 | Steiner et al. |
| 5,505,194 A | 4/1996 | Adjei et al. |
| 5,506,203 A | 4/1996 | Backstorm et al. |
| D370,255 S | 5/1996 | Yamamoto et al. |
| 5,514,646 A | 5/1996 | Chance et al. |
| 5,518,998 A | 5/1996 | Backstorm et al. |
| 5,524,613 A | 6/1996 | Haber et al. |
| 5,532,461 A | 7/1996 | Crummenauer et al. |
| 5,533,502 A | 7/1996 | Piper |
| 5,533,505 A | 7/1996 | Kallstrand et al. |
| 5,541,155 A | 7/1996 | Leone-Bay |
| 5,542,411 A | 8/1996 | Rex |
| 5,542,539 A | 8/1996 | Early |
| 5,545,618 A | 8/1996 | Buckley et al. |
| 5,547,929 A | 8/1996 | Anderson, Jr. et al. |
| 5,562,909 A | 10/1996 | Allcock et al. |
| 5,562,918 A | 10/1996 | Stimpson |
| 5,568,884 A | 10/1996 | Bruna |
| 5,570,810 A | 11/1996 | Lambelet, Jr. et al. |
| 5,571,795 A | 11/1996 | Kahne et al. |
| 5,574,008 A | 11/1996 | Johnson et al. |
| 5,577,497 A | 11/1996 | Mecikalski et al. |
| 5,578,323 A | 11/1996 | Milstein et al. |
| 5,584,417 A | 12/1996 | Graf et al. |
| D377,215 S | 1/1997 | Rand |
| D377,686 S | 1/1997 | Waldeck et al. |
| 5,595,175 A | 1/1997 | Malcher et al. |
| 5,596,701 A | 1/1997 | Augusteijn et al. |
| D377,861 S | 2/1997 | Jacober |
| 5,598,835 A | 2/1997 | von Schrader |
| 5,601,846 A | 2/1997 | Milstein et al. |
| 5,610,271 A | 3/1997 | Dooley et al. |
| 5,614,492 A | 3/1997 | Habener |
| 5,615,670 A | 4/1997 | Rhodes et al. |
| 5,617,844 A | 4/1997 | King |
| 5,619,984 A | 4/1997 | Hodson et al. |
| 5,622,164 A | 4/1997 | Kilis et al. |
| 5,622,166 A | 4/1997 | Eisele et al. |
| 5,623,724 A | 4/1997 | Gurkovich et al. |
| 5,623,920 A | 4/1997 | Bryant |
| D379,506 S | 5/1997 | Maher |
| 5,629,020 A | 5/1997 | Leone-Bay |
| 5,631,224 A | 5/1997 | Efendic et al. |
| 5,632,971 A | 5/1997 | Yang |
| 5,634,900 A | 6/1997 | Makino et al. |
| 5,639,441 A | 6/1997 | Sievers et al. |
| 5,641,861 A | 6/1997 | Dooley et al. |
| D381,416 S | 7/1997 | Hansson et al. |
| 5,642,727 A | 7/1997 | Datta et al. |
| 5,642,728 A | 7/1997 | Andersson et al. |
| 5,643,957 A | 7/1997 | Leone-Bay et al. |
| 5,645,051 A | 7/1997 | Schultz |
| 5,651,359 A | 7/1997 | Bougamont et al. |
| 5,653,961 A | 8/1997 | McNally et al. |
| 5,655,516 A | 8/1997 | Goodman et al. |
| 5,655,523 A | 8/1997 | Hodson et al. |
| 5,657,748 A | 8/1997 | Braithwaite |
| 5,658,878 A | 8/1997 | Backstrom et al. |
| 5,660,169 A | 8/1997 | Kallstrand et al. |
| 5,672,581 A | 9/1997 | Rubsamen et al. |
| 5,673,686 A | 10/1997 | Villax et al. |
| 5,679,377 A | 10/1997 | Bernstein et al. |
| 5,687,710 A | 11/1997 | Ambrosio et al. |
| 5,690,910 A | 11/1997 | Ahmed et al. |
| 5,693,338 A | 12/1997 | Milstein |
| 5,699,789 A | 12/1997 | Hendricks |
| D389,238 S | 1/1998 | Kirk, III et al. |
| D389,570 S | 1/1998 | Savolainen |
| 5,705,483 A | 1/1998 | Galloway et al. |
| D390,651 S | 2/1998 | Smith et al. |
| D390,653 S | 2/1998 | Blasdell et al. |
| 5,714,007 A | 2/1998 | Pletcher et al. |
| 5,714,167 A | 2/1998 | Milstein et al. |
| 5,715,811 A | 2/1998 | Ohki et al. |
| 5,727,333 A | 3/1998 | Folan |
| 5,727,546 A | 3/1998 | Clarke et al. |
| 5,740,793 A | 4/1998 | Hodson et al. |
| 5,740,794 A | 4/1998 | Smith et al. |
| 5,746,197 A | 5/1998 | Williams |
| 5,746,227 A | 5/1998 | Rose et al. |
| 5,747,445 A | 5/1998 | Backstrom et al. |
| 5,752,505 A | 5/1998 | Ohki et al. |
| 5,755,218 A | 5/1998 | Johansson et al. |
| D395,147 S | 6/1998 | Vidgren et al. |
| D395,499 S | 6/1998 | Eisele et al. |
| 5,758,638 A | 6/1998 | Kreamer |
| 5,763,396 A | 6/1998 | Weiner et al. |
| 5,766,620 A | 6/1998 | Heiber et al. |
| 5,766,633 A | 6/1998 | Milstein et al. |
| 5,769,073 A | 6/1998 | Eason et al. |
| 5,772,085 A | 6/1998 | Bryant et al. |
| RE35,862 E | 7/1998 | Steiner et al. |
| 5,775,320 A | 7/1998 | Patton et al. |
| 5,785,049 A | 7/1998 | Smith et al. |
| 5,785,989 A | 7/1998 | Stanley et al. |
| D397,435 S | 8/1998 | Naumann |
| 5,792,451 A | 8/1998 | Sarubbi et al. |
| 5,794,613 A | 8/1998 | Piskorski |
| 5,797,391 A | 8/1998 | Cook et al. |
| D398,992 S | 9/1998 | Feret |
| 5,799,821 A | 9/1998 | Lambelet, Jr. et al. |
| 5,807,315 A | 9/1998 | Va Antwerp et al. |
| 5,809,997 A | 9/1998 | Wolf |
| 5,811,127 A | 9/1998 | Milstein et al. |
| 5,813,397 A | 9/1998 | Goodman et al. |
| 5,817,343 A | 10/1998 | Burke |
| 5,824,345 A | 10/1998 | Milstein et al. |
| 5,839,429 A | 11/1998 | Marnfeldt et al. |
| 5,840,279 A | 11/1998 | Narodylo et al. |
| 5,840,340 A | 11/1998 | Milstein et al. |
| 5,846,447 A | 12/1998 | Beatty |
| 5,848,589 A | 12/1998 | Welnetz |
| 5,849,322 A | 12/1998 | Ebert et al. |
| 5,857,457 A | 1/1999 | Hyppola |
| 5,858,099 A | 1/1999 | Sun et al. |
| 5,865,012 A | 2/1999 | Hansson et al. |
| 5,868,774 A | 2/1999 | Reil |
| 5,874,064 A | 2/1999 | Edwards et al. |
| 5,875,776 A | 3/1999 | Vaghefi |
| 5,877,174 A | 3/1999 | Ono et al. |
| 5,881,719 A | 3/1999 | Gottenauer et al. |
| 5,881,721 A | 3/1999 | Bunce et al. |
| 5,884,620 A | 3/1999 | Gonda et al. |
| 5,888,477 A | 3/1999 | Gonda et al. |
| 5,896,855 A | 4/1999 | Hobbs et al. |
| 5,901,703 A | 5/1999 | Ohki et al. |
| 5,904,139 A | 5/1999 | Hauser |
| D410,541 S | 6/1999 | Moulin |
| D411,005 S | 6/1999 | Coe |
| 5,908,639 A | 6/1999 | Simpkin et al. |
| 5,912,011 A | 6/1999 | Makino et al. |
| 5,918,594 A | 7/1999 | Asking et al. |
| 5,919,897 A | 7/1999 | Dooley et al. |
| 5,921,237 A | 7/1999 | Eisele et al. |
| 5,922,253 A | 7/1999 | Herbert et al. |
| 5,924,419 A | 7/1999 | Kotliar |
| 5,929,027 A | 7/1999 | Takama et al. |
| D412,572 S | 8/1999 | Gray |
| D412,744 S | 8/1999 | Braithwaite |
| D412,978 S | 8/1999 | Cameron |

(56) References Cited

U.S. PATENT DOCUMENTS

| | | |
|---|---|---|
| D412,979 S | 8/1999 | Weinstein et al. |
| 5,934,273 A | 8/1999 | Andersson et al. |
| 5,942,242 A | 8/1999 | Mizushima et al. |
| 5,972,242 A | 8/1999 | Mizushima et al. |
| 5,948,749 A | 9/1999 | Igarashi et al. |
| 5,952,008 A | 9/1999 | Backstrom et al. |
| 5,954,047 A | 9/1999 | Armer et al. |
| 5,965,701 A | 10/1999 | Junien |
| 5,971,951 A | 10/1999 | Ruskewicz |
| D416,085 S | 11/1999 | Forssell et al. |
| D416,621 S | 11/1999 | Forssell et al. |
| D416,998 S | 11/1999 | Hodson et al. |
| D417,271 S | 11/1999 | Denyer et al. |
| 5,975,347 A | 11/1999 | Lambelet, Jr. et al. |
| 5,976,569 A | 11/1999 | Milstein |
| 5,976,574 A | 11/1999 | Gordon |
| 5,977,071 A | 11/1999 | Galloway et al. |
| 5,980,865 A | 11/1999 | Ahmed et al. |
| 5,981,488 A | 11/1999 | Hoffman |
| 5,983,893 A | 11/1999 | Wetterlin |
| 5,985,248 A | 11/1999 | Gordon et al. |
| 5,985,309 A | 11/1999 | Edwards et al. |
| 5,990,077 A | 11/1999 | Drucker |
| D417,732 S | 12/1999 | Dagsland et al. |
| D417,912 S | 12/1999 | Dagsland et al. |
| 5,996,577 A | 12/1999 | Ohki et al. |
| 5,997,848 A | 12/1999 | Patton et al. |
| 6,001,336 A | 12/1999 | Gordon |
| 6,006,747 A | 12/1999 | Eisele et al. |
| 6,006,753 A | 12/1999 | Efendic |
| D418,600 S | 1/2000 | Haerle |
| D420,736 S | 2/2000 | Moulin |
| 6,026,809 A | 2/2000 | Abrams et al. |
| 6,029,663 A | 2/2000 | Eisele et al. |
| D421,800 S | 3/2000 | Doat |
| 6,039,208 A | 3/2000 | Lambelet et al. |
| 6,043,214 A | 3/2000 | Jensen et al. |
| 6,045,828 A | 4/2000 | Bystorm et al. |
| 6,051,256 A | 4/2000 | Platz et al. |
| 6,051,551 A | 4/2000 | Hughes et al. |
| 6,055,980 A | 5/2000 | Mecikalski et al. |
| 6,056,169 A | 5/2000 | Bruna et al. |
| 6,060,069 A | 5/2000 | Hill et al. |
| 6,063,910 A | 5/2000 | Debenedetti et al. |
| 6,071,497 A | 6/2000 | Steiner et al. |
| 6,073,629 A | 6/2000 | Hardy et al. |
| 6,076,521 A | 6/2000 | Lindahl et al. |
| 6,077,543 A | 6/2000 | Gordon et al. |
| 6,080,762 A | 6/2000 | Allen et al. |
| 6,085,745 A | 6/2000 | Levander et al. |
| D428,486 S | 7/2000 | Schuckmann |
| 6,087,334 A | 7/2000 | Beeley et al. |
| 6,087,351 A | 7/2000 | Nye |
| 6,089,228 A | 7/2000 | Smith et al. |
| 6,095,136 A | 8/2000 | Virtanen |
| 6,098,618 A | 8/2000 | Jennings et al. |
| 6,098,619 A | 8/2000 | Britto et al. |
| 6,102,035 A | 8/2000 | Asking et al. |
| 6,105,571 A | 8/2000 | Coffee |
| 6,105,574 A | 8/2000 | Jahnsson |
| 6,109,261 A | 8/2000 | Clarke et al. |
| 6,109,481 A | 8/2000 | Alexander et al. |
| 6,099,517 A | 9/2000 | Daughtery |
| 6,116,237 A | 9/2000 | Schultz |
| 6,116,238 A | 9/2000 | Jackson et al. |
| 6,116,239 A | 9/2000 | Volgyesi |
| 6,119,684 A | 9/2000 | Nohl et al. |
| 6,119,688 A | 9/2000 | Whaley et al. |
| 6,131,567 A | 10/2000 | Gonda et al. |
| 6,132,766 A | 10/2000 | Sankaram et al. |
| 6,133,235 A | 10/2000 | Galloway et al. |
| 6,142,145 A | 11/2000 | Dagsland |
| 6,152,130 A | 11/2000 | Abrams |
| 6,153,613 A | 11/2000 | Ono et al. |
| 6,155,423 A | 12/2000 | Katzne et al. |
| 6,156,114 A | 12/2000 | Bell et al. |
| 6,158,431 A | 12/2000 | Poole |
| 6,159,360 A | 12/2000 | Gerteis et al. |
| RE37,053 E | 2/2001 | Hanes et al. |
| 6,182,655 B1 | 2/2001 | Keller et al. |
| 6,187,291 B1 | 2/2001 | Weinstein et al. |
| 6,191,102 B1 | 2/2001 | DiMarchi et al. |
| 6,192,876 B1 | 2/2001 | Denyer et al. |
| 6,193,844 B1 | 2/2001 | McLaughlin et al. |
| 6,193,957 B1 | 2/2001 | Ahmed |
| D438,612 S | 3/2001 | Suh |
| D439,325 S | 3/2001 | Frost |
| D439,656 S | 3/2001 | Andersson et al. |
| 6,198,847 B1 | 3/2001 | Washizawa |
| D441,446 S | 5/2001 | Dagsland et al. |
| D441,859 S | 5/2001 | Pera |
| D442,685 S | 5/2001 | Sladek |
| 6,235,725 B1 | 5/2001 | Ahmed |
| D444,226 S | 6/2001 | Geert-Jensen et al. |
| 6,250,300 B1 | 6/2001 | Andersson et al. |
| 6,254,854 B1 | 7/2001 | Edwards et al. |
| 6,257,232 B1 | 7/2001 | Andersson et al. |
| 6,258,816 B1 | 7/2001 | Singh et al. |
| 6,263,871 B1 | 7/2001 | Brown et al. |
| 6,269,952 B1 | 8/2001 | Watt et al. |
| 6,273,084 B1 | 8/2001 | Frid |
| 6,273,085 B1 | 8/2001 | Eisele et al. |
| 6,273,086 B1 | 8/2001 | Ohki et al. |
| 6,277,819 B1 | 8/2001 | Efendic |
| 6,279,511 B1 | 8/2001 | Loughnane |
| D448,076 S | 9/2001 | von Schuckmann |
| 6,286,506 B1 | 9/2001 | MacAndrew et al. |
| 6,286,507 B1 | 9/2001 | Jahnsson |
| 6,294,204 B1 | 9/2001 | Rossling et al. |
| D449,684 S | 10/2001 | Christup et al. |
| 6,298,846 B1 | 10/2001 | Ohki et al. |
| 6,298,847 B1 | 10/2001 | Datta et al. |
| D450,117 S | 11/2001 | Braithwaite et al. |
| D451,597 S | 12/2001 | Suh |
| 6,328,034 B1 | 12/2001 | Eisele et al. |
| 6,331,318 B1 | 12/2001 | Milstein |
| D452,910 S | 1/2002 | Braithwaite et al. |
| 6,335,316 B1 | 1/2002 | Hughes et al. |
| D453,264 S | 2/2002 | Acevedo, Jr. |
| 6,347,629 B1 | 2/2002 | Braithwaite |
| 6,348,447 B1 | 2/2002 | Hellstorm et al. |
| 6,357,442 B1 | 3/2002 | Casper et al. |
| 6,358,058 B1 | 3/2002 | Strupat et al. |
| 6,358,924 B1 | 3/2002 | Hoffman |
| 6,360,743 B1 | 3/2002 | Andersson et al. |
| 6,360,929 B1 | 3/2002 | McCarthy |
| D455,208 S | 4/2002 | Bacon et al. |
| 6,363,932 B1 | 4/2002 | Forchione et al. |
| 6,365,190 B1 | 4/2002 | Gordon et al. |
| 6,372,258 B1 | 4/2002 | Platz et al. |
| 6,375,975 B1 | 4/2002 | Modi |
| 6,380,357 B2 | 4/2002 | Hermeling et al. |
| 6,386,195 B1 | 5/2002 | Coffee |
| 6,388,053 B1 | 5/2002 | Galloway et al. |
| 6,394,085 B1 | 5/2002 | Hardy et al. |
| 6,395,300 B1 | 5/2002 | Straub et al. |
| 6,395,744 B1 | 5/2002 | Adams et al. |
| 6,395,774 B1 | 5/2002 | Milstein |
| 6,410,513 B1 | 6/2002 | Galloway et al. |
| D460,173 S | 7/2002 | Harrison et al. |
| 6,415,784 B1 | 7/2002 | Christup et al. |
| 6,418,926 B1 | 7/2002 | Chawla |
| 6,423,344 B1 | 7/2002 | Platz et al. |
| D461,239 S | 8/2002 | Cassidy |
| 6,427,688 B1 | 8/2002 | Ligotke et al. |
| 6,428,771 B1 | 8/2002 | Steiner et al. |
| 6,428,805 B1 | 8/2002 | Dohi et al. |
| 6,432,383 B1 | 8/2002 | Modi |
| 6,436,443 B2 | 8/2002 | Edwards et al. |
| 6,439,227 B1 | 8/2002 | Myrman et al. |
| 6,440,463 B1 | 8/2002 | Feldstein et al. |
| 6,441,172 B1 | 8/2002 | Nefzi et al. |
| D463,544 S | 9/2002 | Engelberth et al. |
| 6,443,143 B1 | 9/2002 | Ishida et al. |

(56) References Cited

U.S. PATENT DOCUMENTS

| | | | |
|---|---|---|---|
| 6,444,226 B1 * | 9/2002 | Steiner | A61K 9/0075 424/434 |
| 6,446,626 B1 | 9/2002 | Virtanen | |
| 6,446,627 B1 | 9/2002 | Bowman et al. | |
| 6,447,750 B1 | 9/2002 | Cutie et al. | |
| 6,447,751 B1 | 9/2002 | Weinstein et al. | |
| 6,447,753 B2 | 9/2002 | Edwards et al. | |
| 6,451,337 B1 | 9/2002 | Smith et al. | |
| 6,457,470 B1 | 10/2002 | Coffee | |
| 6,468,507 B1 | 10/2002 | Cutie et al. | |
| 6,470,884 B2 | 10/2002 | Horlin | |
| 6,479,049 B1 | 11/2002 | Platz et al. | |
| 6,484,715 B1 | 11/2002 | Ritsche et al. | |
| 6,484,717 B1 | 11/2002 | Dagsland et al. | |
| D469,527 S | 1/2003 | Keller et al. | |
| 6,503,480 B1 | 1/2003 | Edwards et al. | |
| 6,509,006 B1 | 1/2003 | Platz et al. | |
| 6,509,313 B1 | 1/2003 | Smith | |
| D469,866 S | 2/2003 | Albulet et al. | |
| 6,514,482 B1 | 2/2003 | Bartus et al. | |
| 6,518,239 B1 | 2/2003 | Kuo et al. | |
| 6,523,536 B2 | 2/2003 | Fugelsang et al. | |
| D471,273 S | 3/2003 | Albulet et al. | |
| 6,528,096 B1 | 3/2003 | Musa et al. | |
| 6,532,437 B1 | 3/2003 | Clardy et al. | |
| 6,536,427 B2 | 3/2003 | Davies et al. | |
| D473,298 S | 4/2003 | Bowman et al. | |
| D473,640 S | 4/2003 | Cuffaro et al. | |
| 6,540,672 B1 | 4/2003 | Simonsen et al. | |
| 6,540,982 B1 | 4/2003 | Adjei et al. | |
| 6,540,983 B1 | 4/2003 | Adjei et al. | |
| 6,543,448 B1 | 4/2003 | Smith et al. | |
| 6,546,929 B2 | 4/2003 | Burr et al. | |
| 6,555,127 B2 | 4/2003 | Steiner | |
| 6,555,521 B2 | 4/2003 | Hermeling et al. | |
| D474,536 S | 5/2003 | Albulet et al. | |
| D475,133 S | 5/2003 | McLuckie | |
| 6,557,549 B2 | 5/2003 | Schmidt et al. | |
| 6,561,186 B2 | 5/2003 | Casper et al. | |
| 6,567,686 B2 | 5/2003 | Sexton | |
| 6,568,390 B2 | 5/2003 | Nichols et al. | |
| 6,569,406 B2 | 5/2003 | Stevenson et al. | |
| 6,571,793 B1 | 6/2003 | Nilsson et al. | |
| 6,572,893 B2 | 6/2003 | Gordon et al. | |
| 6,575,160 B1 | 6/2003 | Volgyesi | |
| 6,575,162 B1 | 6/2003 | Rand | |
| 6,578,571 B1 | 6/2003 | Watt | |
| 6,582,728 B1 | 6/2003 | Platz et al. | |
| 6,583,111 B1 | 6/2003 | DiMarchi | |
| D477,665 S | 7/2003 | Myrman et al. | |
| 6,589,560 B2 | 7/2003 | Foster et al. | |
| 6,591,832 B1 | 7/2003 | DeJonge | |
| 6,592,904 B2 | 7/2003 | Platz et al. | |
| 6,595,205 B2 | 7/2003 | Andersson et al. | |
| 6,595,208 B1 | 7/2003 | Coffee et al. | |
| D478,983 S | 8/2003 | Whitehall et al. | |
| 6,606,992 B1 | 8/2003 | Schuler et al. | |
| D479,745 S | 9/2003 | Albulet et al. | |
| 6,613,308 B2 | 9/2003 | Bartus et al. | |
| 6,615,987 B1 | 9/2003 | Greenhill et al. | |
| 6,620,910 B1 | 9/2003 | Calas et al. | |
| 6,626,173 B2 | 9/2003 | Genova et al. | |
| D480,806 S | 10/2003 | Engelberth et al. | |
| 6,630,169 B1 | 10/2003 | Bot et al. | |
| 6,632,258 B1 | 10/2003 | Wheelock et al. | |
| 6,632,456 B1 | 10/2003 | Backstrom et al. | |
| 6,635,283 B2 | 10/2003 | Edwards et al. | |
| 6,637,431 B2 | 10/2003 | Ekelius et al. | |
| 6,640,050 B2 | 10/2003 | Nichols et al. | |
| 6,644,309 B2 | 11/2003 | Casper et al. | |
| 6,645,468 B2 | 11/2003 | Cutie et al. | |
| 6,645,504 B1 | 11/2003 | Weiner et al. | |
| 6,652,838 B2 | 11/2003 | Weinstein et al. | |
| 6,652,885 B2 | 11/2003 | Steiner et al. | |
| D483,860 S | 12/2003 | Knoch | |
| 6,655,379 B2 | 12/2003 | Clark et al. | |
| 6,655,380 B1 | 12/2003 | Andersson et al. | |
| 6,655,381 B2 | 12/2003 | Keane et al. | |
| 6,660,716 B1 | 12/2003 | Yakubu-Madus et al. | |
| 6,663,898 B2 | 12/2003 | Milstein | |
| 6,668,826 B1 | 12/2003 | Myrman et al. | |
| 6,672,304 B1 | 1/2004 | Casper et al. | |
| 6,676,931 B2 | 1/2004 | Dugger, III | |
| 6,679,255 B2 | 1/2004 | Pera | |
| 6,681,767 B1 | 1/2004 | Patton et al. | |
| 6,681,768 B2 | 1/2004 | Haaije de Boer et al. | |
| 6,685,967 B1 | 2/2004 | Patton et al. | |
| 6,696,090 B1 | 2/2004 | Nilsson et al. | |
| 6,698,421 B2 | 3/2004 | Attolini | |
| 6,698,422 B2 | 3/2004 | Fugelsang et al. | |
| 6,698,425 B1 | 3/2004 | Widerstrom | |
| 6,701,917 B2 | 3/2004 | O'Leary | |
| 6,703,361 B2 | 3/2004 | Weiner et al. | |
| 6,703,365 B2 | 3/2004 | Galloway et al. | |
| 6,703,381 B1 | 3/2004 | Ekwuribe et al. | |
| 6,705,313 B2 | 3/2004 | Niccolai | |
| 6,715,486 B2 | 4/2004 | Gieschen et al. | |
| 6,715,487 B2 | 4/2004 | Nichols et al. | |
| 6,718,972 B2 | 4/2004 | O'Leary | |
| 6,720,407 B1 | 4/2004 | Hughes et al. | |
| 6,722,363 B1 | 4/2004 | von Schuckmann | |
| D489,448 S | 5/2004 | Shayan | |
| 6,729,324 B2 | 5/2004 | Casper et al. | |
| 6,729,328 B2 | 5/2004 | Raul | |
| 6,737,045 B2 | 5/2004 | Patton | |
| 6,745,761 B2 | 6/2004 | Christup et al. | |
| 6,747,006 B2 | 6/2004 | Efendic | |
| 6,748,946 B1 | 6/2004 | Rand et al. | |
| 6,748,947 B2 | 6/2004 | Keane et al. | |
| 6,752,145 B1 | 6/2004 | Bonney et al. | |
| 6,755,190 B2 | 6/2004 | Rasmussen | |
| D492,769 S | 7/2004 | Hatanaka | |
| D493,220 S | 7/2004 | Burge et al. | |
| D493,519 S | 7/2004 | Jonsson et al. | |
| 6,774,112 B2 | 8/2004 | Gougoutas | |
| 6,787,152 B2 | 9/2004 | Kirby et al. | |
| 6,790,496 B1 | 9/2004 | Levander et al. | |
| 6,792,945 B2 | 9/2004 | Davies et al. | |
| 6,797,258 B2 | 9/2004 | Platz et al. | |
| 6,799,572 B2 | 10/2004 | Nichols et al. | |
| 6,800,643 B2 | 10/2004 | Cuenoud et al. | |
| 6,803,044 B1 | 10/2004 | Catania et al. | |
| 6,821,949 B2 | 11/2004 | Bridon et al. | |
| 6,823,863 B2 | 11/2004 | Huxham et al. | |
| D499,802 S | 12/2004 | Pinon et al. | |
| 6,830,046 B2 | 12/2004 | Blakley et al. | |
| 6,838,075 B2 | 1/2005 | Stevenson et al. | |
| 6,838,076 B2 | 1/2005 | Platton et al. | |
| 6,847,595 B2 | 1/2005 | Tanaka | |
| 6,848,443 B2 | 2/2005 | Schmidt et al. | |
| 6,849,708 B1 | 2/2005 | Habener | |
| 6,852,690 B1 | 2/2005 | Nauck et al. | |
| 6,858,199 B1 | 2/2005 | Edwards et al. | |
| 6,860,262 B2 | 3/2005 | Christup et al. | |
| 6,866,037 B1 | 3/2005 | Aslin et al. | |
| 6,871,646 B2 | 3/2005 | Keane et al. | |
| 6,871,647 B2 | 3/2005 | Allan et al. | |
| 6,880,554 B1 | 4/2005 | Coffee | |
| 6,881,423 B2 | 4/2005 | Dohi et al. | |
| 6,884,435 B1 | 4/2005 | O'Hagan et al. | |
| 6,887,459 B1 | 5/2005 | Haeberlin | |
| 6,887,849 B2 | 5/2005 | Bridon et al. | |
| 6,889,687 B1 | 5/2005 | Olsson | |
| 6,892,728 B2 | 5/2005 | Helgesson et al. | |
| 6,896,906 B2 | 5/2005 | Hastedt et al. | |
| D506,680 S | 6/2005 | Saelzer | |
| 6,904,907 B2 | 6/2005 | Speldrich et al. | |
| 6,906,030 B2 | 6/2005 | Milstein | |
| 6,916,354 B2 | 7/2005 | Elliot | |
| 6,918,991 B2 | 7/2005 | Chickering, III et al. | |
| 6,921,458 B2 | 7/2005 | Chickering, III et al. | |
| 6,921,528 B2 | 7/2005 | Edwards et al. | |
| 6,923,175 B2 | 8/2005 | Poole et al. | |
| D509,296 S | 9/2005 | Minshull et al. | |

(56) References Cited

U.S. PATENT DOCUMENTS

| | | |
|---|---|---|
| D509,898 S | 9/2005 | Bunce et al. |
| 6,948,496 B2 | 9/2005 | Eason et al. |
| 6,949,258 B2 | 9/2005 | Zhang |
| 6,951,215 B1 | 10/2005 | Hoffman |
| 6,953,812 B2 | 10/2005 | Joregenson et al. |
| D511,208 S | 11/2005 | Pardonge et al. |
| D511,977 S | 11/2005 | Saelzer |
| 6,962,006 B2 | 11/2005 | Chickering, III et al. |
| D512,777 S | 12/2005 | Beisner et al. |
| 6,979,437 B2 | 12/2005 | Bartus et al. |
| D514,222 S | 1/2006 | Andersson et al. |
| 6,981,499 B2 | 1/2006 | Andersson et al. |
| 6,989,155 B1 | 1/2006 | Ganderton et al. |
| 6,991,779 B2 | 1/2006 | Steiner et al. |
| D515,696 S | 2/2006 | Lucking et al. |
| D515,924 S | 2/2006 | Grant |
| D516,211 S | 2/2006 | Minshull et al. |
| 6,998,387 B1 | 2/2006 | Goke et al. |
| D518,170 S | 3/2006 | Clarke et al. |
| D518,171 S | 3/2006 | Anderson et al. |
| 7,022,674 B2 | 4/2006 | DeFelippis et al. |
| 7,025,056 B2 | 4/2006 | Eason et al. |
| 7,028,686 B2 | 4/2006 | Gonda et al. |
| 7,030,084 B2 | 4/2006 | Ekwuribe et al. |
| 7,032,593 B2 | 4/2006 | Johnston et al. |
| 7,035,294 B2 | 4/2006 | Dove et al. |
| 7,047,967 B2 | 5/2006 | Knudsen |
| 7,048,908 B2 | 5/2006 | Basu et al. |
| 7,060,274 B2 | 6/2006 | Blumberg et al. |
| 7,067,129 B2 | 6/2006 | Blumberg et al. |
| 7,077,130 B2 | 7/2006 | Nichols et al. |
| 7,080,642 B2 | 7/2006 | Hodson et al. |
| 7,084,243 B2 | 8/2006 | Glaesner et al. |
| 7,093,594 B2 | 8/2006 | Harrison et al. |
| 7,093,595 B2 | 8/2006 | Nesbitt |
| D527,817 S | 9/2006 | Ziegler et al. |
| 7,101,843 B2 | 9/2006 | Glaesner et al. |
| 7,101,866 B2 | 9/2006 | Biggadike et al. |
| 7,105,489 B2 | 9/2006 | Hathaway |
| 7,107,988 B2 | 9/2006 | Pinon et al. |
| 7,109,161 B1 | 9/2006 | Gayed |
| D529,604 S | 10/2006 | Young et al. |
| 7,125,566 B2 | 10/2006 | Etter |
| 7,128,067 B2 | 10/2006 | Byron et al. |
| 7,131,441 B1 | 11/2006 | Keller et al. |
| 7,132,115 B2 | 11/2006 | Musa et al. |
| 7,140,365 B2 | 11/2006 | Poole et al. |
| D533,268 S | 12/2006 | Olfati |
| 7,143,764 B1 | 12/2006 | Dagsland et al. |
| 7,143,765 B2 | 12/2006 | Asking et al. |
| 7,144,863 B2 | 12/2006 | DeFelippis et al. |
| 7,146,978 B2 | 12/2006 | Edwards et al. |
| 7,151,456 B2 | 12/2006 | Godfrey |
| 7,163,014 B2 | 1/2007 | Nichols et al. |
| D537,522 S | 2/2007 | Cox et al. |
| 7,171,965 B2 | 2/2007 | Young et al. |
| 7,172,768 B2 | 2/2007 | Hastedt et al. |
| 7,179,788 B2 | 2/2007 | DeFelippis et al. |
| D537,936 S | 3/2007 | Cox et al. |
| D538,423 S | 3/2007 | Berube et al. |
| 7,185,650 B2 | 3/2007 | Huber et al. |
| D540,671 S | 4/2007 | Born |
| D541,151 S | 4/2007 | Born |
| 7,198,806 B2 | 4/2007 | Berndt |
| 7,211,557 B2 | 5/2007 | DiMarchi et al. |
| 7,219,664 B2 | 5/2007 | Ruckdeschel et al. |
| 7,223,728 B2 | 5/2007 | Yakubu-Madus et al. |
| D544,093 S | 6/2007 | Eriksen |
| 7,231,919 B2 | 6/2007 | Giroux |
| 7,232,897 B2 | 6/2007 | Hotamisligil et al. |
| 7,234,459 B2 | 6/2007 | Del Bon |
| 7,234,460 B2 | 6/2007 | Greenleaf et al. |
| 7,234,464 B2 | 6/2007 | Goede et al. |
| 7,238,663 B2 | 7/2007 | DeFelippis et al. |
| 7,246,617 B1 | 7/2007 | Hammer et al. |
| D548,330 S | 8/2007 | Cox et al. |
| D548,618 S | 8/2007 | Ferguson et al. |
| D548,619 S | 8/2007 | Ferguson et al. |
| D548,833 S | 8/2007 | Young et al. |
| D549,111 S | 8/2007 | Ferguson et al. |
| 7,258,118 B2 | 8/2007 | Goede et al. |
| 7,259,233 B2 | 8/2007 | Dodd et al. |
| D550,835 S | 9/2007 | Tanaka et al. |
| 7,265,087 B1 | 9/2007 | Goke et al. |
| 7,270,124 B2 | 9/2007 | Rasmussen |
| D552,729 S | 10/2007 | Cox et al. |
| 7,276,534 B2 | 10/2007 | Milstein |
| 7,278,419 B2 | 10/2007 | Gonda |
| 7,278,426 B2 | 10/2007 | Mryman et al. |
| 7,278,843 B2 | 10/2007 | Feldstein et al. |
| 7,279,457 B2 | 10/2007 | Pohl et al. |
| 7,284,553 B2 | 10/2007 | Hochrainer |
| D557,799 S | 12/2007 | Greenhalgh et al. |
| 7,305,986 B1 | 12/2007 | Steiner |
| 7,306,787 B2 | 12/2007 | Tarara et al. |
| D560,793 S | 1/2008 | Pearl et al. |
| 7,314,859 B2 | 1/2008 | Green et al. |
| 7,316,748 B2 | 1/2008 | Li et al. |
| 7,331,340 B2 | 2/2008 | Barney |
| 7,334,577 B2 | 2/2008 | Gumaste et al. |
| 7,344,734 B2 | 3/2008 | Heijerman et al. |
| D566,549 S | 4/2008 | Russell |
| 7,368,102 B2 | 5/2008 | Tarara et al. |
| 7,373,938 B2 | 5/2008 | Nichols et al. |
| 7,377,277 B2 | 5/2008 | Hickey et al. |
| 7,387,122 B2 | 6/2008 | Nishibayashi et al. |
| 7,399,528 B2 | 7/2008 | Caponetti et al. |
| 7,401,712 B2 | 7/2008 | Kaye et al. |
| 7,401,713 B2 | 7/2008 | Ede et al. |
| 7,402,564 B1 | 7/2008 | Schteingart et al. |
| 7,414,720 B2 | 8/2008 | Wachtel et al. |
| D577,815 S | 9/2008 | Gokhale et al. |
| 7,422,013 B2 | 9/2008 | Burr et al. |
| D579,549 S | 10/2008 | Birath et al. |
| 7,448,375 B2 | 11/2008 | Gonda et al. |
| 7,448,379 B2 | 11/2008 | Yamashita et al. |
| 7,451,761 B2 | 11/2008 | Hickey et al. |
| 7,453,556 B2 | 11/2008 | Hochrainer et al. |
| D583,463 S | 12/2008 | Wood et al. |
| 7,461,653 B2 | 12/2008 | Oliva |
| 7,462,367 B2 | 12/2008 | Schmidt et al. |
| 7,464,706 B2 | 12/2008 | Steiner et al. |
| 7,469,696 B2 | 12/2008 | Yang et al. |
| 7,500,479 B2 | 3/2009 | Nichols et al. |
| 7,503,324 B2 | 3/2009 | Barney et al. |
| 7,504,538 B2 | 3/2009 | Chang et al. |
| 7,517,874 B2 | 4/2009 | Beckett et al. |
| 7,520,278 B2 | 4/2009 | Crowder et al. |
| 7,521,069 B2 | 4/2009 | Patton et al. |
| 7,533,668 B1 | 5/2009 | Widerstrom |
| D594,753 S | 6/2009 | Eadicicco et al. |
| 7,556,798 B2 | 7/2009 | Edwards et al. |
| 7,559,322 B2 | 7/2009 | Foley et al. |
| D597,418 S | 8/2009 | Stojek |
| D597,657 S | 8/2009 | Kinsey et al. |
| D598,785 S | 8/2009 | Stojek |
| 7,584,846 B2 | 9/2009 | Senter |
| 7,598,222 B2 | 10/2009 | Prouty, Jr. et al. |
| D604,832 S | 11/2009 | Smutney |
| D604,833 S | 11/2009 | Polidoro |
| D605,752 S | 12/2009 | Polidoro |
| D605,753 S | 12/2009 | Smutney |
| 7,625,865 B2 | 12/2009 | Colombo |
| 7,648,960 B2 | 1/2010 | Steiner et al. |
| D613,849 S | 4/2010 | Smutney |
| D614,045 S | 4/2010 | Gaudenzi et al. |
| D614,760 S | 4/2010 | Smutney et al. |
| 7,694,676 B2 | 4/2010 | Wachtel |
| 7,708,014 B2 | 5/2010 | Yamashita et al. |
| 7,709,639 B2 | 5/2010 | Stevenson |
| 7,713,937 B2 | 5/2010 | Schteingart et al. |
| 7,727,963 B2 | 6/2010 | Schteingart et al. |
| 7,735,485 B2 | 6/2010 | Yamashita et al. |
| D620,812 S | 8/2010 | Gaudenzi et al. |

(56) References Cited

U.S. PATENT DOCUMENTS

| | | | |
|---|---|---|---|
| 7,794,754 B2 | 9/2010 | Feldstein et al. | |
| 7,799,344 B2 | 9/2010 | Oberg | |
| 7,803,404 B2 | 9/2010 | Hokenson | |
| 7,820,676 B2 * | 10/2010 | Leone-Bay | A61K 31/357 514/255.02 |
| D626,836 S | 11/2010 | Lien | |
| D628,090 S | 11/2010 | Stuiber et al. | |
| 7,833,549 B2 | 11/2010 | Steiner et al. | |
| 7,833,550 B2 | 11/2010 | Steiner et al. | |
| 7,842,662 B2 | 11/2010 | Schteingart et al. | |
| D629,505 S | 12/2010 | Adamo | |
| D629,506 S | 12/2010 | Adamo | |
| D629,886 S | 12/2010 | Adamo | |
| D629,887 S | 12/2010 | Adamo | |
| D629,888 S | 12/2010 | Adamo | |
| D635,241 S | 3/2011 | McLean | |
| D635,242 S | 3/2011 | Adamo | |
| D635,243 S | 3/2011 | Kinsey | |
| 7,913,688 B2 | 3/2011 | Cross | |
| D636,867 S | 4/2011 | Polidoro et al. | |
| D636,868 S | 4/2011 | Kinsey et al. | |
| D636,869 S | 4/2011 | Laurenzi et al. | |
| 7,919,119 B2 | 4/2011 | Straub et al. | |
| 7,943,178 B2 | 5/2011 | Steiner et al. | |
| 7,943,572 B2 | 5/2011 | Cheatham et al. | |
| 7,954,491 B2 | 6/2011 | Hrkach | |
| 7,959,609 B2 | 6/2011 | Gaydos et al. | |
| D641,076 S | 7/2011 | Grunstad et al. | |
| D643,308 S | 8/2011 | Bergey | |
| D645,954 S | 9/2011 | Hately | |
| D647,195 S | 10/2011 | Clarke et al. | |
| D647,196 S | 10/2011 | Clarke et al. | |
| 8,037,880 B2 | 10/2011 | Zhu et al. | |
| 8,037,881 B2 | 10/2011 | Pentafragas | |
| 8,039,431 B2 * | 10/2011 | Wilson | A61K 9/145 106/740 |
| 8,047,203 B2 | 11/2011 | Young et al. | |
| D652,322 S | 1/2012 | Stuiber et al. | |
| 8,109,267 B2 | 2/2012 | Villax et al. | |
| 8,119,593 B2 | 2/2012 | Richardson | |
| D655,622 S | 3/2012 | Sadler et al. | |
| 8,133,514 B2 | 3/2012 | Milstein | |
| 8,146,588 B2 | 4/2012 | Steiner et al. | |
| 8,156,936 B2 | 4/2012 | Steiner et al. | |
| D659,020 S | 5/2012 | Kemner | |
| D659,022 S | 5/2012 | Kemner | |
| D660,956 S | 5/2012 | Zuyderhoudt | |
| 8,166,970 B2 | 5/2012 | Poole et al. | |
| 8,172,817 B2 | 5/2012 | Michaels et al. | |
| 8,196,576 B2 | 6/2012 | Kriksunov et al. | |
| 8,201,555 B2 | 6/2012 | Chawla | |
| 8,202,992 B2 | 6/2012 | Stevenson | |
| D663,830 S | 7/2012 | Sears | |
| D664,640 S | 7/2012 | Smutney et al. | |
| 8,215,300 B2 | 7/2012 | Steiner et al. | |
| 8,217,007 B1 | 7/2012 | Schteingart et al. | |
| 8,227,409 B2 | 7/2012 | Kraft | |
| 8,236,766 B2 | 8/2012 | Schteingart et al. | |
| 8,252,916 B2 | 8/2012 | Simard et al. | |
| 8,258,095 B2 | 9/2012 | Boss et al. | |
| 8,278,308 B2 | 10/2012 | Leone-Bay et al. | |
| 8,293,869 B2 | 10/2012 | Bossard | |
| 8,314,106 B2 | 11/2012 | Kraft | |
| D671,842 S | 12/2012 | Bergey | |
| D674,893 S | 1/2013 | Kinsey et al. | |
| 8,372,804 B2 | 2/2013 | Richardson | |
| 8,377,869 B2 | 2/2013 | Richardson | |
| 8,389,470 B2 | 3/2013 | Steiner | |
| 8,394,414 B2 | 3/2013 | Steiner et al. | |
| 8,408,200 B2 | 4/2013 | Clark et al. | |
| 8,420,604 B2 | 4/2013 | Hokenson | |
| 8,424,518 B2 | 4/2013 | Smutney | |
| 8,485,180 B2 | 7/2013 | Smutney et al. | |
| 8,486,894 B2 | 7/2013 | Schteingart et al. | |
| 8,499,757 B2 | 8/2013 | Smutney | |
| 8,512,932 B2 * | 8/2013 | Wilson | A61K 9/145 106/740 |
| 8,522,775 B2 | 9/2013 | Malhotra et al. | |
| 8,536,131 B2 | 9/2013 | Schteingart et al. | |
| 8,538,707 B2 | 9/2013 | Adamo et al. | |
| 8,539,946 B2 | 9/2013 | Esteve et al. | |
| 8,551,528 B2 | 10/2013 | Grant et al. | |
| 8,563,101 B2 | 10/2013 | Spallek | |
| 8,636,001 B2 | 1/2014 | Smutney | |
| 8,642,548 B2 | 2/2014 | Richardson et al. | |
| 8,671,937 B2 | 3/2014 | Steiner et al. | |
| 8,677,992 B2 | 3/2014 | Villax | |
| 8,763,606 B2 | 7/2014 | Mosier et al. | |
| 8,778,403 B2 | 7/2014 | Grant et al. | |
| 8,783,249 B2 | 7/2014 | Poole et al. | |
| D711,740 S | 8/2014 | Lien | |
| 8,808,786 B2 | 8/2014 | Jinks et al. | |
| 8,820,324 B2 | 9/2014 | Smith et al. | |
| 8,909,487 B2 | 12/2014 | Adamo et al. | |
| 8,925,726 B2 | 1/2015 | Bergey | |
| 9,041,925 B2 | 5/2015 | Adamo et al. | |
| 9,138,407 B2 | 9/2015 | Caponetti et al. | |
| 9,241,903 B2 * | 1/2016 | Wilson | A61K 9/145 |
| D771,237 S | 11/2016 | Smutney et al. | |
| 2001/0020147 A1 | 9/2001 | Staniforth et al. | |
| 2001/0039442 A1 | 11/2001 | Gorge et al. | |
| 2002/0000225 A1 | 1/2002 | Schuler et al. | |
| 2002/0015737 A1 | 2/2002 | Shih et al. | |
| 2002/0033177 A1 | 3/2002 | Ohki et al. | |
| 2002/0052381 A1 | 5/2002 | Bar-Or et al. | |
| 2002/0053344 A1 | 5/2002 | Davies et al. | |
| 2002/0053347 A1 | 5/2002 | Ziaee | |
| 2002/0065239 A1 | 5/2002 | Caplan et al. | |
| 2002/0088462 A1 | 7/2002 | Genova et al. | |
| 2002/0101590 A1 | 8/2002 | Shimaoka | |
| 2002/0144680 A1 | 10/2002 | Nilsson et al. | |
| 2002/0161001 A1 | 10/2002 | Kanstrup et al. | |
| 2003/0000524 A1 | 1/2003 | Andersson et al. | |
| 2003/0010794 A1 | 1/2003 | Herdtle et al. | |
| 2003/0013641 A1 | 1/2003 | Steiner et al. | |
| 2003/0017211 A1 | 1/2003 | Steiner | |
| 2003/0053960 A1 | 3/2003 | Heijerman et al. | |
| 2003/0064097 A1 | 4/2003 | Patel et al. | |
| 2003/0068378 A1 | 4/2003 | Chen et al. | |
| 2003/0099636 A1 | 5/2003 | Epshtein et al. | |
| 2003/0136405 A1 | 7/2003 | Goede et al. | |
| 2003/0168370 A1 | 9/2003 | Merboth et al. | |
| 2003/0194420 A1 | 10/2003 | Holl et al. | |
| 2003/0235538 A1 | 12/2003 | Zirenberg | |
| 2004/0022861 A1 | 2/2004 | Williams et al. | |
| 2004/0024180 A1 | 2/2004 | Drauz | |
| 2004/0025875 A1 | 2/2004 | Reber et al. | |
| 2004/0034014 A1 | 2/2004 | Kanstrup et al. | |
| 2004/0038865 A1 | 2/2004 | Gelber et al. | |
| 2004/0053819 A1 | 3/2004 | Dodd et al. | |
| 2004/0062722 A1 | 4/2004 | Gonda et al. | |
| 2004/0076588 A1 | 4/2004 | Batycky et al. | |
| 2004/0077528 A1 | 4/2004 | Steiner et al. | |
| 2004/0096403 A1 | 5/2004 | Steiner | |
| 2004/0107963 A1 | 6/2004 | Finlay et al. | |
| 2004/0121964 A1 | 6/2004 | Madar et al. | |
| 2004/0138099 A1 | 7/2004 | Draeger | |
| 2004/0151059 A1 | 8/2004 | Robert, II et al. | |
| 2004/0151774 A1 | 8/2004 | Pauletti et al. | |
| 2004/0157928 A1 | 8/2004 | Kim et al. | |
| 2004/0163648 A1 | 8/2004 | Burton | |
| 2004/0182387 A1 | 9/2004 | Steiner et al. | |
| 2004/0187869 A1 | 9/2004 | Bjorndal et al. | |
| 2004/0204439 A1 | 10/2004 | Staniforth et al. | |
| 2004/0204440 A1 | 10/2004 | Staniforth et al. | |
| 2004/0211419 A1 | 10/2004 | Eason et al. | |
| 2004/0211420 A1 | 10/2004 | Minshull | |
| 2004/0234615 A1 | 11/2004 | Sabetsky | |
| 2004/0234616 A1 | 11/2004 | Sabetsky | |
| 2004/0235956 A1 | 11/2004 | Quay | |
| 2004/0241232 A1 | 12/2004 | Brown et al. | |
| 2004/0247628 A1 | 12/2004 | Lintz et al. | |
| 2004/0250812 A1 | 12/2004 | Davies et al. | |
| 2005/0000518 A1 | 1/2005 | Dunkley et al. | |

(56) References Cited

U.S. PATENT DOCUMENTS

| | | |
|---|---|---|
| 2005/0039743 A1 | 2/2005 | Taylor |
| 2005/0043228 A1 | 2/2005 | DeFelippis et al. |
| 2005/0043247 A1 | 2/2005 | Trunk et al. |
| 2005/0056281 A1 | 3/2005 | Snow |
| 2005/0070469 A1 | 3/2005 | Bloom |
| 2005/0080000 A1 | 4/2005 | Thurow et al. |
| 2005/0119604 A1 | 6/2005 | Bonney et al. |
| 2005/0124644 A1 | 6/2005 | Nilsson et al. |
| 2005/0147581 A1 | 7/2005 | Zamiri et al. |
| 2005/0153874 A1 | 7/2005 | Cheatham et al. |
| 2005/0155601 A1 | 7/2005 | Steiner et al. |
| 2005/0183723 A1 | 8/2005 | Pinon et al. |
| 2005/0187749 A1 | 8/2005 | Singley |
| 2005/0203002 A1 | 9/2005 | Tzannis et al. |
| 2005/0214251 A1 | 9/2005 | Pohl et al. |
| 2005/0252508 A1 | 11/2005 | Koerner |
| 2005/0265927 A1 | 12/2005 | Lee |
| 2005/0274378 A1 | 12/2005 | Bonney et al. |
| 2006/0000469 A1 | 1/2006 | Tseng |
| 2006/0003316 A1 | 1/2006 | Simard et al. |
| 2006/0040953 A1 | 2/2006 | Leone-Bay et al. |
| 2006/0041133 A1 | 2/2006 | Stevenson et al. |
| 2006/0062740 A1 | 3/2006 | Rand |
| 2006/0099269 A1 | 5/2006 | Cheatham et al. |
| 2006/0102511 A1 | 5/2006 | Pasbrig et al. |
| 2006/0120969 A1 | 6/2006 | Nilsson et al. |
| 2006/0153778 A1 | 7/2006 | Gelber et al. |
| 2006/0160722 A1 | 7/2006 | Green et al. |
| 2006/0165756 A1 | 7/2006 | Catani et al. |
| 2006/0219242 A1 | 10/2006 | Zierenberg |
| 2006/0239933 A1 | 10/2006 | Nilsson et al. |
| 2006/0239934 A1 | 10/2006 | Cheatham et al. |
| 2006/0243275 A1 | 11/2006 | Ruckdeschel et al. |
| 2006/0249419 A1 | 11/2006 | Taylor et al. |
| 2006/0260777 A1 | 11/2006 | Rashba-Step et al. |
| 2006/0283758 A1 | 12/2006 | Pasbrig |
| 2007/0006876 A1 | 1/2007 | Finlay et al. |
| 2007/0017506 A1 | 1/2007 | Bell et al. |
| 2007/0020191 A1 | 1/2007 | Boss et al. |
| 2007/0027063 A1 | 2/2007 | Boss et al. |
| 2007/0044793 A1 | 3/2007 | Kleinstreuer et al. |
| 2007/0049576 A1 | 3/2007 | Barlow et al. |
| 2007/0059373 A1 | 3/2007 | Berg |
| 2007/0059374 A1 | 3/2007 | Hokenson et al. |
| 2007/0074989 A1 | 4/2007 | Merboth et al. |
| 2007/0077219 A1 | 4/2007 | Fahl et al. |
| 2007/0086952 A1 | 4/2007 | Steiner |
| 2007/0099454 A1 | 5/2007 | Gordon |
| 2007/0125375 A1 | 6/2007 | Finlay et al. |
| 2007/0128193 A1 | 6/2007 | O'Neil et al. |
| 2007/0151562 A1 | 7/2007 | Jones |
| 2007/0160789 A1 | 7/2007 | Merical et al. |
| 2007/0175314 A1 | 8/2007 | Wanne |
| 2007/0190163 A1 | 8/2007 | Malaknov et al. |
| 2007/0191462 A1 | 8/2007 | Hettiarachchi |
| 2007/0196503 A1 | 8/2007 | Wilson et al. |
| 2007/0207958 A1 | 9/2007 | Bridon et al. |
| 2007/0225587 A1 | 9/2007 | Burnell et al. |
| 2007/0235029 A1 | 10/2007 | Zhu et al. |
| 2007/0240708 A1 | 10/2007 | Schuckmann |
| 2007/0272763 A1 | 11/2007 | Dunne et al. |
| 2007/0277820 A1 | 12/2007 | Crowder et al. |
| 2007/0277821 A1 | 12/2007 | Oliva et al. |
| 2007/0295332 A1 | 12/2007 | Ziegler |
| 2007/0299074 A1 | 12/2007 | Netz et al. |
| 2008/0008764 A1 | 1/2008 | Milstein |
| 2008/0015457 A1 | 1/2008 | Silva |
| 2008/0039368 A1 | 2/2008 | Steiner et al. |
| 2008/0039402 A1 | 2/2008 | Mossalayi et al. |
| 2008/0047550 A2 | 2/2008 | Steiner et al. |
| 2008/0066739 A1 | 3/2008 | LeMahieu et al. |
| 2008/0108554 A1 | 5/2008 | Jackson et al. |
| 2008/0108574 A1 | 5/2008 | Barlow et al. |
| 2008/0115785 A1 | 5/2008 | Eason et al. |
| 2008/0127970 A1 | 6/2008 | Steiner et al. |
| 2008/0127974 A1 | 6/2008 | Lastow |
| 2008/0129791 A1 | 6/2008 | King et al. |
| 2008/0168987 A1 | 7/2008 | Denny et al. |
| 2008/0190424 A1 | 8/2008 | Lucking et al. |
| 2008/0197044 A1 | 8/2008 | Hickey et al. |
| 2008/0216824 A1 | 9/2008 | Ooida |
| 2008/0217199 A1 | 9/2008 | Burress et al. |
| 2008/0255468 A1 | 10/2008 | Derchak et al. |
| 2008/0260838 A1 | 10/2008 | Hokenson et al. |
| 2008/0260840 A1 | 10/2008 | Alessi |
| 2008/0295833 A1 | 12/2008 | Rohrschneider et al. |
| 2008/0312155 A1 | 12/2008 | Kitada et al. |
| 2008/0314384 A1 | 12/2008 | Harris et al. |
| 2008/0319333 A1 | 12/2008 | Gavish et al. |
| 2009/0025720 A1 | 1/2009 | Chen |
| 2009/0068274 A1 | 3/2009 | Edwards et al. |
| 2009/0084379 A1 | 4/2009 | Goeckner et al. |
| 2009/0084380 A1 | 4/2009 | Gieschen et al. |
| 2009/0134051 A1 | 5/2009 | Rapp et al. |
| 2009/0149727 A1 | 6/2009 | Truitt et al. |
| 2009/0151720 A1 | 6/2009 | Inoue et al. |
| 2009/0178676 A1 | 7/2009 | Villax et al. |
| 2009/0205657 A1 | 8/2009 | Barney et al. |
| 2009/0209502 A1 | 8/2009 | Haeberlin et al. |
| 2009/0232891 A1 | 9/2009 | Gelber et al. |
| 2009/0241949 A1 | 10/2009 | Smutney |
| 2009/0250058 A1 | 10/2009 | Lastow |
| 2009/0258818 A1 | 10/2009 | Surolia et al. |
| 2009/0314291 A1 | 12/2009 | Anderson et al. |
| 2009/0314292 A1 | 12/2009 | Overfield |
| 2009/0320837 A1 | 12/2009 | Smith et al. |
| 2010/0012120 A1 | 1/2010 | Herder |
| 2010/0051027 A1 | 3/2010 | Remmelgas et al. |
| 2010/0065048 A1 | 3/2010 | Walz et al. |
| 2010/0086609 A1 | 4/2010 | Steiner et al. |
| 2010/0113363 A1 | 5/2010 | Holst et al. |
| 2010/0163042 A1 | 7/2010 | Bhowmick et al. |
| 2010/0180894 A1 | 7/2010 | Jones et al. |
| 2010/0181225 A1 | 7/2010 | Spallek et al. |
| 2010/0190701 A1 | 7/2010 | Day et al. |
| 2010/0193380 A1 | 8/2010 | Sullivan et al. |
| 2010/0197565 A1 | 8/2010 | Smutney et al. |
| 2010/0212667 A1 | 8/2010 | Smith et al. |
| 2010/0235116 A1 | 9/2010 | Adamo et al. |
| 2010/0238457 A1 | 9/2010 | Adamo et al. |
| 2010/0278924 A1 | 11/2010 | Oberg |
| 2010/0288276 A1 | 11/2010 | Ganderton et al. |
| 2010/0326438 A1 | 12/2010 | Dunne |
| 2011/0000482 A1 | 1/2011 | Gumaste et al. |
| 2011/0003004 A1 | 1/2011 | Hokenson |
| 2011/0011394 A1 | 1/2011 | Edwards et al. |
| 2011/0023876 A1 | 2/2011 | Vehring et al. |
| 2011/0083667 A1 | 4/2011 | Briant |
| 2011/0155129 A1 | 6/2011 | Stedman et al. |
| 2011/0158935 A1 | 6/2011 | Kraft |
| 2011/0183901 A1 | 7/2011 | Cheatham |
| 2012/0014999 A1 | 1/2012 | Grant et al. |
| 2012/0040899 A1 | 2/2012 | Costello |
| 2012/0071510 A1 | 3/2012 | Leone-Bay et al. |
| 2012/0094905 A1 | 4/2012 | Costello |
| 2012/0115777 A1 | 5/2012 | Richardson |
| 2012/0122775 A1 | 5/2012 | Boss et al. |
| 2012/0160241 A1 | 6/2012 | Oliva |
| 2012/0164186 A1 | 6/2012 | Grant et al. |
| 2012/0178935 A1 | 7/2012 | Stevenson |
| 2012/0192865 A1 | 8/2012 | Steiner et al. |
| 2012/0207913 A1 | 8/2012 | Smyth |
| 2012/0240929 A1 | 9/2012 | Steiner et al. |
| 2012/0247235 A1 | 10/2012 | Adamo et al. |
| 2012/0247465 A1 | 10/2012 | Wachtel |
| 2012/0328676 A1 | 12/2012 | Leone-Bay et al. |
| 2013/0012710 A1 | 1/2013 | Freeman et al. |
| 2013/0053309 A1 | 2/2013 | Kraft |
| 2013/0104887 A1 | 5/2013 | Smutney et al. |
| 2013/0118491 A1 | 5/2013 | Richardson et al. |
| 2013/0125886 A1 | 5/2013 | Richardson et al. |
| 2013/0143801 A1 | 6/2013 | Steiner et al. |
| 2013/0189365 A1 | 7/2013 | Hokenson |
| 2013/0199527 A1 | 8/2013 | Smutney et al. |

(56) References Cited

U.S. PATENT DOCUMENTS

| | | | |
|---|---|---|---|
| 2013/0289278 A1 | 10/2013 | Kraft | |
| 2013/0291866 A1 | 11/2013 | Smutney | |
| 2013/0291867 A1 | 11/2013 | Smutney | |
| 2013/0303445 A1 | 11/2013 | Wilson et al. | |
| 2013/0338065 A1 | 12/2013 | Smutney | |
| 2014/0007873 A1 | 1/2014 | Smutney | |
| 2014/0014106 A1 | 1/2014 | Smutney | |
| 2014/0083421 A1 | 3/2014 | Smutney | |
| 2014/0096771 A1 | 4/2014 | Remmelgas et al. | |
| 2014/0100158 A1 | 4/2014 | Richardson et al. | |
| 2014/0187490 A1 | 7/2014 | Richardson et al. | |
| 2014/0199398 A1 | 7/2014 | Grant et al. | |
| 2014/0227359 A1 | 8/2014 | Leone-Bay et al. | |
| 2014/0243530 A1 | 8/2014 | Stevenson et al. | |
| 2014/0271888 A1 | 9/2014 | Grant et al. | |
| 2014/0290654 A1 | 10/2014 | Poole et al. | |
| 2014/0302151 A1 | 10/2014 | Leone-Bay et al. | |
| 2014/0308358 A1 | 10/2014 | Oberg et al. | |
| 2014/0315953 A1 | 10/2014 | Leone-Bay et al. | |
| 2015/0031609 A1 | 1/2015 | Steiner et al. | |
| 2015/0045295 A1 | 2/2015 | Smutney et al. | |
| 2015/0052977 A1 | 2/2015 | Adamo et al. | |
| 2015/0065422 A1 | 3/2015 | Kraft | |
| 2015/0080298 A1 | 3/2015 | Costello et al. | |
| 2015/0108023 A1 | 4/2015 | Bergey | |
| 2015/0122258 A1 | 5/2015 | Steiner et al. | |
| 2015/0150980 A1 | 6/2015 | Leone-Bay et al. | |
| 2015/0174210 A1 | 6/2015 | Boss et al. | |
| 2015/0196724 A1 | 7/2015 | Adamo et al. | |
| 2015/0226656 A1 | 8/2015 | Adamo et al. | |
| 2015/0231067 A1 | 8/2015 | Mann | |
| 2015/0246188 A1 | 9/2015 | Steiner et al. | |
| 2015/0283069 A1 | 10/2015 | Smutney et al. | |
| 2015/0283213 A1 | 10/2015 | Costello et al. | |
| 2015/0290132 A1 | 10/2015 | Gelber et al. | |
| 2015/0359744 A1 | 12/2015 | Hokenson et al. | |
| 2016/0095990 A1 | 4/2016 | Smutney et al. | |
| 2016/0101049 A1 | 4/2016 | Wilson et al. | |
| 2016/0151287 A1 | 6/2016 | Oberg et al. | |
| 2016/0158156 A1 | 6/2016 | Fabio et al. | |
| 2016/0175079 A1 | 6/2016 | Adamo et al. | |
| 2016/0193432 A1 | 7/2016 | Harris et al. | |
| 2016/0221967 A1 | 8/2016 | Stevenson et al. | |
| 2016/0228659 A1 | 8/2016 | Smutney et al. | |
| 2016/0243322 A1 | 8/2016 | Smutney et al. | |
| 2016/0250297 A1 | 9/2016 | Leone-Bay et al. | |
| 2016/0256640 A1 | 9/2016 | Overfield et al. | |
| 2016/0287820 A1 | 10/2016 | Smutney et al. | |
| 2016/0346212 A1 | 12/2016 | Hokenson et al. | |
| 2016/0346394 A1 | 12/2016 | Grant et al. | |

FOREIGN PATENT DOCUMENTS

| | | |
|---|---|---|
| CN | 101290219 A | 10/2008 |
| CN | 101851213 | 10/2010 |
| CN | 102436238 A | 5/2012 |
| DE | 2840442 C2 | 2/1982 |
| DE | 3639836 A1 | 6/1988 |
| DE | 19519840 A1 | 12/1996 |
| EP | 69715 | 1/1983 |
| EP | 122036 | 10/1984 |
| EP | 143524 | 6/1985 |
| EP | 180543 | 5/1986 |
| EP | 220958 | 5/1987 |
| EP | 237507 | 8/1987 |
| EP | 257915 | 2/1988 |
| EP | 308637 A1 | 3/1989 |
| EP | 360340 | 3/1990 |
| EP | 364235 | 4/1990 |
| EP | 387222 A | 9/1990 |
| EP | 388621 A | 9/1990 |
| EP | 606486 | 12/1993 |
| EP | 581473 A1 | 2/1994 |
| EP | 655237 | 5/1995 |
| EP | 666085 A1 | 8/1995 |
| EP | 748213 | 12/1996 |
| EP | 558879 B1 | 5/1997 |
| EP | 844007 | 12/1998 |
| EP | 1060741 A1 | 12/2000 |
| EP | 1114644 | 7/2001 |
| EP | 0837710 B1 | 11/2001 |
| EP | 640354 B1 | 12/2001 |
| EP | 1348428 A1 | 10/2003 |
| EP | 1364967 | 11/2003 |
| EP | 825885 B1 | 3/2004 |
| EP | 96911738 | 6/2004 |
| EP | 1598066 | 11/2005 |
| EP | 833652 B1 | 2/2008 |
| EP | 1923087 A2 | 5/2008 |
| EP | 2060268 A1 | 5/2009 |
| EP | 2314298 A | 4/2011 |
| GB | 475440 A | 11/1937 |
| GB | 716815 | 10/1954 |
| GB | 2072536 A | 10/1981 |
| GB | 2148841 A | 6/1985 |
| GB | 2240337 | 7/1991 |
| GB | 2253200 A | 9/1992 |
| GB | 2262452 | 6/1993 |
| GB | 2398065 A | 8/2004 |
| JP | S55-156085 U | 11/1980 |
| JP | 63-020301 | 1/1988 |
| JP | 2115154 A | 4/1990 |
| JP | 2-149545 | 2/1992 |
| JP | H07-041428 | 2/1995 |
| JP | 09-208485 | 8/1997 |
| JP | 10234827 A | 9/1998 |
| JP | 2002322294 | 11/2002 |
| JP | 2003-503420 | 1/2003 |
| JP | 2004-121061 | 4/2004 |
| JP | 2006-280620 A | 10/2006 |
| JP | 2007-061281 | 3/2007 |
| TW | 200505517 A | 2/2005 |
| WO | 1990/013285 | 11/1990 |
| WO | 1991/004011 | 4/1991 |
| WO | 1991/006287 | 5/1991 |
| WO | 1991/016038 | 10/1991 |
| WO | 1991/016882 | 11/1991 |
| WO | 1991/019524 | 12/1991 |
| WO | 1992/004069 | 3/1992 |
| WO | 1992/008509 | 5/1992 |
| WO | 1993/002712 | 2/1993 |
| WO | 1993/014110 | 7/1993 |
| WO | 1993/017728 | 9/1993 |
| WO | 1993/018754 A1 | 9/1993 |
| WO | 1994/000291 | 1/1994 |
| WO | 1994/008552 | 4/1994 |
| WO | 1994/008599 | 4/1994 |
| WO | 1994/019041 | 9/1994 |
| WO | 1994/023702 | 10/1994 |
| WO | 1994/025005 A1 | 11/1994 |
| WO | 1995/000127 A1 | 1/1995 |
| WO | 1995/005208 | 2/1995 |
| WO | 1995/011666 | 5/1995 |
| WO | 1995/024183 A1 | 9/1995 |
| WO | 1995/031979 | 11/1995 |
| WO | 1995/034294 | 12/1995 |
| WO | 1996/001105 | 1/1996 |
| WO | 1996/005810 | 2/1996 |
| WO | 1996/013250 | 5/1996 |
| WO | 1996/022802 A | 8/1996 |
| WO | 1996/027386 A1 | 9/1996 |
| WO | 1996/032149 | 10/1996 |
| WO | 1996/036314 | 11/1996 |
| WO | 1996/036317 A1 | 11/1996 |
| WO | 1996/040206 A1 | 12/1996 |
| WO | 1997/001365 | 1/1997 |
| WO | 1997/004747 | 2/1997 |
| WO | 1997/025086 A2 | 7/1997 |
| WO | 1997/030743 | 8/1997 |
| WO | 1997/035562 A1 | 10/1997 |
| WO | 1997/046206 | 12/1997 |
| WO | 1997/049386 | 12/1997 |
| WO | 1998/026827 A1 | 6/1998 |
| WO | 1998/034661 A1 | 8/1998 |

(56) References Cited

FOREIGN PATENT DOCUMENTS

| | | |
|---|---|---|
| WO | 1998/039043 | 9/1998 |
| WO | 1998/041255 A2 | 9/1998 |
| WO | 1998/043615 | 10/1998 |
| WO | 1999/014239 A1 | 3/1999 |
| WO | 1999/018939 A1 | 4/1999 |
| WO | 1999/032510 A1 | 7/1999 |
| WO | 1999/033862 | 7/1999 |
| WO | 1999/052506 | 10/1999 |
| WO | 2000/12116 | 3/2000 |
| WO | 2000/033811 A2 | 6/2000 |
| WO | 2000/059476 A1 | 10/2000 |
| WO | 2000/071154 A2 | 11/2000 |
| WO | 2001/000654 | 1/2001 |
| WO | 2001/081321 A | 1/2001 |
| WO | 2001/049274 A2 | 7/2001 |
| WO | 2001/051071 | 7/2001 |
| WO | 2001/052813 A1 | 7/2001 |
| WO | 2001/066064 | 9/2001 |
| WO | 2001/068169 | 9/2001 |
| WO | 2001/097886 A1 | 12/2001 |
| WO | 2001/007107 | 2/2002 |
| WO | 2002/011676 | 2/2002 |
| WO | 2002/012201 A1 | 2/2002 |
| WO | 2002/047659 A2 | 6/2002 |
| WO | 2002/058735 | 8/2002 |
| WO | 2002/059574 A1 | 8/2002 |
| WO | 2002/067995 A1 | 9/2002 |
| WO | 2002/085281 | 10/2002 |
| WO | 2002/098348 | 12/2002 |
| WO | 2002/102444 | 12/2002 |
| WO | 2003/000202 | 1/2003 |
| WO | 2003/015857 A1 | 2/2003 |
| WO | 2003/018059 A2 | 3/2003 |
| WO | 2003/022304 A1 | 3/2003 |
| WO | 2003/055547 A1 | 7/2003 |
| WO | 2003/057170 | 7/2003 |
| WO | 2003/061578 A2 | 7/2003 |
| WO | 2003/072195 A2 | 9/2003 |
| WO | 2003/080149 A2 | 10/2003 |
| WO | 2003/084502 A1 | 10/2003 |
| WO | 2003/086345 | 10/2003 |
| WO | 2003/094951 | 11/2003 |
| WO | 2004/012672 | 2/2004 |
| WO | 2004/012720 | 2/2004 |
| WO | 2004/033010 | 4/2004 |
| WO | 2004/035121 | 4/2004 |
| WO | 2004/041338 | 5/2004 |
| WO | 2004/050152 | 6/2004 |
| WO | 2004/054647 A1 | 7/2004 |
| WO | 2004/056314 | 7/2004 |
| WO | 2004/060458 | 7/2004 |
| WO | 2004/064862 | 8/2004 |
| WO | 2004/075919 | 9/2004 |
| WO | 2004/080401 | 9/2004 |
| WO | 2004/080482 | 9/2004 |
| WO | 2004/103304 A2 | 12/2004 |
| WO | 2005/002654 A2 | 1/2005 |
| WO | 2005/020964 | 3/2005 |
| WO | 2005/023348 A | 3/2005 |
| WO | 2005/028699 A1 | 3/2005 |
| WO | 2005/067964 | 7/2005 |
| WO | 2005/081977 A2 | 9/2005 |
| WO | 2005/089722 | 9/2005 |
| WO | 2005/089843 | 9/2005 |
| WO | 2005/102428 A1 | 11/2005 |
| WO | 2005/102429 | 11/2005 |
| WO | 2005/113042 A1 | 12/2005 |
| WO | 2005/113043 | 12/2005 |
| WO | 2005/120616 | 12/2005 |
| WO | 2006/010248 | 2/2006 |
| WO | 2006/017688 A2 | 2/2006 |
| WO | 2006/023849 | 3/2006 |
| WO | 2006/023943 | 3/2006 |
| WO | 2006/023944 | 3/2006 |
| WO | 2006/037636 | 4/2006 |
| WO | 2006/059939 | 6/2006 |
| WO | 2006/061637 A2 | 6/2006 |
| WO | 2006/086107 A2 | 8/2006 |
| WO | 2006/090149 | 8/2006 |
| WO | 2006/105501 | 10/2006 |
| WO | 2007/007110 A1 | 1/2007 |
| WO | 2007/016600 A2 | 2/2007 |
| WO | 2007/019229 | 2/2007 |
| WO | 2007/024953 A1 | 3/2007 |
| WO | 2007/030706 | 3/2007 |
| WO | 2007/033316 | 3/2007 |
| WO | 2007/033372 A2 | 3/2007 |
| WO | 2007/042822 | 4/2007 |
| WO | 2007/068896 | 6/2007 |
| WO | 2007/075534 A2 | 7/2007 |
| WO | 2007/093310 | 8/2007 |
| WO | 2007/098500 | 8/2007 |
| WO | 2007/100535 | 9/2007 |
| WO | 2007/118342 | 10/2007 |
| WO | 2007/118343 A1 | 10/2007 |
| WO | 2007/121411 | 10/2007 |
| WO | 2007/132217 | 11/2007 |
| WO | 2007/144607 | 12/2007 |
| WO | 2007/144614 | 12/2007 |
| WO | 2008/001744 | 1/2008 |
| WO | 2008/008021 | 1/2008 |
| WO | 2008/014613 A1 | 2/2008 |
| WO | 2008/020217 | 2/2008 |
| WO | 2008/060484 A2 | 5/2008 |
| WO | 2008/092864 | 8/2008 |
| WO | 2008/110809 | 9/2008 |
| WO | 2009/005546 A1 | 1/2009 |
| WO | 2009/008001 A2 | 1/2009 |
| WO | 2009/009013 A2 | 1/2009 |
| WO | 2009/047281 A1 | 4/2009 |
| WO | 2009/055030 | 4/2009 |
| WO | 2009/055740 | 4/2009 |
| WO | 2009/055742 | 4/2009 |
| WO | 2009/095684 A1 | 8/2009 |
| WO | 2009/121020 A1 | 10/2009 |
| WO | 2009/140587 A1 | 11/2009 |
| WO | 2009/152477 A2 | 12/2009 |
| WO | 2009/155581 A1 | 12/2009 |
| WO | 2010/021879 A2 | 2/2010 |
| WO | 2010/078373 A1 | 7/2010 |
| WO | 2010/080964 | 7/2010 |
| WO | 2010/102148 | 9/2010 |
| WO | 2010/105094 A1 | 9/2010 |
| WO | 2010/108046 A1 | 9/2010 |
| WO | 2010/125103 A1 | 11/2010 |
| WO | 2010/144785 A2 | 12/2010 |
| WO | 2010/144789 | 12/2010 |
| WO | 2011/017554 A2 | 2/2011 |
| WO | 2011/056889 A1 | 5/2011 |
| WO | 2011/082328 A1 | 7/2011 |
| WO | 2011/163272 | 12/2011 |
| WO | 2012/064892 A1 | 5/2012 |
| WO | 2012/135765 | 10/2012 |
| WO | 2012/174472 A1 | 12/2012 |
| WO | 2012/174556 A1 | 12/2012 |
| WO | 2013/016754 A1 | 2/2013 |
| WO | 2013/063160 A1 | 5/2013 |
| WO | 2014/012069 A2 | 1/2014 |
| WO | 2014/036323 A1 | 3/2014 |
| WO | 2014/066856 A1 | 5/2014 |
| WO | 2014/0144895 A1 | 9/2014 |
| WO | 2015/010092 A1 | 1/2015 |
| WO | 2015/021064 A1 | 2/2015 |
| WO | 2015/063100 A1 | 5/2015 |
| WO | 2015/148905 A1 | 10/2015 |

OTHER PUBLICATIONS

Krondahl et al., Regional differences in bioavailability of an opioid tetrapeptide in vivo rats after administration to the respiratory tract. Peptides, vol. 23, No. 3, pp. 479-488 (2002).

(56) References Cited

OTHER PUBLICATIONS

Lee et al., Intrapulmonary potential of polyethylene glycol-modified glucagon-like peptide-1s as a type 2 anti-diabetic agent. Regulatory Peptides, 152:101-107 (2009).
Selam, Jean-Louis. Inhaled Insulin: Promises and Concerns. Journal of Diabetes Science and Technology, vol. 2, Issue 2, pp. 311-315 (2008).
Shields, Irritable bowel syndrome, archived Jun. 21, 2009, available at: https://web.archive.org/web/200906211 00502/http://www.gastroenterologistpaloalto.com/conditions-diseases-irritable-bowelsyndrome-palo-alto-ca. html; cited on Aug. 26, 2015 is U.S. Appl. No. 14/139,714.
Smith et al., Evaluation of novel aerosol formulations designed for mucosal vaccination against infleunza virus. Vacine, vol. 21, pp. 2805-2812 (2003).
U.S. Appl. No. 14/873,041, filed Oct. 1, 2015.
Design U.S. Appl. No. 29/504,212, filed Oct. 2, 2014.
U.S. Appl. No. 14/774,311, filed Sep. 10, 2015.
Young et al., Encapsulation of lysozyme in a biodegradable polymer by preparation with a vapor-over-liquid antisolvent. Journal of Pharmaceutical Sciences, 88:640-650 (1999).
Hazard Prevention and Control in the Work Environment: Airborne Dust WHO/SDE/OEH/99. 14 Chapter 1—Dust: Definitions and Concepts [retrieved from internet by Examiner in European case on Sep. 22, 2015]. <URL: http://www.who.int/occupational_health/publications/airdust/en/> published on Oct. 29, 2004 as per Wayback Machine.
Owens et al., Blood glucose self-monitoring in type 1 and type 2 diabetes: reaching a multidisciplinary consensus. Diabetes and Primary Care, vol. 6, No. 1, pp. 8-16 (2004).
U.S. Appl. No. 14/863,136, filed Sep. 23, 2015.
U.S. Appl. No. 14/991,777, filed Jan. 8, 2016.
U.S. Appl. No. 14/945,168, filed Nov. 18, 2015.
Cheatham et al. "Prandial Technosphere®/Insulin inhalation provides significantly better control of meal-related glucose excursions than prandial subcutaneous insulin." Presented at the Diabetes Technology Society meeting, Oct. 2004.
Chelikani et al., Intravenous infusion of glucagon-like peptide-1 potently inhibits food intake, sham feeding, and gastric emptying in rats. Am J Physiol. Regul. Integr. Comp. Physiol., 288(6):R1695-706, 2005.
Chemical Abstracts, vol. No. 114(22), Abstract No. 214519x (1990).
Chemicaland21.com. Solvents. Dec. 12, 2008. Available from: <http://web.archive.org/web20081212035748/http://www.chemicalland21.com/info/SOLVENTS.htm.
Chow et al., Particle Engineering for Pulmonary Drug Delivery. Pharmaceutical Research, vol. 24, No. 3, pp. 411-437 (2007).
Clee et al. Nature Genetics 38:688-693, 2006.
Cobble "Initiating and Intensifying Insulin Therapy for Type 2 Diabetes: Why, When, and How." Am J Ther. Jan. 8, 2009.
Coffey et al. "Valuing heath-related quality of life in diabetes." Diabetes Care 25:2238, 2002.
Colagiuri et al., Are lower fasting plasma glucose levels at diagnosis of type 2 diabetes associated with improved outcomes? Diabetes Care, vol. 25, pp. 1410-1417 (2002).
Combettes and Kargar, C, Newly Approved and Promising Antidiabetic Agents. Therapie, Jul.-Aug. 2007: 62 (4): 293-310.
Coors et al., Polysorbate 80 in medical products and nonimmunologic anaphylactoid reactions. Ann. Allergy Astha Immunol., 95(6): 593-599 (2005).
Costello et al., "Zinc inhibition of mitochondrial aconitase and its importance in citrate metabolism in prostate epithelial cells", Journ. Biol. Chem. 272(46):28875-28881 (1997).
Cricket TM Single-Use Inhalers [on-line]. MannKind Technologies Website, posted in 2011, [retrieved on Jul. 30, 2012]. Retrieved from the Internet. <URL:mannkindtechnologies,com/DeviceTechnology/CricketSingleUseInhalers.aspx>.
Crosby, J. "Dog Normals", <http://vetmedicine.about.com/od/diseasesconditionsfaqs/tp/TP_dogfacts.htm>, copyright 2013.

Cruetzfeldt et al. "Glucagonostatic actions and reduction of fasting hyerglycemia by exogenous glucagon-like peptide i(7-36) amide in type 1 diabetic patients." Diabetes Care 19:580, 1996.
D'Alessio et al., Elimination of the action of glucagon-like peptide 1 causes an impairment of glucose tolerance after nutrient ingestion by healthy baboons. J. Clin. Invest., 97:133-38 (1996).
Database adisinsight, "Gucagon-like peptide-1 inhalation-MannKind Corporation", Database accession No. 2009:1048 Abstract.
Davis "Postprandial Physiology and the Pathogenesis of Type 2 Diabetes Mellitus." Insulin, vol. 3, Apr. 1, 2008, pp. 132-140.
De Heer et al. "Sulfonylurea compounds uncouple the glucose dependence of the insulinotropic effect of glucagon-like peptide-1." Diabetes 56:438, 2007.
Deacon "Therapeutic strategies based on glucagon-like peptide 1." Diabetes. Sep;53(9):2181-9, 2004.
Deacon et al., "Glucagon-like peptide 1 undergoes differential tissue-specific metabolism in the anesthetized pig", Am. J. Physiol. 271 (Endocrino. Metab. 34): E458-E464, 1996.
Decode study group. "Glucose tolerance and mortality: comparison of WHO and American Diabetes Association diagnostic criteria." Lancet. Aug. 21, 1999;354(9179):617-21.
DedicatedPhase, "Preclinical Trials and Research", <http://www.dedicatedphase1.com/preclinical-research.html>, copyright 2006-2011, p. 1.
Definition of analog from http://cancerweb.ncl.ac.uk/omd/about.html, pp. 1-5. Accessed by Examiner on Jul. 7, 2005 and cited in Office Action dated Jul. 26, 2013 in U.S. Appl. No. 12/830,557.
Del Prato S "Unlocking the opportunity of tight glycemic control" Diabetes Obesity and Metabolism 7:S1-S4, 2005.
Delgado-Aros et al. "Effect of GLP-1 on gastric volume, emptying, maximum volume ingested and postprandial symptoms in humans." Am J Physiol Gastrointest Liver Physiol 282:G424, 2002.
Diabetes: Counting Carbs if You Use Insulin, WedMD, http://diabetes.webmd.com/carbohydrate-counting-for-people-who-use-insulin#m Oct. 1, 2010.
Diez et al. "Inhaled insulin—a new therapeutic option in the treatment of diabetes mellitus" Expert Opin. Pharmacother, 2003, 4, 191-200.
Dorwald, F.A. Side reactions in organic synthesis. Wiley, (2005).
Doyle et al. "Glucagon-like peptide-1." Recent Prog Norm Res. 2001;56:377-99.
Dreamboat TM Reusable Inhalers [on-line]. MannKind Technologies Website, posted in 2011, Retrieved from the Internet: <URL: mannkindtechnologies.com/Device Technology/Dream Boat Reuseable Inhalers.aspx>.
Drucker "Development of glucagon-like peptide-1-based pharmaceuticals as therapeutic agents for the treatment of diabetes." Curr Pharma Design 7:1399, 2001.
Drucker et al., "The incretin system:glucagon-like peptide-1 receptor agonists and dipeptidyl peptidase-4 inhibitors in type 2 diabetes", www.thelancet.com, vol. 368, pp. 1696-1705, Nov. 11, 2006.
Drug Delivery, Easing the drug delivery route, Jun. 2006, Pharmaceutical & Medical Packaging News, Canon Communications.
Dungan et al., Glucagon-like peptide 1-based therapies for type 2 diabetes: a focus on exntadtide. Clinical Diabetes, 23: 56-62 (2005).
Dunn, "Zinc-ligand interactions modulate assembly and stability of the insulin hexamer", Biometals, 18(4):295-303 (2005).
Edelman "Type II Diabetes Mellitus." Adv Int Med, 43:449-500, 1998.
Edited by Fukushima, Masanori, "Arterial Sclerosis," Merck Manual 17th, Japanese Edition, Nikkei BP Corp., p. 1659-1663, 1999.
Edwards CMB et al. "Cardiovascular and pancreatic endocrine response to glucagon-like peptide-1(7-36) amide in the conscious calf." Exp Physiol 82:709, 1997.
Edwards CMB et al. "Subcutaneous glucagon-like peptide-1(7-36) amide is insulinotropic and can cause hypoglycaemia in fasted healthy subjects." Clinical Science 96:719, 1998.
Edwards et al., Recent advances in pulmonary drug delivery using large, porous inhaled particles. Journal of Applied Physiology, pp. 379-385 (1998).
Eggers et al., Molecular confinement influences protein structure and enhances thermal protein stability. Protein Sci., 10:250-261 (2001).

(56) References Cited

OTHER PUBLICATIONS

Ehlers et al. "Recombinant glucagon-like peptide-1 (7-36 amide) lowers fasting serum glucose in a broad spectrum of patients with type 2 diabetes." Horm Metab Res 35:611, 2003.
Eissele et al., Rat gastric somatostatin and gastrin relase: interactions of exendin-4 and truncated glucagon-like peptide-1 (GLP-1) amide. Life Sci., 55(8):629-634 (1994).
Elliot et al., Parenteral absorption of insulin from the lung in diabetic children. Austr. Paediatr. J. 23: 293-297 (1987).
Elrick et al. "Plasma insulin response to oral and intravenous glucose administration." J Clin Endocr 24:1076, 1964.
Engelgau MM "Screening for type 2 diabetes." Diabetes Care 23:1563-1580, 2000.
Engwerda et al., Improved pharmackinetic and pharmacodynamic profile of rapid-acting insulin using needle-free jet injection technology. Diabetes Care, vol. 34, Aug. 2011, pp. 1804-1808.
Erlanger et al., Phosphorous pentoxide as a reagent in peptide synthesis. College of Physicians and Surgeons—Columbia Univeristy, vol. 26, pp. 2534-2536 (1960).
Exubera indications, dosage, storage, stability. Http://www.rxlist.com/cgi/generic4/exubera_ids.htm, 2008.
Nathan DM et al. "Management of hyperglycemia in Type 2 diabetes: a consensus algorithm for the initiation and adjustment of therapy." Diabetes Care 29:1963-1972, 2006.
Nathan DM et al. "Management of hyperglycemia in Type 2 diabetes: a consensus algorithm for the initiation and adjustment of therapy." Diabetes Care 31:173-175, 2008.
Nathan DM et al. "Management of hyperglycemia in Type 2 diabetes: a consensus algorithm for the initiation and adjustment of therapy." Diabetes Care 32:193-203, 2009.
Nathan et al. "Intensive diabetes treatment and cardiovascular disease in patients with Type 1 diabetes." New Eng. J. Med. 353:2643-2653, 2005.
Nathan, "Initial Management of Glycemia in Type 2 Diabetes Melllitus" N. Eng. J. Med., 2002, 347, 1342-9.
Nauck "Is glucagon-like peptide 1 an incretin hormone?" Diabetologia 42:373-379, 1999.
Nauck et al. "Glucagon-like peptide 1 inhibition of gastric emptying outweighs its insulinotropic effects in healthy humans." Am J Physiol 273 (Endocrinol Metabl 36):E981, 1997.
Nauck et al. "Reduced incretin effect in type 2 (non-insulin-dependent) diabetes." Diabetologia 29:46-52, 1986.
Nauck et al., Effects of glucagon-like peptide 1 on counterregulatory hormone responses, cognitive functions, and insulin secretion during hyperinsulinemic, stepped hypoglycemic clamp experiments in healthy volunteers. J Clin Endocrinol Metab., 87:1239-1246, 2002.
Nauck et al., Effects of subcutaneous glucagon-like peptide 1 (GLP-1 [7-36 amide]) in patients with NIDDM. Diabetologia, 39:1546-1553, 1996.
Nauck et al., Normalization of fasting hyperglycemia by exogenous GLP-1 (7-36 amide) in type 2 diabetic patients. Diabetologia, 36:741-744, 1993.
Nemmar et al., Passage of inhaled particles into the blood circulation in humans. Circulation pp. 411-414 (2002).
Newman, Principles of metered-dose inhaler design. Respiratory Care, vol. 50, No. 9, pp. 1177-1190 (2005).
Next Generation Inhaler Nears Market, Manufacturing Chemist, Cambridge Consultants, Polygon Media Ltd. (2006).
NHS Clinical Guidelines, "Type 1 diabetes diagnosis and mangement of type 1 diabetes in children and young people", National Collaborating Centre for Women's and Children's Health Commissioned by the National Institute for Clinical Excellence, Sep. 2004, p. 1-217.
Non-covalent interactions from UC Davis ChemWiki, pp. 1-5. Accessed by Examiner on Jul. 23, 2013 and related case U.S. Appl. No. 12/830,557.
Nystrom et al. "Effects of glucagon-like peptide-1 on endothelial function in type 2 diabetic patients with stable coronary artery disease." Am J Physiol Endocrinol Metabl 287:E1209, 2004.

Oberdorster et al., Correlation between particle size, in vivo particle persistence, and lung injury. Environ Health Perspect 102 Suppl 5, pp. 173-179 (1994).
Oberdorster et al.,Pulmonary effects of inhaled ultrafine particles. International Archives of Occupational and Environmental Health, vol. 74, pp. 1-8 (2001).
Okumura et al., Intratracheal delivery of insulin: absorption from solution and aerosol by rat lung. Int. J. Pharmaceuticals 88: 63-73 (1992).
O'Neill, Air pollution and inflammation in type 2 diabetes: a mechanism for susceptibility. Occup Environ Med. vol. 54, pp. 373-379 (2007).
Orgsoltab et al., Division of Organic Chemistry. Ohio Northern University. Nov. 24, 2009. Available from: <http://www.2.onu.edu/~b-meyers/organic_solvents.html>.
Oshima et al. "Comparison of half-disappearance times, distribution volumes and metabolic clearance rates of exogenous glucagon-like peptide 1 and glucagon in rats." Regulatory Peptides 21:85, 1988.
Ostrovsky, Gene. Mannkind Inhalation Insulin Going to FDA to Seek Approval [on-line]. MedGadget.com, posted on Mar. 17, 2009, Retrieved from the Internet: <URL:http://medgadget.com/2009/03mannkind_inhalation_insulin_going_to_fda_to_seek_approval.html>.
Owens et al. "Inhaled human insulin." Nature Reviews, Drug Discovery, vol. 5, No. 5, pp. 371-372, May 2006.
Owens et al. "Alternative routes of insulin delivery." Diabetic Medicine 20:886-898, 2003.
Ozyazgan et al."Effect of glucagon-like peptide-1)7-36) and exendin-4 on the vascular reactivity in streptozotocin/nicotinamide-induced diabetic rats." Pharmacology 74:119, 2005.
Pacini P, Marino MT. Evaluation of endogenous and exogenous components to peripheral insulin concentration during administration of inhaled insulin. ADA 2010; Abstract 2094-PO.
Patton "Mechanisms of macromolecule absorption by the lungs." Advanced Drug Delivery Reviews 19:3, 1996.
Patton "Unlocking the opportunity of tight glycaemic control. Innovative delivery of insulin via the lung." Diabeters Obesity and Metabolism 7:S5, 2005.
Patton & Platz, Routes of Delivery: Case studies: plumonary delivery of peptides and proteins for systemic action. Adv. Drug. Del. Rev. 8: 179-196 (1992).
Patton et al. "The lungs as a portal of entry for systemic drug delivery." Proc Am Thorac Soc 1:338, 2004.
Patton et al. "Clinical pharmacokinetics and pharmacodynamics of inhaled insulin." Clin Pharmacokinet 43:781-801, 2004.
Patton et al., "Inhaled Insulin", Advanced Drug Delivery Reviews, 35, Feb. 1999, p. 235-247.
Onoue et al., Dry powder inhalation systems for pulmonary delivery of therapeutic peptides and proteins. Expert Opin. Ther. Patents 18(4):429-442 (2008).
Pearson et al., Systematically Initiating Insulin, supplemental to vol. 32, No. 1, 19S-28S, 2006.
Perera et al. "Absorption and Metabolic Effect of Inhaled Insulin." Diabetes Care, vol. 25, No. 12, Dec. 2002, p. 2276-2281.
Pesic, Inhaler delivers more drug to the deep lung, says Cambridge Consultants. in-Pharma Technologist.com, http://www/in-pharmatechnologist.com/content/view/print/344335, Dec. 1, 2010.
Petkowicz et al., "Hypoglycemic effect of liposome-entrapped insulin adminstered by various routes into normal rats", Pol. J. Pharmacol. Pharm. 41:299-304 (1989).
Petrucci R, Amin N, Lovertin P. et al. Pulmonary function tests remain similar in patients who received Technosphere® insulin and in patients currently receiving standard antidiabetic therapy. Diabetologia 2009; 52 (suppl 1).
Peyrot et al. "Resistance to insulin therapy among patients and providers." Diabetes Care 28:2673-2679, 2005.
Peyrot M, Rubin RR, Otterbach K. Effect of Technosphere® inhaled insulin on treatment satisfaction, glycemic control and quality of life. Diabetes 2006; 55:Abstract 423-P.
Pezron et al., Insulin aggregation and asymmetric transport across human bronchial epithelial cell monolayers (Calu-3). J. Pharmaceutical Sci. 91: 1135-1146 (2002).

(56) References Cited

OTHER PUBLICATIONS

Pfeiffer MA et al. Insulin secretion in diabetes mellitus. Am J Med 70:579-88, 1981.
Pfutzner et al., Abstract 812: Influence of small dose i.v.s.c. and pulmonary insulin treatment on grandial glucose control in patients with type 2 diabetes. Internet Article [Online] 2001, 37th Annual Meeting of the EASD, Glasgow, Sep. 9-13, 2001.
Pfutzner A et al. "Pulmonary insulin delivery by means of the Technosphere(TM) drug carrier mechanism." Expert Opin Drug Deliv 2:1097-1106, 2005.
Pfützner A et al. "Technosphere®/Insulin—a new approach for effective delivery of human insulin via the pulmonary route." Diab Tech Ther 4:589-594, 2002.
Pfützner A et al. "Lung distribution of radiolabeled Technosphere™/Insulin." Diabetes 52 Supplement, Jun. 2003, A107.
Pfützner A et al. Pilot study with Technosphere/PTH(1-34)—a new approach for effective pulmonary delivery of parathyroid hormone (1-34). Horm Metab Res 35:319-323, 2003.
Pfützner A et al. "Variability of insulin absorption after subcutaneous and pulmonary application in patients with type 2 diabetes." Diabetes 51 Supplement, Jun. 2002, A47-48.
Pfutzner et al. "Inhaled Technosphere/Insulin Shows a Low Variability in Metabolic Action in Type 2 Diabetic Patients." Diabetes 49 Supplement, May 2000, A121.
Pfuetzner A, Rave K, Heise T, et al. Inhaled Technosphere™/insulin results in low variability in metabolic action in type 2 diabetic patients. Exp Clin Endocrinol Diabetes 2000; 108:S161.
Pfuetzner A, Rave K, Heise T, et al. Low variability in metabolic action in type 2 diabetic patients with inhaled Technosphere/insulin. Diabetologia 2000; 43:Abstract 774.
Phillips M, Amin N, Boss AH, et al. Pulmonary functions (over 2 years) in diabetic subjects treated with Technosphere® insulin or usual antidiabetic treatment. Diabetologia 2009; 52 (suppl 1).
Pohl R, Muggenberg BA, Wilson BR, et al. A dog model as predictor of the temporal properties of pulmonary Technosphere/insulin in humans. Respiratory Drug Delivery 2000; VII: 463-465.
Polonsky et al. "Abnormal Patterns of Insulin Secretion in Non-insulin-Dependent Diabetes Mellitus." N Eng J Med 318:1231-39, 1988.
Potocka E, Amin N, Cassidy J, et al. Insulin pharmacokinetics following dosing with Technosphere® insulin in subjects with chronic obstructive pulmonary disease. Current Medical Research and Opinion 2010; 26:2347-2353.
Potpcka E, Baughman RA, Derendorf H. Population pharmacokinetic model of human insulin following different routes of administration. Journal of Clinical Pharmacology 2011;51:1015-1024.
Potocka E, Baughman R, Derendorf H. Population Pharmacokinetic Model of Regular Human Insulin Following Different Routes of Administration. AAPS Journal. 2009; 11(S1). Available from: http://www.aapsj.org. Presented at the 2009 AAPS (American Association of Pharmaceutical Scientists) National Biotechnology Conference, Jun. 21-24, Seattle, WA.
Potocka E, Baughman RA, Derendorf J. A population PK/PD model of Technosphere® insulin administered to healthy and type 2 diabetics. ADA 2010; Poster 624.
Potocka E, Baughman RA, Schwartz SL, et al. Pharmacokinetics of AFRESA® unchanged in patients with chronic obstructive pulmonary function ADA 2009; Poster 437.
Potocka E, Cassidy J P, Haworth P, et al. Pharmacokinetic characterization of the novel pulmonary delivery excipient fumaryl diketopiperazine. Journal of diabetes science and technology 2010;4:1164-1173.
Potocka E, Cassidy JP, Haworth P, et al. Pharmacokinetic characterization of fumaryl diketopiperazine. Third International Conference on Advanced Technologies and Treatments for Diabetes 2010; Poster 291.
Potocka E, Hovorka R, Baughman R, et al. Characterization of metabolism parameters following Technosphere® insulin and insulin Lispro. ADA 2010; Poster 1561.
Potocka E, Hovorka R, Baughman RA, et al. Afresa™ supresses endogenous glucose production earlier than a rapid-acting analog (Lispro) and inhaled Exubera® ADA 2009; Oral 232.
Potocka E, Hovorka R, Baughman RA, et al. Technosphere® insulin suppresses endogenous glucose production earlier than a rapid-acting analog (lispro) and an inhaled insulin (exubera). Diabetologia 2009; 52 (suppl 1).
Prabhu et al. "A study of factors controlling dissolution kinetic of zinc complexed protein suspensions in various ionic species", Int. J. Pharm. 217(1-2):71-8 (2001).
Laube et al., The lung as an alternative route for delivery for insulin in controlling postrprandial glucose levels in patients with diabetes. Chest, Preliminary Report 114 (6) : 1734-1739 (1998).
Quattrin et al. "Efficacy and Safety of Inhaled Insulin (Exubera) Compared with Subcutaneous Insulin Therapy in Patients with Type 1 Diabetes." Diabetes Care, vol. 27, No. 11, Nov. 2004, p. 2622-2627.
Quddusi et al. "Differential effects of acute and extended infusions of glucagon-like peptide-1 on first- and second-phase insulin secretion in diabetic and nondiabetic humans." Diabetes Care 26:791, 2003.
Rachman et al. "Normalization of insulin responses to glucose by overnight infusion of glucagon-like peptide 1 (7-36) amide in patients with NIDDM." Diabetes 45:1524, 1996.
Raju et al., Naseseazines A and B: a new dimeric diketopiperazine framework from a marine-derived actinomycete, *Streptomyces* sp. Organic letters, vol. 11, No. 17, pp. 3862-3865 (2009).
Raskin et al. "Continuous subcutaneous insulin infusion and multiple daily injection therapy are equally effective in type 2 diabetes." Diabetes Care, vol. 26, No. 9, pp. 2598-2603, Sep. 2003.
Raskin P, Heller S, Honka M, et al. Pulmonary function over 2 years in diabetic patients treated with prandial inhaled Technosphere® Insulin or usual antidiabetes treatment: A randomized trial. Diabetes, Obesity and Metabolism 2012;14:163-173.
Raskin P, Phillips M, Amin N, et al. Hypoglycemia in patients with type 1 diabetes incorporating prandial inhaled Technosphere® insulin into their usual diabetes treatment regimen vs continuing their usual diabetes management. AACE 2010; Poster 283.
Raskin P, Phillips MD, Rossiter A, et al. A1C and hypoglycemia in patients with type 2 diabetes mellitus incorporating prandial inhaled Technosphere® insulin into their usual antihyperglycemic regimen vs continuing their usual antihyperglycemic regimen. ADA 2010; Abstract 359-OR.
Raufman et al., Exendin-3, a novel peptdie from Heloderma horridum venom, interacts with vasoactive intestinal peptide receptors and a newly described receptor on dispersed aciin from guinea pig pancreas. J. Biol. Chem. 266(5) : 2897-2902 (1991).
Raufman et al., Truncated glucagon-like peptide-1 interacts with exendin receptors on dispersed acini from guina pig pancreas. J. Biol. Chem. 267(30) : 21432-21437 (1992).
Raun et al. "Liraglutide, a long-acting glucagon-like peptide-1 analog, reduces body weight and food intake in obese candy-fed rats, where as a dipeptidyl peptidase-IV inhibitor, vildagliptin, does not." Diabetes 56:8, 2007.
Rave et al. "Coverage of Postprandial Blood Glucose Excursions with Inhaled Technosphere Insulin in Comparison to Subcutaneously Injected Regular Human Insulin in Subjects with Type 2 Diabetes." Diabetes Care, vol. 30, No. 9, pp. 2307-2308, Sep. 2007.
Rave et al. "Dose Response of Inhaled Dry-Powder Insulin and Dose Equivalence to Subcutaneous Insulin Lispro." Diabetes Care 28:2400-2405, 2005.
Rave et al. "Inhaled Technosphere Insulin in Comparison to Subcutaneous Regular Human Insulin: Time Action Profile and Variability in Subjects with Type 2 Diabetes." Journal of Diabetes Science and Technology, vol. 2, Issue 2, pp. 205-212, Mar. 2008.
Rave et al. "Results of a Dose-Response Study with a New Pulmonary Insulin Formulation and Inhaler." Diabetes 49, Supplement, May 2000, A75.
Rave et al. "Time-action profile of inhaled insulin in comparison with subcutaneously injected insulin lispro and regular human insulin." Diabetes Care 28:1077, 2005.

(56) References Cited

OTHER PUBLICATIONS

Rave K, Heise T, Pfuetzner A, et al. Assessment of dose-response characteristics for a new pulmonary insulin formulation and inhaler. Exp Clin Endocrinol Diabetes 2000; 108:S161.
Rave K, Potocka E, Boss AH, et al. Pharmacokinetics and linear exposure of Afresa™ compared with the subcutaneous injection of regular human insulin Diabetes, Obesity and Metabolism 2009; 11:715-720.
Raz et al. "Pharmacodynamics and Pharmacokinetics of Dose Ranging Effects of Oralin versus S.C. Regular Insulin in Type 1 Diabetic Patients." Fourth Annual Diabetes Technology Meeting, Philadelphia PA, 2004.
Razavi et al. "TRPVI+ sensory neurons control beta cell stress and islet inflammation in autoimmune disease." Cell 127:1123, 2006.
Retrieved from website: http://groups.molbiosci.northwestern.edu/holmgren/Glossary/Definitions/Def-P/placebo.html, 1 page, Retrieved on Mar. 12, 2013.
Rhodes et al. "Technosphere: Microspherical Particles from Substituted Diketopiperazines for Use in Oral Drug Delivery." 208th ACS National Meeting, Aug. 1994.
Richardson et al. "Technosphere Insulin Technology." Diabetes Technology & Therapeutics, vol. 9, Supplement 1, pp. S65-S72, 2007.
Richardson PC, Potocka E, Baughman RA, et al. Pharmacokinetics of Technosphere® insulin unchanged in patients with chronic obstructive pulmonary disease. Diabetologia 2009; 52 (suppl 1).
Richter et al. "Characterization of glucagon-like peptide-1(7-36)amide receptors of rat membranes by covalent aross-linking." FEBS Letters 280:247, 1991.
Richter et al. "Characterization of receptors for glucagon-like peptide-1 (7-36)amide on rat lung membranes." FEBS Letters 267:78, 1990.
Riddle "Combining Sulfonylureas and Other Oral Agents." Am J Med, 2000, vol. 108(6A), pp. 15S-22S.
Riddle et al. "Emerging therapies mimicking the effects of amylin and glucagon-like peptide 1." Diabetes Care 29:435, 2006.
Ritzel et al. "Pharmacokinetic, insulinotropic, and glucagonostatic properties of GLP-1 (7-36 amide) after subcutaneous injection in healthy volunteers. Dose-response-relationships." Diabetologia 38:720, 1995.
Rosen et al., Substance P microinjected into the periaqueductal gray matter induces antinociception and is released folloing morphine administration. Brain Research, 1001: 87-94 (2004).
Rosenmund et al., Diketopiperazines from Leuchs Anhydrides. Angew Chem Intern. Edit. vol. , No. 2 (1970).
Rosenstock "Dual therapy with inhaled human insulin (Exubera(R)) as add-on to metformin (with stopping sulfonurea) is better than triple therapy with rosiglitazone add-on to combination metformin and sulfonurea in poorly controlled Type 2 diabetes." Diabetes 57:supplement 1:A557, Abstract 2018-PO, 2008.
Chan et al., Physical stability of salmon calcitonin spray-dried powders for inhalation. Journal of Pharmaceutical Sciences, vol. 93, No. 3, pp. 792-804 (2004).
Fabio et al., Heat-stable dry powder oxytocin formulations or delivery by oral inhalation. AAPS PharmSciTech, (2015).
Kim et al., Dose-response relationships of inhaled insulin delivered via the aerodose insulin inhaler and subcutaneously injected insulin in patients with type 2 diabetes. Diabetes Care, 26:2842-2847 (2003).
Klonoff, David C. M.D., Afrezza inahled insulin: the fastest-acting FDA-approved insulin on the market has favorable properties. Journal of Diabetes Science and Technology, vol. 8(6): 10-71-1073 (2014).
Sarala et al., Technosphere: New drug delivery system for inhaled insulin. Future Prescriber, vol. 13, No. 1, pp. 14-16 (2012).
U.S. Appl. No. 15/300,239, filed Sep. 28, 2016.
Mumenthaler et al., Feasibility study on spray-drying protein pharmaceuticals: recombinant human growth hormone and tissue-type plasminogen activator. Pharm Res., 11(1):12-20 (1994).
U.S. Appl. No. 15/377,641, filed Dec. 13, 2016.

Uwaifo et al., Novel pharmocologic agents for type 2 diabetes. Endocrinology and Metabolism Clinics of North America, vol. 34, No. 1, pp. 155-197 (2005).
Xi-de Tu, et al. Pharmaceutics. Oct. 2002, 3rd edition, second printing, p. 905.
Design U.S. Appl. No. 29/553,300, filed Jan. 29, 2016.
Design U.S. Appl. No. 29/553,303, filed Jan. 29, 2016.
Design U.S. Appl. No. 29/553,302, filed Jan. 29, 2016.
Design U.S. Appl. No. 29/553,305, filed Jan. 29, 2016.
Lane et al., Influence of post-emulsification drying processes on the microencapsulation of Human Serum Albumin. International Journal of Pharmaceutics, 307: 16-22 (2006).
Exubera package insert, p. 1, 2008.
Fadl et al., Effects of MDI spray angle on aerosol penetration efficiency through an oral airway cast. Journal of Aerosol Science, vol. 38, No. 8, pp. 853-864 (2007).
Falsone et al., The Biginelli dihydropyrimidone synthesis using polyphosphate ester as a mild and efficient cyclocondensation/dehydration reagent. Institute of Chemistry, Organic and Bioorganic Chemistry, Karl-Franzens-University, pp. 122-134 (2001).
Farr, S.J. et al., Pulmonary insulin administration using the AERx®system:physiological and physiochemical factors: influencing insulin effectiveness in healthy fasting subjects. Diabetes Tech. Ther. 2:185-197, 2000.
Fehmann et al. "Cell and molecular biology of the incretin hormones glucagon-like peptide-1 and glucose-dependent insulin releasing polypeptide." Endocrine Reviews 16:390, 1995.
Ferrin et al, Pulmonary retention of ultrafine and tine particles in rats. Am. J. Repir. Cell Mol. Biol., pp. 535-542 (1992).
Festa et al., "LDL particle size in relation to insulin, proinsulin, and insulin sensitivity" Diabetes Care, 22 (10):1688-1693 (1999).
Forst et al., "Metabolic Effects of Mealtime Insulin Lispro in Comparison to Glibenclamide in Early Type 2 Diabetes", Exp. Clin. Endocrinol. Diabetes, 2003, 111, 97-103.
Fritsche et al. "Glimepiride Combined with Morning Insulin Glargine, Bedtime Neutral Protamine Hagedorm Insulin, or Bedtime Insulin Glargine in Patients with Type 2 Diabetes." American College of Physicians 2003.
Galinsky et al., A synthesis of diketopiperazine's using polyphosphoric acid. Journal of the American Pharmaceutical Association, vol. 46, No. 7, pp. 391-393 (1957).
Garber, "Premixed insulin analogues for the treatment of diabetes mellitus", Drugs, 66(1):31-49 (2006).
Garg et al. "Improved glycemic control without an increase in severe hypoglycemic episodes in intensively treated patients with type 1 diabetes receiving morning, evening, or split dose insulin glargine." Diabetes Research and Clinical Practice 66 (2004) 49-56.
Garg SK, Kelly W, Freson B, et al. Treat-to-target Technosphere® insulin in patients with type 1 diabetes. ADA 2011; Abstract 941-P.
Garg SK, McGill JB, Rosenstock J, et al. Technosphere® insulin vs insulin lispro in patients with type 1 diabetes using multiple daily injections. ADA, Abstract 917-P (2011).
Gates BJ "Update on advances in alternative insulin therapy." Advances in Pharmacy 1:159-168, 2003.
Glucagon for Injection (1999) glucagon for injection (rDNA origin), pp. 1-7.
Glucagon-like peptide-1; http://en.wikipedia.org/wiki/Glucagon-like peptide-1 (accessed Apr. 24, 2015).
Glucophage Product Insert. Jan. 2009.
Glucotrol Product Insert. Sep. 2006.
Gnudi L, Lorber D, Rosenstock J, et al. Basal/bolus with prandial inhaled Technosphere® insulin (TI) plus insulin glargine qd vs biaspart 70/30 insulin bid in type T2 diabetes mellitus inadequately controlled on insulin with/without oral agents. Diabetologia 2009; 52 (suppl 1).
Goke et al., Exendin-4 is a high potency agonist and truncated exendin-(9-39)-amide an antagonist at the glucagon-like peptide 1-(7-36)-amide receptor of insulin-secreting beta-cells. J. Biol. Chem. 268(26):19650-19655 (1993).
Golpon et al. "Vasorelaxant effect of glucagon-like peptide-(7-36) amide and amylin on the pulmonary circulation of the rat." Regulatory Peptides 102:81, 2001.

(56) References Cited

OTHER PUBLICATIONS

Gonzalez et al., Actualizacion del tratamiento farmacologico de la diabetes mellitus tipo 2. Del Sistema Nacional de Salud. vol. 32, No. 1, pp. 3-16 (2008)—full article in Spanish with English abstract.
Gotfried M, Cassidy JP, Marino MT, et al. Lung deposition and absorption of insulin from Technosphere® insulin. Diabetologia 2009; 52 (suppl 1).
Grant et al "Both insulin sensitivity and maximal glucose elimination rate are reduced in type 2 diabetes." Presented at the American Diabetes Association 65th Scientific Sessions, Jun. 2005, abstract 2202-PO.
Grant et al. "The distribution of 14C-labeled particles following intra-tracheal liquid installation in the Sprague-Dawley rat." Presented at the American Diabetes Association 64th Scientific Sessions, Jun. 2004, abstract 461-P.
Grant M, Harris E, Leone-Bay A, Rousseau K. Technosphere®/insulin: Method of action. Diabetes Technology Meeting 2006; Poster.
Grant ML, Greene S, Stowell GW, et al. Mimicking endogenous peptide secretion by inhalation APS 2009; poster.
Greene et al. "Effects of GLP-1 Technosphere(TM) powder: administered by pulmonary insufflation in male obese Zucker diabetic fat (ZDF) rats." Diabetes Technology Meeting, San Francisco, Oct. 2007.
Greene et al., Greene's protective groups in organic synthesis. 4th ed., pp. 781-783 (2007).
Gupta et al. "Contemporary Approaches in Aerosolized Drug Delivery to the Lung." J. Controlled Research, 17:129-148, 1991.
Gurrieri et al., Thermal condensation of some alpha-aminoacids with phatalic acid. Thermochimica Acta, 7 (1973) 231-239.
Gutniak et al. "Antidiabetogenic action of glucagon-like peptide-1 related to administration relative to meal intake in subjects with type 2 diabetes." J Int Med 250:81, 2001.
Gutniak et al. "Antidiabetogenic effect of glucagon-like peptide-1 (7-36)amide in normal subjects and patients with diabetes mellitus." NEJM 326:1316, 1992.
Gutniak et al. "GLP-1 tablet in type 2 diabetes in fasting and postprandial conditions." Diabetes Care 20:1874, 1997.
Gutniak et al. "Potential therapeutic levels of glucagon-like peptide I achieved in humans by a buccal tablet." Diabetes Care 19:843, 1996.
Gutniak et al. "Subcutaneious injection of the incretin hormone glucagon-like peptide 1 abolishes postprandial glycemia in NIDDM." Diabetes Care 17:1039, 1994.
Guyton et al., "Acute Control of Llocal Blood Flow", Textbook of Medical Physiology, Chapter 17, 10th Edition, W.B. Saunders Company, pp. 176-177, 2000.
Gyore et al., Thermal Analysis, vol. 2—Proceedding Fourth ICTA Budapest 1974; 387-394.
Haak "New developments in the treatment of type 1 diabetes mellitus." Exp Clin Endocrinol Diabetes 107:Suppl 3: S108, 1999.
Haffner et al., "Proinsulin and insulin concentrations I relation to carotid wall thickness", Strock 29:1498-1503 (1998).
Hagedorn et al. "Protamine Insulin", JAMA, 106:177-180 (1936).
Haino, Takeharu et al. "On-beads Screening of Solid-Attached Diketopiperzines for Calix[5]Arene-Based Receptor." Tetrahedron Letters, 40(20), 3889-3892, 2003.
Halozyme Press Release. Jun. 6, 2009.
Hanley et al., "Cross-sectional and prospective associations between proinsulin and cardovascular disease risk factors in a population experiencing rapid cultural transition" Diabetes Care 24(7): 1240-1247 (2001).
Harsch IA "Inhaled insulins. Their potential in the treatment of diabetes mellitus." Traat. Endicrinol 4:131-138, 2005.
Hassan et al. "A Randomized, Controlled Trial Comparing Twice-a-Day Insulin Glargine Mixed with Rapid-Acting Insulin Analogs Versus Standard Neutral Protamine Hagedom (NPH) Therapy in Newly Diagnosed Type 1 Diabetes." Pediatrics, 121(3), e466-e472, 2008.
Hassan et al. "In vivo dynamic distribution of 131l-glucagonOlike peptide-1 (7-36) amide in the rat studied by gamma camera." Nucl Med Biol 26:413, 1999.
Hausmann et al. "Inhaled insulin as adjunctive therapy in subjects with type 2 diabetes failing oral agents: a controlled proof of concept study." Diabetes Obesity and Metabolism 8:574, 2006.
Hayasaka et al. "Proliferation of type II pneumocytes and alteration in their apical surface membrane antigenicity in pulmonary sarcoidosis." Chest 116:477, 1999.
Standl et al. "Good Glycemic Control With Flexibility in Timing of Basal Insulin Supply." Diabetes Care, vol. 28, No. 2, Feb. 2005.
Stanley et al. "Gastrointestinal satiety signals III. Glucagon-like peptide 1, oxyntomodulin, peptide YY and pacretic peptide." Am J Physiol Gastrointest Liver Physiol 286:G693, 2004.
Steinberg et al. "A new approach to the safety assessment of pharmaceutical excipients." Reg Toxicol Pharmacol 24:149, 1996.
Steiner et al. "A novel glucagon delivery system for the management of hyperinsulinemia." Diabetes 49 Supplement 1, Abstract 1545-PO, A368, 2000.
Steiner et al. "Bioavailability and pharmacokinetic properties of inhaled dry powder Technosphere®/Insulin" Diabetes 49 Supplement, May 2000, A126.
Steiner et al. "Technosphere®, a novel drug delivery system for oral administration of calcitonin." Pharmaceutical Res 11:S299, 1994.
Steiner et al. Technosphere(TM)/Insulin—proof of concept study with a new insulin formulation for pulmonary delivery. Exp Clin Endocrinol Diabetes, 110:17-21, 2002.
Steiner, K. et al. "The relative importance of first- and second-phase insulin secretion in countering the action of glucagon on glucose turnover in the conscious dog." Diabetes 31:964-972, 1982.
Steiner S, Rave K, Heise T, et al. Pharmacokinetic properties and bioavailablility of inhaled drug powder Technosphere™/insulin. Exp Clin Endocrinol Diabetes 2000; 108:S161.
Steiner S, Rave K, Heise T, et al. Technosphere™/insulin: Bioavailability and pharmacokinetic properties in healthy volunteers. Diabetologia 2000;43:Abstract 511-P.
Steiner SS, Burrell BB, Feldstein R, et Al. Pulmonary delivery of Technosphere™/insulin: Increased bioefficacy and bioavailability in clinical trials using the PDC Medtone™ inhaler. Proceed Int'l Symp Control Rel Bioact Mater 2000; 27:1000-1001.
Stowell et al. "Development of GLP-1 Technosphere(TM) powder: an inhaled GLP-1 product." Diabetes Technology Meeting, San Francisco, Oct. 2007.
Strack "Inhaled Human Insulin." Drugs of Today 2006, 42 (4): 207-221.
Sturis et al., GLP-1 deriative liraglutide in rats with beta-cell deficiences: influence of metabolic state on beta-cell mass dynamics. British Journal of Pharmacology, 140: 123-132 (2003).
Svartengren et al., Added External Resistance Reduces Oropharyngeal Deposition and Increases Lung Deposition of Aerosol Particles in Asthmatics. Am. J. Respir. Grit. Care Med., vol. 152, pp. 32-37, 1995.
Sympatecs. Dry Dispersion for Laser Diffraction and Image Analysis, 2011. XP-002586530.
Leone-Bay et al., Innovation in drug delivery by inhalation. Ondrugdelivery, No. 7, pp. 4-8 (2010).
Tack CJ, Boss AH, Baughman RA, et al. A randomized, double blind, placebo controlled study of the forced titration of prandial Technosphere®/Insulin in patients with type 2 diabetes mellitus. Diabetes 2006;55:Abstract 428-P.
Tack CJ, Christov V, deGalan BE, et al. Randomized forced titration to different doses of Technosphere® insulin demonstrates reduction in postprandial glucose excursions and hemoglobin A1c in patients with type 2 diabetes. J Diabetes Sci Technol 2008; 2(1) :47-57.
Tang-Christensen et al. "Central administration of GLP-1-(7-36) amide inhibits food and water intake in rats." Am J Physiol 271 (Regulatory Integrative Comp Physiol 40):R848, 1996.
Taylor et al. "Aerosols for macromolecule delivery. Design challenges and solutions." Am J Drug Deliv 2:143-155, 2004.
Teeter et al. "Dissociation of lung function changes with humoral immunity during inhaled human insulin therapy." Am J Resp Crit Care Med 173:1194, 2006.

(56) References Cited

OTHER PUBLICATIONS

Telko et al., Dry Powder Inhaler Formulation. Respiratory Care, Sep. 2005, vol. 50, No. 9, 1209-1227.
The American Diabetes Association "Insulin Administration" Diabetes Care, vol. 27, Supplement 1, S106-S109 (2004).
Gerber et al., Treatment satisfaction with inhaled insulin in patients with type 1 diabetes. Diabetes Care 24:1556-1559 (2001).
The Lancet. 1989, vol. 333, p. 1235-1236.
Thorens "Expression cloning of the pancreatic b-cell receptor for the gluco-incretin hormone glucagon-like peptide-1." PNAS 89:8641, 1992.
Thorens B et al. "Cloning and function expression of the human islet GLP-1 receptor: demonstration that exendin-4 is an agonist and exendin-(9-39) an antagonist of the receptor." Diabetes 42:1678, 1993.
Todd et al. "Glucagon-like peptide-1 (GLP-1: a trial of treatment in non-insulin-dependent diabetes mellitus." Eur J Clin Invest 27:533, 1997.
Todd et al. Subcutaneous glucagon-like peptide-1 improves postprandial glucaemic control over a 3-week period in patients with early type 2 diabetes. Clinical Science 95:325, 1998.
Toft-Nielson et al. "Determinants of the effectiveness of glucagon-like peptide-1 in type 2 diabetes." J Clin Endocrinol Metab 86:3853, 2001.
Toft-Nielson et al. "Exaggerated secretion of glucagon-like peptide-1 (GLP-1) could cause reactive hypoglcaemia." Diabetologia 41:1180, 1998.
Toft-Nielson et al. "The effect of glucagon-like peptide-1 (GLP-1) on glucose elimination in healthy subjects depends on the pancreatic glucoregulatory hormones" Diabetes 45:552, 1996.
Tornusciolo D.R. et al., Biotechniques 19(5):800-805, 1995. Simultaneous detection of TDT-mediated dUTP-biotin nick end-labeling (TUNEL)-positive cells and multiple immunohistochemical markers in single tissue sections.
Triantafyllidis et al., Structural, compositional and acidic characteristics of nanosized amorphous or partially crystalline ZSM-5 zeolite based materials. Microporous and Mesoporous Materials, 75:89-100 (2004).
Tu N, Kramer DA, Baughman RA. Inhaled Technosphere® Insulin improves glycemic control without weight gain. Diabetes 2007;56:Abstract 471-P.
Tuley et al., Experimental observations of dry powder inhaler dose fluidisation. International Journal of Pharmaceutics, 358, pp. 238-247 (2007).
Utah Valley University. Saponification. © 2009. Available from: <http://science.uvu.edu/ochem/index.php/alphabetical/s-t/saponification/printpage/>.
Vaczek, Accelerating drug delivery firms exploring new drug-delivery routes and devices intently awaiting the commmercial launch of Exubera. Pharmaceutical & Medical Packaging News, vol. 14, No. 6 (2006).
Vahl et al. "Effects of GLP-1-(7-36)NH2, GLP-1-(7-37), and GLP-1-(9-36)NH2 on intravenous glucose tolerance and glucose-induced insulin secretion in healthy humans." J Clin Endocrinol Metabol 88:1772, 2003.
Van Alfen-Van Der Velden et al. "Successful treatment of severe subcutaneou insulin resistance with inhaled insulin therapy", Pediatric Diabetes 2010: 11:380-382.
Vara E et al. "Glucagon-like peptide-1 (7-36) amide stimulates surfactant secretion in human type II pneumocytes." Am J Resp Crit Care Med 163:840-846, 2001.
Vella A et al. "Effect of glucagon-like peptide 1(7-36) amide on glucose effectiveness and insulin action in people with type 2 diabetes." Diabetes 49:611, 2000.
Vella A et al. "The gastrointestinal tract and glucose tolerance." Curr Opin Clin Nutr Metab Care 7:479, 2004.
Vendrame et al. "Prediabetes: prediction and prevention trials." Endocrinol Metab Clin N Am, 2004, vol. 33, pp. 75-92.

Verdich C, et al., A meta-analysis of the effect of glucagon-like peptide-1 (7-36) amide on ad libitum energy intake in humans. J Clin Endocrinol Metab., 86:4382-4389, 2001.
Vilsboll et al. "Reduced postprandial concentrations of intact biologically active glucagon-like peptide-1 in type 2 diabetic patients." Diabetes 50:609, 2001.
Vilsboll et al. "Similar elimination rates of glucagon-like peptide-1 in obese type 2 diabetic patients and healthy subjects." J Clin Endocrinol Metab 88:220, 2003.
Vilsboll et al., "Evaluation of β-Cell Secretary Capacity Using Glucagon-Like Peptide 1", Diabetes Care, vol. 23, No. 6, pp. 807-812, Jun. 2000.
Vilsboll et al., "Incretin secretion in Relation to Meal Size and Body Weight in Healthy Subjects and People with Type 1 and Type 2 diabetes Mellitus", The Journal of Clinical Endrocronology & Metabolism, vol. 88, No. 6, pp. 2706-2713, 2003.
Amorij et al., Development of stable infleunza vaccine powder formulations challenges and possibilities. Pharmaceutical Research, vol. 25, No. 6, pp. 1256-1273 (2008).
Audouy et al., Development of a dried influenza whole inactivated virus vaccine for pulmonary immunization. Vaccine, vol. 29, pp. 4345-4352 (2011).
Volund "Conversion of insulin units to SI units." American Journal of Clinical Nutrition, Nov. 1993, 58(5), pp. 714-715.
Wachters-Hagedoorn et al. "The rate of intestinal glucose absorption is correlated with plasma glucose-dependent insulinotropic polypeptide concentrations in healthy men." J Nutr 136:1511, 2006.
Wang et al., Glucagon-like peptide-1 is a physiological incretin in rat. J. Clin. Invest., 95 : 417-421 (1995).
Wang et al., Glucagon-like peptide-1 regulates proliferation and apoptosis via activation of protein kinase B in pancreatic INS-1 beta cells. Diabetologia, 47:478-487, 2004.
Wareham et al., "Fasting Proinsulin Concentrations Predict the Development of Type 2 Diabetes", Diabetes Care, 1999, 22, 262-70.
Warren et al. "Postprandial versus prandial dosing of biphasic insulin aspart in elderly type 2 diabetes patients." Diabetes Res Clin Pract 66:23-29, 2004.
Waterhouse et al., "Comparatie assessment of a new breath-actuated inhaler in patients with reversible airways obstruction", Respiration 59:155-158 (1992).
WebMD (retrieved from http://www.webmd.com/pain-management/tc/pain-management-side-effects-of-pain-medicines in 2012, 4 pages).
Wei et al. "Tissue-specific expression of the human receptor for glucagon-like peptide-1: brain and pancreatic forms have the same deduced amino acid sequence." FEBS Letters 358:219, 1995.
Weir et al. "Glucagonlike peptide 1 (7-37) actions on endocrine pancreas." Diabetes 38:338, 1989.
Weiss, SR et al. "Inhaled insulin provides improved glycemic control in patients with type 2 diabetes mellitus inadequately controlled with oral agents." Arch Intern Med 163:2277-2282, 2003.
Weissberger, "Mannkind: Overlooked Biotech with Excellent Prospects (Part V)," http://www.investorvillage.com/smbd.asp?mb=28858&mn=45817&pt=msg&mid=5021385 (posted on Jun. 19, 2008, accessed on Oct. 18, 2012).
West, Solid State Chemistry and its Applications, Chp 10, Solid Solutions. Wiley, New York, 358 (1998).
Wettergren A et al. "Truncated GLP-1 (proglucagon 78-107-Amide) inhibits gastric and pancreatic functions in man." Digestive Diseases and Sciences 38:665, 1993.
White JR et al. "Inhaled insulin: an overview." Clinical Diabetes 19:13-16, 2001.
Wigley et al., Insulin across respiratory mucosae by aerosol delivery. Diabetes 20(8): 552-556 (1971).
Willms B et al. "Gastric emptying, glucose responses, and insulin secretion after a liquid test meal: effects of exogenous glucagon-like peptide-1 (GLP-1)-(7-36) amide in type 2 (noninsulin-dependent) diabetic patients." J. Clin Endocrinol Metab 81:327, 1996.
Wilson BR et al. "Technospheres(TM) for pulmonary and nasal applications." Respiratory Drug Delivery VIII, 2002,p. 545.
Wilson et al., Spray-drying, a viable technosphere formulation process option to lyophilization, http://www.aapsj.org/abstracts/AM_2004/AAPS2004-002724.PDF, 1 page, 2004.

(56) References Cited

OTHER PUBLICATIONS

Witchert, Low molecular weight PLA: A suitable polymer for pulmonary administered microparticles. J. Microencapsulation, 10(2): 195-207 (1993).
Wright et al., Inhaled Insulin: Breathing new life into diabetes therapy. Nursing, vol. 37, No. 1, p. 46-48 (2007).
Wong et al. "From cradle to grave: pancreatic b-cell mass and glucagon-like peptide-1." Minerva Endocrinologica 31:107, 2006.
Wuts et al. "The Role of Protective Groups in Organic Synthesis," John Wiley, New York, 2nd Ed. 1991.
Yan et al., Analgesic action of microinjection of neurokinin A into the lateral reticular nucleus and nucleus raphe magnus in rats. Acta Physiologica Sinica, vol. 48, No. 5, pp. 493-496 (1996)—abstract.
Yang et al., Division and differentiation of natural antibody-producing cells in mouse spleen. PNAS, 104(11): 4542-4546 (2007).
Yoshida et al., Absorption of insulin delivered to rabbit trachea using aerosol dosage form. J. Pharm. Sci. 68(5): 670-671 (1979).
Yoshioka et al., "Serum proinsulin levels at fasting and after oral glucose load in patients with Type 2 (non-insulin dependent) diabetes mellitus", Diabetogia, 1988, 31, 355-60.
Yu W, Marino MT, Cassidy JP, et al. Insulin antibodies associated with Technosphere® insulin. ADA 2010; Abstract 216-OR.
Yusta B et al. "GLP-1 receptor activation improves b-cell function and survival following induction of endoplasmic reticulum stress." Cell Metabolism 4:391, 2006.
Zander et al., Effect of 6-week course of glucagon-like peptide 1 on glycaemic control, insulin sensitivity, and beta-cell function in type 2 diabetes: a parallel-group study. Lancet, 359:824-830, 2002.
Zethelius et al., "Proinsulin is an Independent Predictor of Coronary Heart Disease", Circulation 105:2153-2158 (2002).
Zimmerman, K., "Respiratory System: Fats, Function, and Diseases", <www.livescience.com/22616-respiratory-system.html>, copyright 2013, p. 1.
Zisser et al. "In Patients Using Technospere Insulin. Variation in PPG Stayed Within ADA-recommended Targets Despite Large Variations in Glucose Load." Mannkind Corporation (2010), ADA 2010; Poster 554.
Zisser H, Jovanovic L, Markova K, et al. Technosphere® insulin effectively controls postprandial glycemia in patients with type 2 diabetes mellitus. Diabetes Technology and Therapeutics 2012;14:997-1001.
Wasada, Glucagon-like peptide-1 (GLP-1). Nihon Rinsho, vol. 62, No. 6, pp. 1175-1180 (2004) (full Japanese article with English abstract).
Bosquillon et al., Pulmonary delivery of growth hormone using dry powders and visualization of its local fate in rates. Journal of Controlled Release 96: 233-244 (2004).
Cho et al., Targeting the glucagon receptor family for diabetes and obesity therapy. Pharmacology & Therapeutics 135: 247-278 (2012).
Definition of medicament from http://medical-dictionary.thefreedictionary.com/medicament, retrieved by the Examiner on Mar. 20, 2015 and cited in Office Action dated Mar. 26, 2015 in U.S. Appl. No. 13/942,482.
Definition of matrix from http://medical-dictionary.thefreedictionary.com/matrix, retrieved by the Examiner on Mar. 5, 2015 and cited in Office Action dated Mar. 26, 2015 in U.S. Appl. No. 12/471,260.
Diabetes Frontier, vol. 10, No. 5, p. 647-657 (1999) (full Japanese article with translated English portion provided in separate attachment, portion translated in English is the bottom of p. 655 and the left col. of p. 656).
Ely et al., Effervescent dry powder for respiratory drug delivery. European Journal of Pharmaceutics and Biopharmaceutics 65: 346-353 (2007).
European Search report for European Application 14192154.4 dated Mar. 19, 2015.
Extended European Search report for European Application 14187552.6 dated Mar. 2, 2015.
Gillespie et al., Using carbohydrate counting in diabetes clinical practice. Journal of the American Diabetic Association, vol. 98, No. 8, p. 897-905 (1998).
Yamamoto et al., Engineering of Poly (DL-lactic-co-glycolic acid) Nano-composite particle for dry powder inhalation dosage forms of insulin with spray fludized bed granulating system. J. Soc. Powder Technol., Japan, 41: 514-521 (2004).
Johnson et al., "Turbuhaler a new device for dry powder terbutaline inhalation", Allergy 43(5):392-395 (1988).
Johnson et al: RyR2 and calpain-10 delineate a novel apoptosis pathway in pancreatic islets. J Biol Chem., 279 (23)24794-802, 2004.
Johnson, Keith A., Preparation of peptide and protein powders for inhalation. Advanced Drug Delivery Reviews 1997; 26:3-15.
Jones et al., An investigation of the pulmonary absorption of insulin in the rat. Third European Congress of Biopharmaceutics and Pharmacokinetics, (1987).
Joseph et al. "Oral delivery of glucagon-like peptide-1 in a modified polymer preparation normalizes basal glycaemia in diabetic db/db mice." Diabetologia 43:1319-1328, 2000.
Joy et al. "Incretin mimetics as emerging treatments for type 2 diabetes." Annal Pharmacother 39:110, 2005.
Juntti-Berggren et al. "The antidiabetogenic effect of GLP-1 is maintained during a 7-day treatment period and improves diabetic dyslipoproteinemia in NIDDM patients." Diabetes Care 19:1200-1206, 1996.
Kanse et al. "Identification and characterization of glucagon-like peptide-1 7-36 amide-binding sites in the rat brain and lung." FEBS Letters 241:209, 1988.
Kapitza C et al. "Impact of particle size and aerosolization time on the metabolic effect of an inhaled insulin aerosol." Diabetes Tech Ther 6:119, 2004.
Kapitza et al. "Dose-response characteristics for a new pulmonary insulin formulation and inhaler." Presented at the 35th Annual Meeting of the EASD, Sep. 2000, abstract OP29 184.
Kapsner P, Bergenstal RM, Rendell M, et al. Comparative efficacy and safety of Technosphere® insulin and a rapid-acting analog both given with glargine in subjects with type 1 diabetes in a 52-week study. Diabetologia 2009; 52 (suppl 1).
Katchalski E et al. "Synthesis of lysine anhydride", J. Amer Chem Soc 68:879-880, 1946.
Katz et al. "Quantitative insulin sensitivity check index: a simple, accurate method for assessing insulin sensitivity in humans." J. Clin. Endocrinol. Metab. 85:5402-2410, 2000.
Kaur et al. "A Delineation of Diketopiperazine Self-Assembly Processes: Understanding the Molecular Events Involved in Ne-(Fumaroyl)diketopiperazine of L-Lys (FDKP) Interactions." Molecular Pharmaceutics, vol. 5, No. 2, 294-315, Accepted and Received 2007, published on web 2008.
Kawai et al. "Evidence that glucagon stimulates insulin secretion through its own receptor in rats." Diabetologia 38:274, 1995.
Kawamori et al. "Does hyperinsulinemia accelerate atherosclerosis?" Department of Medicine, Juntendo University School, vol. 13, No. 12, p. 954-960, 1994.
Kelley, D. et al. "Impaired postprandial glucose utilization in non-insulin dependent diabetes mellitus." Metabolism 43:1549-1557, 1994.
Kenny AJ et al. "Dipeptidyl peptidase IV, a kidney brush-border serin peptidase." Biochem J. 155:169, 1976.
Kim et al. "Development and characterization of a glucagon-like peptide 1-albumin conjugate. The ability to activate the glucagon-like peptide 1 receptor in vivo." Diabetes 52:751, 2003.
Kinzig et al. "The diverse roles of specific GLP-1 receptors in the control of food intake and the response to visceral Illness." J Neurosci 22:10470, 2002.
Kirk et al. "Disparities in HbA1c levels between African-American and non-hispanic white adults with diabetes." Diabetes Care 29:2130, 2006.
Kitabchi, Proinsulin and C-peptide:a review. May 26, 1977 (5):547-87, http://www/ncbi.nlm.nih.gov/pubmed/403392.
Klinger et al., Insulin-micro and nanoparticles for pulmonary delivery. International Journal of Pharmaceutics, vol. 377, pp. 173-179 (2009).

(56) References Cited

OTHER PUBLICATIONS

Knop et al. "No hypoglycemia after subcutaneous administration of glucagon-like peptide-1 in lean type 2 diabetic patients and in patients with diabetes secondary to chronic pancreatitis." Diabetes Care 26:2581, 2003.
Knop et al. "Reduced incretin effect in type 2 diabetes. Cause or consequence of the diabetic state?" Diabetes 56:1951, 2007.
Kohler D et al. Non-radioactive approach for measuring lung permeability: inhalation of insulin. Atemw Lungenkrkh 13:230-232, 1987. (English translation attached).
Kohler, "Aerosols for Systemic Treatment", Lung (Suppl.) 677-684 (1990).
Komada et al., Intratracheal delivery of peptide and protein agents: absorption from solution and dry powder by rat lung. J. Pharm. Sci. 83(6): 863-867 (1994).
Komatsu et al. "Glucagonostatic and insulinotropic action of glucagon-like peptide-1 (7-36)-amide." Diabetes 38:902, 1989.
Koning et al., Relationship between inspiratory flow through simulated dry powder inhalers and peak maximal inspiratory pressure. Flow Through a Simulated DPI, Chapter 3, pp. 43-56 (2001).
Labiris et al., Pulmonary drug delivery. Part I: Physiological factors affecting therapeutic effectiveness of aerosolized medications. British Journal of Clinical Pharmocology 56: 588-599 (2003).
Kontny et al., Issues Surrounding MDI Formulation Development with Non-CFC Propellants), J. Aerosol Med 4(3), 181-187 (1991).
Kopple et al. "A convenient synthesis of 2,5-piperazinediones." J Org Chem p. 962, 1967.
Kraft KS, Grant M. Preparation of macromolecule-containing drug powders for pulmonary delivery Methods in Molecular Biology 2009;480:165-174.
Kreymann B et al. "Glucagon-like peptide-1 7-36: a physiological incretin in man." The Lancet, Dec. 5, 1987, p. 1300.
Krssak, M. et al. "Alterations in postprandial hepatic glycogen metabolism in type 2 diabetes." Diabetes 53:3048-3056, 2004.
Krueger et al. "Toxicological profile of pulmonary drug delivery agent." Presented at the American Diabetes Association 64th Scientific Sessions, Jun. 2004, abstract 465-P.
Kwon et al. "Signaling elements involved in the metabolic regulation of mTOR by nutrients, incretins, and growth factors in islets." Diabetes 53:S225, 2004.
Lankat-Buttgereit B et al. "Molecular cloning of a cDNA encoding for the GLP-1 receptor expressed in rat lung." Exp Clin Endocrinol 102:241, 1994.
Laureano et al. "Rapid absorption and elimination of insulin from the lung following pulmonary administration of Technosphere®/Insulin: A pharmacokinetic study in a rat model." Presented at the American Diabetes Association 65th Scientific Sessions, Jun. 2005, abstract 445-P.
Leahy et al. Beta-cell dysfunction in type II diabetes mellitus. Curr Opin Endocrinol Diabetes 2:300-306, 1995.
Lebovitz "Therapeutic options in development for management of diabetes: pharmacologic agents and new technologies." Endocr Pract 12:142, 2006.
Lee et al."Synthesis, characterization and pharmacokinetic studies of PEGylated glucagon-like peptide-1" . Bioconjugate Chem 16:377, 2005.
Lee et al., "Development of an Aerosol Dosage Form Containing Insulin", J. Pharm. Sci. 65(4), 567-572 (1976).
Leiner et al. "Particles facilitate the absorption of insulin in a primary cell culture model of alveolar epithelium without evidence of cytotoxicity." Presented at the American Diabetes Association 64th Scientific Sessions, Jun. 2004, abstract 467-P.
Liner et al. "The pharmacokinetic profile of insulin administered by inhalation in the rat." Diabetes 53 Supplement, Jun. 2004, A111.
Leone-Bay et al. "Evaluation of novel particles as an inhalation system for GLP-1." Diabetes, Obesity and Metabolism. 11:1050-1059, 2009.
Leone-Bay A, Grant M. Technosphere® Technology: A Platform for inhaled protein therapeutics. OndrugDelivery 2006 (published online).

Leone-Bay A, Grant M. Technosphere®/insulin: mimicking endogenous insulin release. In: Rathbone M, Hadgraft J, Roberts M, et al, eds. Modified Release Drug Delivery, 2e. New York, NY: Informa Healthcare USA, Inc; 2008.
Kieffer et al. "The glucagon-like peptides." Endocrine Reviews 20:876, 1999.
Bilheimer DW, Ren H, Boss AH. Analysis of cardiovascular adverse events in patients with type 1 or type 2 diabetes enrolled in selected therapeutic trials in the phase 2/3 Technosphere® insulin development program. ADA 2011. Poster 922-P.
Billings CC, Smutney CC, Howard CP, et al. Handleability and characterization of inhalation profiles using the Gen2 delivery system in a pediatric population. Diabetes Technology Meeting 2010; poster.
Biodel's Intellecutal Property position strengthened for ultra-rapid-acting insulin programs by notice of intent to grant from European Patent Office. Newswire Feed, published May 2, 2012.
Blazquez E et al. "Glucagon-like peptide-1 (7-36) amide as a novel neuropeptide." Mol Neurobio 18:157, 1998.
Bloomgarden "Gut-derived incretin hormones and new therapeutic approaches." Diabetes Care 27:2554, 2004.
Boer et al., Design and application of a new modular adapter for laser diffraction characterization of inhalation aerosols. International Jornal of Pharmaceutics 249, pp. 233-245 (2002).
Boer et al., Inhalation characteristics and their effects on in vitro drug delivery from dry powder inhalers. Part 1. Inhalation characteristics, work of breathing and volunteers' preference in dependence of the inhaler resistance. Int. J. Pharm. 130 (1996) 231-244.
Bojanowska "Physiology and pathophysiology of glucagon-like peptide-1 (GLP-1): the role of GLP-1 in the pathogenesis of diabetes mellitus, obesity and stress." Med Sci Monit 11:RA271, 2005.
Bonner-Weir S et al. "New sources of pancreatic beta-cells." Nat Biotechnol 23:857-61, 2005.
Boss AH et al. "Inhaled Technosphere®/Insulin: Glucose elimination at the right time?" Poster presented at the American Diabetes Association 65th Scientific Sessions, Jun. 2005, abstract 443-P.
Boss AH et al. "Insulin bio-effect is limited by speed of absorption and elimination: similarities between an inhaled insulin formulation that mimics first-phase kinetics and i.v. insulin." Diabetologia 47:A314, 2004.
Boss AH et al. "Mimicry of the early phase insulin response in humans with rapidly available inhaled insulin accelerates post prandial glucose disposal compared to slower bioavailable insulin." Presented at the American Diabetes Association 65th Scientific Sessions, Jun. 2005, abstract 1373-P.
Boss AH et al. "Does kinetics matter? Physiological consequences of the ability of Technosphere®/Insulin inhalation to mimic first phase insulin release." Presented at the 5th Annual Meeting of the Diabetes Technology Society, Nov. 2005, abstract A14.
Boss AH et al. "Markedly reduced post prandial glucose excursions through inhaled Technosphere®/Insulin in caomparison to SC injected regular insulin in subjects with type 2 diabetes." 1st Annual Meeting of the European Association for the Study of Diabetes, Sep. 2005, abstract 816.
Boss AH et al. "The variability and time-action profile of inhaled Technosphere®/Insulin compares favorably to that of subcutaneous human regular insulin." Presented at the American Diabetes Association 65th Scientific Sessions, Jun. 2005, abstract 358-OR.
Boss et al. "Prandial Insulin: Is Inhaled Enough?" Drug Development Research 69(3):138-142 (2008).
Boss A H, Petrucci R, Lorber D. Coverage of prandial insulin requirements by means of an ultra-rapid-acting inhaled insulin. Journal of diabetes science and technology 2012;6:773-779.
Boss AH, Baughman RA, Evans SH, et al. A 3 month comparison in type 1 diabetes of inhaled Technosphere®/Insulin (TI) to Sc administered rapid-acting insulin analogue (RAA) as prandial insulin in a basal/prandial regimen. Diabetes 2006; 55:A97.
Boss AH, Evans SH, Firsov I, et al. Technosphere® insulin as effective as sc rapid acting insulin analogue in providing glycemic control in a 6-month study of patients with type 2 diabetes. Diabetes Technology Meeting 2006; poster.

(56) References Cited

OTHER PUBLICATIONS

Boss AH, Evans, SH, Ren, H, et al. Superior post prandial glucose control in patients with type 1 diabetes when using prandial technosphere insulin compared to NovoLog. Diabetologia 2006; Abstract 181.
Boss AH, Marino MT, Cassidy JP, et al. C-peptide correction method to determine exogenous insulin levels in pharmacokinetic studies using Technosphere® insulin. Diabetologia 2009; 52 (suppl 1).
Boss AH, Raskin P, Philips M, et al. Glycosylated hemoglobin and hypoglycaemia in patients with Type 2 diabetes mellitus: Technosphere® insulin and usual antihyperglycaemic regimen vs usual antihyperglycaemic regimen. Diabetologia 2010;53(suppl 1).
Brandt D, Boss AH. The next generation insulin therapy. OndrugDelivery 2006 (published online).
Brange et al., "Insulin Structure and Stability", Pharm Biotechnol, 5:315-50 (1993).
Bray "Exanatide" Am J Health-Sys Pharm 63:411, 2006.
Brownlee et al. "Glycemic variability: a hemoglobin A1c-independent risk factor for diabetic complications." JAMA 295:1707, 2006.
Bruce, D.G., et al."Physiological importance of deficiency of early prandial insulin secretion in non-insulin-dependent dliabetes." Diabetes 37:736-44, 1988.
Bullock BP et al. "Tissue distribution of messenger ribonucleic acid encoding the rat glucagon-like peptide-1 receptor." Endocrinology 137:2968, 1996.
Burcelin et al. "Encapsulated, genetically engineered cells, secreting glucagon-like peptide-1 for the treatment of non-insulin-dependent diabetes mellitus." Ann N Y Acad Sci. Jun. 18, 1999;875:277-85.
Calles-Escandon, J. and Robbins, D.C. "Loss of early phase insulin release in humans impairs glucose tolerance and blunts thermic effect of glucose." Diabetes 36:1167-72, 1987.
Camilleri, Clinical Practice: Diabetic Gastroparesis. The New England Journal of Medicine, 356: 820-829 (2007).
Campos et al. "Divergent tissue-specific and developmental expression of receptors for glucagon and glucagon0like peptide-1 in the mouse." Endocrinology 134:2156, 1994.
Cassidy J P, Amin N, Marino M, et al. Insulin lung deposition and clearance following Technosphere® insulin Inhalation powder administration. Pharmaceutical Research 2011; 28:2157-2164.
Cassidy J, Amin N, Baughman R, et al. Insulin kinetics following Technosphere® insulin inhalation powder administration unchanged in albuterol-treated asthmatics. ADA 2010; Poster 522.
Cassidy J, Baughman RA, Tonelli G, et al. Use of rapid acting insulin analog as the baseline infusion during glucose clamping improves pharmacokinetic evaluation. ADA 2007; 56: Abstract 602-P.
Cassidy JP, Baughman RA, Schwartz SL, et al. Afresa® (Technosphere® insulin) dosage strengths are interchangeable ADA 2009; Poster 433.
Cassidy JP, Marino MT, Amin N, et al. Lung deposition and absorption of insulin from Afresa® (Technosphere® Insulin) ADA 2009; Poster 425.
Cassidy JP, Potocka E, Baughman RA, et al. Pharmacokinetic characterization of the Technosphere® inhalation platform Diabetes Technology Meeting 2009. poster.
Caumo et al. "First-phase insulin secretion: does it exist in real life Considerations on shape and function." Am J Physiol Endocrinol Metab 287:E371-E385, 2004.
Cefalu "Concept, Strategies and Feasibility of Noninvasive Insulin Delivery." Diabetes Care 27:239-246, 2004.
Cefalu "Novel routes of insulin delivery for patients with type 1 or type 2 diabetes." Ann Med 33:579-586, 2001.
Cefalu et al., Inhaled human insulin treatment in patients with type 2 diabetes mellitus. Ann. Int. Med., 2001, 134(3): 203-207.
Ceglia et al. "Meta-analysis: efficacy and safety of inhaled insulin therapy in adults with diabetes mellitus." Ann Intern Med 145:665, 2006.
Cerasi, et al. Decreased sensitivity of the pancreatic beta cells to glucose in prediabetic and diabetic subjects. A glucose dose-response study. Diabetes 21(4):224-34, 1972.
Cernea et al. "Dose-response relationship of oral insulin spray in healthy subjects." Diabetes Care 28:1353-1357, 2005.
Cernea et al. "Noninjectable Methods of Insulin Administration." Drugs of Today 2006, 42 (6): 405-424.
Chan et al., "Pharmacological Management of Type 2 Diabetes Mellitus: Rationale for Rational Use of Insulin", Mayo Clin Proc, 2003, 78, 459-467.
Chase et al., "Redefining the clinical remission period in children with type 1 diabetes", Pediatric Diabetes, 2004, 5, 16-19.
Cheatham et al. "Desirable Dynamics & Performance of Inhaled Insulin Compared to Subcutaneous Insulin Given at Mealtime in Type 2 Diabetes: A Report from the Technosphere/Insulin Study Group." Diabetes Technology and Therapeutics, vol. 6, p. 234 (2004).
Cheatham et al. "A novel pulmonary insulin formulation replicates first phase insulin release and reduces s-proinsulin levels." Presented at the American Diabetes Association 64th Scientific Sessions, Jun. 2004, abstract 457-P.
"An inhaled insulin formulation (Technosphere Insulin) effectively improves glycaemic control in patients with type 2 diabetes mellitus." Inpharma Weekly, vol. 1522, Jan. 28, 2006, p. 8.
Actos Product Insert. Aug. 2008.
Adjusting Mealtime Insulin Doses. BD Diabetes. http://www.bd.com/diabetes/page.aspx?cat=7001&id=7280 (2014).
Ahren "GLP-1 and extra-islet effects." Horm. Med Res 36:842, 2004.
Ahren B et al. "Characterization of GLP-1 effects on b-cell function after meal ingestion in humans." Diabetes Care 26:2860, 2003.
Ahren B., Glucagon-like peptide-1 (GLP-1): a gut hormone of potential interest in the treatment of diabetes. BioEssays, V. 20, pp. 642-651 (1998).
Akerlund et al., Diketopiperazine-based polymers from common acids. Journal of Applied Polymer Science (2000), 78(12), 2213-2218.
Alabraba et al. Diabetes Technology & Therapeutics. Jul. 2009, 11(7): 427-430.
Alcohols limited. Alcohol speciality solvents—Go green! Jul. 24, 2010. Available from: <http://webarchive.org/web/20100724193725/http://www.alcohols.co.uk/speciality_solvents.php>.
Aljada et al. "Insulin inhibits the pro-inflammatroy transcription factor early growth response gene-1 (Egr)-1 expression in mononuclear cells (MNC) and reduces plasma tissue factor (TF) and plasminogen activator inhibitor-1 (PAI-1) concentrations." The Journal of Clinical Endocrinology and Metabolism, vol. 87, No. 3, p. 1419-1422, 2002.
Al-Showair et al., Can all patients with COPD use the correct inhalation flow with all inhalers and does training help? Respiratory Medicine, vol. 101, No. 11, p. 2395-2401 (2007).
American Diabetes Association, "Standards of medical care in diabetes—2009", Diabetes Care, Jan. 2009, 32 Suppl 1: S13-61.
Amin N, Boss AH, Petrucci R, et al. Pulmonary functions (over 2 years) in diabetic subjects treated with Afresa® or usual antidiabetic treatment ADA 2009; Poster 570.
Amin N, et al. Long-term sustained safety and efficacy of continued use of Technosphere insulin in subjects with type 2 diabetes. Abstract—Oral Presentation 215, 48th EASD Annual Meeting, Sep. 29-Oct. 2, 2009, Vienna Austria.
Amin N, Marino MT, Cassidy JP, et al. Acute pulmonary effects of Technosphere® insulin inhalation powder administered using a Gen2B inhaler compared to MedTone® C inhaler Diabetes Technology Meeting 2010; poster.
Amin N, Phillips M, Boss AH, et al. Pulmonary functions (over 2 years) in diabetic patients treated with Technosphere® insulin (TI) or usual antidiabetic treatment. Third International Conference on Advanced Technologies and Treatments for Diabetes. 2010; Poster 290.
Angelo et al., Technosphere Insulin: Defining the Role of Technosphere Particles at the Cellular Level. J. Diabetes Sci. Technol., vol. 3, Issue 3, pp. 545-554 (2009).

(56) References Cited

OTHER PUBLICATIONS

Angelo et al. Technosphere® insulin inhalation powder: Defining the mechanism of action. ADA 2008; 57: Poster 428-P.
Antosiewiez et al., Prediction of pH-dependent properties of proteins. J Mol. Biol., 238:415-436 (1994).
Arakawa et al., Preferential interactions determine protein solubility in three-component solutions: the MgCl2 system. Biochemistry, 29:1914-1923 (1990).
Ashwell et al. "Twice-daily compared with once-daily insulin glargine in people with Type 1 diabetes using meal-time insulin aspart." 2006 Diabetes UK, Diabetic Medicine, 23, 879-886.
Ashwell et al., "Optimal timing of injection of once-daily insulin gargine in people with Type 1 diabetes using insulin lispro at meal-times" 2005 Diabetes UK, Diabetic Medicine, 23, 46-52.
Atherton, E et al. "Synthesis of 2(R)-A3(S)-Acylamino-2-OXO-1-Azetidinyloxy U-Acetic Acids." Tetrahedron, vol. 10, No. 6, Jan. 1, 1984, pp. 1039-1046.
Avandia Product Insert, Oct. 2008.
Baggio et al. "A recombinant human glucagon-like peptide (GLP)-1-albumin protein (Albugon) mimics peptidergic activation of GLP-1 receptor-dependent pathways coupled with satiety, gastrointestinal motility, and glucose homeostatsis." Diabetes 53:2492, 2004.
Baggio et al. "Glucagon-like peptide-1, but not glucose-dependent insulinotropic peptide, regulates fasting glycemia and noneneteral glucose clearance in mice." Endocrinology 141:3703, 2000.
Baggio et al. "Harnessing the therapeutic potential of glucagon-like peptide-1" Treat Endocrinol 1:117, 2002.
Drucker et al., Minireview: The glucagon-like peptides. Endocrinology, vol. 142, No. 2, pp. 521-527 (2001).
Balkan B et al. "Portal GLP-1 administration in rats augments the insulin response to glucose via neuronal mechanisms." Am J. Physiol Regulatory Integrative Comp Physiol 279:R1449, 2000.
Barnett AH et al. "An open, randomized, parallel-group study to compare the efficacy and safety profile of inhaled human insulin (Exubera) with glibenclamide as adjunctive therapy in patients with Type 2 diabetes poorly controlled on metformin." Diabetes Care 29(8):1818-1825, 2006.
Barnett et al., An open, randomized, parallel-group study to compare the efficacy and safety profile of inhaled human insulin (Exubera) with metformin as adjunctive therapy in patients with type 2 diabetes poorly controlled on a sulfonylurea. Diabetes Care, 29(6): 1282-1287 (2006).
Barragan et al. "Changes in arterial blood pressure and heart rate induced by glucagon-like peptide-1-(7-36) amide in rats." Am J. Physiol 266 (Endocrinol Metab 29):E459, 1994.
Basu A et al. "Effects of a change in the pattern of insulin delivery on carbohydrate tolerance in diabetic and nondiabetic humans in the presence of differing degrees of insulin resistance." J Clin Invest 97:2351-2361, 1996.
Bauer et al., "Assessment o beta-adrenergic receptor blockade after isamoitane, a 5-HT1-receptor active compound, in healthy volunteer", Clin. Pharmacol Ther 53:76-83 (1993).
Bauer et al., "Pharmacodynamic effects of inhaled dry powder formulations of fenterol and colforsin in asthma", Clin Pharmacol Ther 53:76-83, 1993.
Baughman R, Cassidy J, Amin N, et al. A phase I, open-label study of the effect of albuterol or fluticasone on the pharmacokinetics of inhaled Technosphere® insulin inhalation powder in healthy subjects. ADA 2010; Poster 528.
Baughman R, Cassidy J, Levy B, et al. Technosphere® insulin inhalation powder pharmacokinetics unchanged in subjects who smoke. Diabetes 2008; 57: A128.
Baughman R, Haworth P, Litwin J, et al. No cardiac effects found with therapeutic and suprtherapeutic doses of Technosphere® inhalation powder: results from a thorough QTc clinical study. ADA 2011. Poster 933-P.
Baughman, RA, Evans, SH, Boss, AH, et al. Technosphere insulin does not affect pulmonary function in a 6 month study of patients with type 2 diabetes. Diabetologia 2006;49:177-118.
Bayés M et al. "Gateways to clinical trials" Methods Find Exp Clin Pharmacol 24:431-455, 2002.
Beers et al., Section 2—Chapter 13—Diabetes Mellitus, The Merck Manual of Diagnosis and Therapy, Merck Research Laboratories, pp. 165-177 (1999).
Behme et al. "Glucagon-like peptide-1 improved glycemic control in type 1 diabetes." BMC Endocrine Disorders 3:3, 2003.
Bellary et al. "Inhaled insulin:new technology, new possibilities." Int J Clin Pract 60:728, 2006.
Belmin J et al. "Novel drug delivery systems for insulin. Clinical potential for use in the elderly." Drugs Aging 20:303-12, 2003.
Benita, Charaterization of Drug-Loaded Poly(d,l-lactide) Microspheres. J. Pharm. Sci., 73: 1721-1724 (1984).
Benito E et al. "Glucagon-like peptide-1-(7-36) amide increases pulmonary surfactant secretion through a cyclic adenosine 3',5'-monophosphate-dependent protein kinase mechanism in rat type II pneumocytes." Endocrinology 139:2363, 1998.
Bensch et al., Absorption of intact protein molecules across the pulmonary air-tissue barrier, Science 156: 1204-1206 (1967).
Berge et al., "Pharmaceutical Salts", J. Pharmaceutical Sciences, Review Article, 66(1):1-19 (1977).
Bergenstal R, Kapsner P, Rendell M, et al., Comparative efficacy and safety of Afresa® and a rapid-acting analog both given with glargine in subjects with T1 DM in a 52-week study ADA 2009; Poster 479.
Bergeron et al. "Macromolecular Self-Assembly of Diketopiperazine Tetrapeptides." J. Am. Chem. Soc. 116, 8479-8484, 1994.
Heine "Unlocking the opportunity of tight glycaemic control. Promise ahead: the role of inhaled insulin in clinical practice." Diabetes, Obesity and Metabolism 7:S19, 2005.
Heinemann "Variability of Insulin Absorption and Insulin Action." Diabetes Technology & Therapeutics, vol. 4, No. 5, pp. 673-682. 2002.
Heinemann et al. "Current status of the development of inhaled insulin." Br. J. Diabetes Vasc. Dis. 4:295-301, 2004.
Heinemann L et al. "Time-action profile of inhaled insulin." Diabetic Med 14:63-72, 1997.
Heinemann, L. "Intra-individual Variability of the Metabolic Effect of Inhales Insulin Together with an Absorption Enhancer", Diabetes Care, vol. 23, No. 9, Sep. 2000, p. 1343-1347.
Heise et al. "The effect of insulin antibodies on the metabolic action of inhaled and subcutaneous insulin." Diabetes Care 28:2161, 2005.
Herbst et al., Insulin Strategies for Primary Care Providers. Clinical Diabetes, vol. 20, No. 1, pp. 11-17 (2002).
Heubner et al. "On inhalation of insulin" Klinische Wochenschrift 16:2342, 1924. (Original and English translation Provided in one document).
Heyder "Particle Transport onto Human Airway Surfaces", Eur. J. Respir. Dis, Suppl. 119, 29-50 (1982).
Heyder, "Alveolar deposition of inhaled particles in humans", Am. Ind. Hyg. Assoc. J. 43(11): 864-866 (1982).
Hirsch IB "Insulin analogues." N Engl J Med 352:174-83, 2005.
Hirsch, "Type 1 Diabetes Mellitus and the Use of Flexible Insulin Regimens" American Family Phyician, Nov. 15, 1999, p. 1-16.
Hirshberg B et al. "Islet transplantation: where do we stand now?" Diabetes Metab Res Rev 19:175-8, 2003.
Hite et al. "Exhuberance over Exubera." Clin Diabetes 24(3):110-114, 2006.
Hoet et al., Review: Nanoparticles—known and unknown health risks. Journal of Nanobiotechnology, vol. 2, No. 12, (15 pages) (2004).
Hollander et al. "Efficacy and Safety of Inhaled Insulin (Exubera) Compared with Subcutaneous Insulin Therapy in Patients with Type 2 Diabetes." Diabetes Care, vol. 27, No. 10, Oct. 2004, p. 2356-2362.
Holst "Therapy of type 2 diabetes mellitus based on the actions of glucagon-like peptide-1." Diabetes Metab Res Rev 18:430, 2002.
Holst et al. "On the effects of glucagon-like peptide-1 on blood glucose regulation in normal and diabetic subjects." Ann N Y Acad Sci. Dec. 26, 1996;805:729-36.
Howard C, Ren H, Rossiter A, et al. Reduced incidence and frequency of hypoglycemia in an integrated analysis of pooled data

(56) References Cited

OTHER PUBLICATIONS from clinical trials of subjects with type 1 diabetes using prandial inhaled Technosphere® insulin. Diabetologia 2009; 52 (suppl 1).
Howard CP, Gnudi L, Loiter D, et al. Prandial inhaled Technosphere® insulin plus insulin glargine vs. biaspart 70/30 insulin in type 2 diabetes inadequately controlled with/without oral agents. Third International Conference on Advanced Technologies and Treatments for Diabetes. 2010; Poster 300.
Howard CP, Loiter D, Ren H, et al. Reduced incidence and frequency of hypoglycemia in pooled data from trials of type 2 diabetics using prandial inhaled Technosphere® insulin. Third International Conference on Advanced Technologies and Treatments for Diabetes 2010; Poster 304.
Howard CP, Petrucci R,Amin N, et al. Pulmonary function test remain similar in patients who received Technosphere® insulin and in patients currently receiving standard antidiabetic therapy. AACE 2010; Poster 267.
Howard CP, Ren H, Rossiter A, Boss AH. Reduced incidence and frequency of hypoglycemia in pooled data from trials of type 1 diabetics using prandial inhaled Technosphere® insulin. Third International Conference on Advanced Technologies and Treatments for Diabetes. 2010; Poster 302.
Howard CP, Ren H, Rossiter A, et al. Reduced incidence and frequency of hypoglycemia in an integrated analysis of pooled data from clinical trials of subjects with type 1 diabetes using prandial inhaled Technosphere® insulin. AACE 2010; Poster 269.
Howard CP, Rubin RR, Peyrot. M. Patient reported outcomes in adults with type 2 diabetes using mealtime Afresa® (inhaled Technosphere® insulin) and basal insulin versus premixed insulin ADA 2009; Poster 551.
http://www.bilcaresolutions.com/en/products/pharma-packaging-innovations-pvc-aclar-films <URL:http://web.archive.org/web/20110127102552/http://www.bilcaresolutions.com/en/products/pharma-packaging-innovations-pvc-aclar-films> published on Jan. 27, 2011 as per "Wayback Engine".
http://www.pmpnews.com/article/blister-packaging-materials (May 26, 2009).
Huda et al. "Gut peptides and the regulation of appetite." Obesity Reviews 7:163, 2006.
Hui et al., The short half-life of glucagon-like peptide-1 in plasma does not reflect its long-lasting beneficial effects. European Journal of Endocrinology, 146: 863-869 (2002).
Hussain et al. "State of insulin self-association does not affects its absorption from the pulmonary route." Eur. J. Pharm. Sciences 25:289-298, 2005.
Ikeda, Kuniki et al. "Peptide Antibiotics. XXVI. Syntheses of Cyclodipeptides Containing N. delta.-p-aminobenzenesulfonyl Ornithine Residue." Chemical & Pharmaceutical Bulletin, 20(9), 1849-55, 1972.
Imeryuz et al. "Glucagon-like peptide-1 inhibits gastric emptying via vagal afferent-mediated central mechanisms." Am J Physiol 273 (Gastrointest Liver Physiol 36):G920, 1997.
Insulin inhalation NN 1998, Drugs R & D, 2004, pp. 46-49, Adis Data Information BV.
Insulin is a natural product from http://www.levemir.com/startingoninsulin/whatisinulin.aspx, pp. 1-3. Accessed on Apr. 30, 2014 in Non-Final Offfice Action dated May 22, 2014 for U.S. Appl. No. 13/797,657 and in Non-Final Office Action dated May 22, 2014 for U.S. Appl. No. 12/883,369.
International Search Report for PCT International Application No. PCT/US2010/055323 filed on Nov. 3, 2010.
Witten Opinion dated Jul. 1, 2013 for International Application No. PCT/US2013/032162 filed on Mar. 15, 2013.
International Search Report dated Jun. 21, 2010 for International Application No. PCT/US2010/027038 filed on Mar. 11, 2010.
Written Opinion for International Application No. PCT/US2011/060057 filed on Nov. 9, 2011.
International Search Report dated Mar. 18, 2013 for International Application No. PCT/US2012/061749 filed on Oct. 24, 2012.

International Search Report dated Jun. 20, 2012 for International Applicaion No. PCT/US2012/031695 filed on Mar. 30, 2012.
International Search Report dated Nov. 19, 2014 for International Application No. PCT/US2014/049817 filed on Aug. 5, 2014.
International Search Report for International Application No. PCT/US2010/020448 filed on Jan. 8, 2010.
International Search Report dated Mar. 11, 2010 for International Application No. PCT/US2009/069745 filed on Dec. 29, 2009.
International Search Report dated Oct. 17, 2011 for International Application No. PCT/US2010/026271 filed on Mar. 4, 2010.
International Search Report for International Application No. PCT/US2010/038287 filed on Jun. 11, 2010.
Ishibashi, Norio et al. "Studies on Flavored Peptides. Part V. A Mechanism for Bitter Taste Sensibility in Peptides." Agricultural and Biological Chemistry, 52(3), 819-27, 1988.
Iwanij et al., Characterization of the Glucagon Receptor and its Functional Domains Using Monoclonal Antibodies. The Journal of Biological Chemistry, vol. 265, No. 34, pp. 21302-21308, 1990.
Jain et al. "Insulin Therapy in Type 2 Diabetic Subjects Suppresses Plasminogen Activator Inhibitor (PAI-1) Activity and Proinsulin-like Molecules Independently of Glycaemic Control." Diabetic Medicine, vol. 10, No. 1, p. 27-32, 1993.
Johnson et al., Peptide turn mimetics. Biotechnology and Pharmacy, p. 366-378 (1993).
International Search Report for International Application No. PCT/US2013/050392 filed on Jul. 12, 2013.
Li et al. "GLP-1; a novel zinc finger protein required in somatic cells of the gonad for germ cell development." Dev Biol 301:106, 2007.
Li, Jun. Chapter 15: Drug Therapy of Metabolic Diseases. Clinical Pharmacotherapy, People's Medical Publishing House, 1st Edition, pp. 333-335 (2007).
Lian et al. "A Self-Complimentary Self-Assembling Microsphere System: Application for Intravenous Delivery of the Antiepilpetic and Neuroprotectant Compound Felbanate." J Pharm Sci 89:867-875, 2000.
Lim, "Microencapsulation of Living Cells and Tissues", J. Pharm. Sci., 70: 351-354 (1981).
Linder et al., Increase in serum insulin levels is correlated with lung distribution after pulmonary delivery of Technosphere/Insulin. Diabetologia, No. 46, A277 (2003).
Liu et al., "Pulmonary delivery of free and liposomal insulin", Pharmaceuticals Res. 10:228-232, 1993.
Lorber D, Howard CP, Ren H, et al. Reduced incidence and frequency of hypoglycemia in an integrated analysis of pooled data from clinical trials of subjects with type 2 diabetes using prandial inhaled Technosphere® insulin. AACE 2010; Poster 270.
Luque et al. "Glucagon-like peptide-1 (GLP-1) and glucose metabolism in human myocytes." J. Endocrinol 173:465, 2002.
Luzi, L. and DeFronzo, R.A. "Effect of loss of first-phase insulin secretion on hepatic glucose production and tissue glucose disposal in humans" Am. J. Physiol. 257 (Endocrinol. Metab. 20):E241-E246, 1989.
Luzio, S.D., et al. "Intravenous insulin simulates early insulin peak and reduces post-prandial hyperglycaemia/hyperinsulinaemia in type 2 (non-insulin-dependent) diabetes mellitus." Diabetes Res. 16:63-67, 1991.
Malhotra et al., Exendin-4, a new peptide from Heloderma suspectum venom, potentiates cholecystokinin-induced amylase release from rat pancreatic acini. Regulatory Peptides, 41:149-56, 1992.
Mandal "Inhaled insulin for diabetes mellitus." Am J Health Sys Pharm 62:1359-64, 2005.
Mann "Pulmonary insulin—the future of prandial insulin therapy." Presented at the 5th Annual Meeting of the Diabetes Technology Society, Nov. 2005, abstract A94.
MannKind Corporation "Postprandial hyperglycemia: clinical significance, pathogenesis and treatment." MannKind Corporation Monograph. 2009.
MannKind Corporation, Pulmonary Delivery: Innovative Technologies Breathing New Life into Inhalable Therapeutics, www.ondrugdelivery.com, 2006.
Burcelin et al., Long-lasting antidiabetic effect of a dipeptidyl peptidase IV-resistant analong of glucagon-like peptide-1. Metabolism, vol. 48, No. 2, pp. 252-258 (1999).

(56) References Cited

OTHER PUBLICATIONS

Marino MT, Cassidy JP, Smutney CC, et al. Bioequivalence and dose proportionality of Afrezza® inhalation powder administered using a Gen2 inhaler compared to the MedTone® inhaler. Diabetes Technology Meeting 2010; poster.
Marino MT, Cassidy JP, Smutney CC, et al. Improvement in bioavailability of FDKP with the NexGen2A device: Implications for delivery of pulmonary insulin. Third International Conference on Advanced Technologies and Treatments for Diabetes 2010; Poster 108.
Marino MT, Cassidy JP, Smutney CC, et al. Improvement in bioavailability of FDKP and insulin with the NGDSB device. Third International Conference on Advanced Technologies and Treatments for Diabetes 2010; Poster 107.
Marino MT. A pharmacokinetic/pharmacodynamic model of inhaled insulin with application to clinical trial simulation. ADA 2010; Abstract 2105-PO.
Marino MT. Cassidy JP, Baughman RA, et al. C-peptide correction method to determine exogenous insulin levels in ok studies using Afresa® (Technosphere® insulin [TI] ADA 2009; Poster 1451.
Marshall "Preventing and detecting complications of diabetes." BMJ 333:455, 2006.
Mastrandrea "A breath of life for inhaled insulin: severe subcutaneous insulin resistance as an indication." Pediatric Diabetes 2010: 11: 377-379.
Mathiowitz, Morphology of Polyanhydride Microsphere Delivery Systems, Scanning Microscopy, 4: 329-340 (1990).
Mathiowitz, Novel microcapsules for delivery systems. Reactive Polymers, 6: 275-283 (1987).
Mathiowitz, Polyanhydride microspheres as drug carriers I, hot-melt microencapsulation. J. Controlled Medicine, 5: 13-22 (1987).
Mathiowitz, Polyanhydride microspheres as drug carriers II, microencapsulation by solvent removal. J. Appl. Polymer Sci., 35: 755-774 (1988).
Mathiowitz, Polyanhydride microspheres IV, morphology and characterization systems made by spray drying. J. App. Polymer Sci., 45: 125-134 (1992).
Matsui et al. "Hyperplasia of type II pheumocytes in pulmonary lymphangioleiomyomatosis. Immunohistochemical and electron microscope study." Arch Pathol Lab Med 124:1642, 2000.
Matthews DR et al. "Homeostasis model assessment: insulin resistance and beta-cell function from fasting plasma glucose and insulin concentrations in man." Diabetologia. Jul. 1985;28(7):412-9.
McElduff A et al. "Influence of acute upper respiratory tract infection on the absorption of inhaled insulin using the AERx(R) insulin diabetes management system." Br J Clin Pharmacol 59:546, 2005.
McMahon et al., "Effects of basal insulin supplementation on disposition of mixed meal in obese patients with NIDDM", Diabetes, vol. 38, pp. 291-303 (1989).
Meier et al. "Absence of a memory effect for the insulinotropic action of glucagon-like peptide-1 (GLP-1) in healthy volunteers." Horm Metab Res 35:551, 2003.
Meier et al. "Secretion, degradation, and elimination of glucagon-like peptide-1 and gastric inhibitor polypeptide in patients with chronic renal insufficiency and healthy control subjects." Diabetes 53:654, 2004.
Meier et al. "The glucagon-like peptide-1 metabolite GLP-1-(9-36) amide reduces postprandial glycemia independently of gastric emptying and insulin secretion in humans." Am J Physiol Endocrinol Metab 290:E1118, 2006.
Mendes et al., A non-dimensional functional relationship for the tine particle fraction produced by dry powder inhalers, Aerosol Science 38, pp. 612-624 (2007).
Mentlein et al., Dipeptidyl peptidase IV hydrolyses gastric inhibitory polypeptide, glucagon-like peptide-1 (7-36) amide, peptide histidine methionine and is responsible for their degradation in human serum. Eur J Biochem., 214:829-835, 1993.
Merck Manual 17th, Japanese Edition, NIKKEI BP Corp., 1999, p. 167-179.
Mitchell et al. "Intranasal Insulin: PK Profile Designed Specifically for Prandial Treatment of Type 2 Diabetes." Drug Development Research 69(3):143-152 (2008).
Monnier et al. "Activation of oxidative stress by acute glucose fluctuations compared with sustained chronic hyperglycemia in patients with type 2 diabetes." JAMA 295:1681, 2006.
Montrose-Rafizadeh et al., Diabetes, 45(Suppl. 2):152A, 1996.
Moren, Aerosols in Medicine (2nd Ed.), Elsevier, pp. 321-350 (1993).
Mudaliar et al., Insulin Therapy in Type 2 Diabetes. Endocrinology and Metabolism Clinics, vol. 30, No. 4, pp. 1-32 (2001).
Nagai et al., "Powder Dosage Form of Insulin for Nasal Administration", J. Control Ref., 1:15-22 (1984).
Narayan et al. "Impact of recent increase in incidence on future diabetes burden." Diabetes Care 29:2114, 2006.
Naslund E et al. "GLP-1 slows solid gastric emptying and inhibits insulin, glucagon, and PYY release in humans." Am J Physiol (Regulatory Integrative Comp Physiol 46):R910, 1999.
Naslund E et al. "Prandial subcutaneous injections of glucagon-like petide-1 cause weight loss in obese human subjects." Br J Nutrition 91:439, 2004.
International Search Report dated Nov. 21, 2013 for International Application No. PCT/US2013/057397 filed on Aug. 29, 2013.
Eavarone et al., A voxel-based monte carlo model of drug release from bulk eroding nanoparticles. Journal of Nanoscience and Nanotechnology, vol. 10, pp. 5903-5907 (2010).
Marino MT, Cassidy JP, Smutney CC, et al. Improvement in bioavailability of FDKP with the NexGen2A device: Implications for delivery of pulmonary insulin. Diabetes Technology Meeting 2009; poster.
Rosenstock et al. "Efficacy and Safety of Technosphere Inhaled Insulin Compared With Technosphere Powder Placebo in Insulin-Naive Type 2 Diabetes Suboptimally Controlled with Oral Agents." Diabetes Care, vol. 31, No. 11, pp. 2177-2182, 2008.
Rosenstock et al. "Inhaled Insulin Improves Glycemic Control when Substituted for or Added to Oral Combination Therapy in Type 2 Diabetes." Ann Intern Med 143:549-558, 2005.
Rosenstock et al., "Reduced hypoglycemia risk with insulin glargine: a meta-analysis comparing insulin glargine with human NPH insulin in type 2 diabetes", Diabetes Care, 28(4):950-5 (2005).
Rosenstock J, Baughman RA, Ribera-Schaub T, et Al. A randomized, double-blind, placebo controlled study of the efficacy and safety of inhaled Technosphere® insulin in patients with type 2 diabetes (T2DM). Diabetes 2005;54: Abstract 357-OR.
Rosenstock J, Lorber D, Petrucci R, et al. Basal/bolus with prandial inhaled Technosphere® insulin (TI) plus insulin glargine qd vs biaspart 70/30 insulin bid in T2 DM inadequately controlled on insulin with/without oral agents ADA 2009; Poster 466.
Rosenstock J, Lorger DL. Gnudi L, et al.Prandial inhaled insulin plus basal insulin glargine versus twice daily biaspart insulin for type 2 diabetes: a multicentre randomised trial. Lancet 2010;375:2244-2253.
Rossiter A, Amin N, Hams R, et al. Pulmonary safety of inhaled Technosphere® insulin therapy in adults with diabetes using high-resolution computerized tomography of the chest. Diabetologia 2009; 52 (suppl 1).
Rossiter A, Howard C, Amin N, et al. Technosphere® insulin: Safety in type 2 diabetes mellitus. ADA 2010; Poster 523.
Roumeliotis, New inhaler launched with a bag, in-Pharma Technologist.com, Decision News Media SAS (2006).
Rousseau et al. "Drug delivery by fumaryl diketopiperazine particles: evidence for passive transport." Presented at the American Diabetes Association 64th Scientific Sessions, Jun. 2004, abstract 484-P.
Rubin RR, Peyrot M. Psychometric properties of an instrument for assessing the experience of patients treated with inhaled insulin: The inhaled insulin treatment questionnaire (INTQ) Health & Quality of Life Outcomes 2010.8:32.
Rubin RR, Peyrot M; Patient reported outcomes in adults with type 1 diabetes using mealtime Afresa® (inhaled Technosphere® insulin) or rapid acting insulin with basal insulin ADA 2009; Poster 1881.

(56) References Cited

OTHER PUBLICATIONS

Ryan EA et al. "Successful islet transplantation. Continued insulin reserve provides long-term glycemic control." Diabetes 51:2148-2157, 2002.
Sajeesh et al., Cyclodextrin-insulin complex encapsulated polymethacrylic acid based nanoparticles for oral insulin delivery. International Journal of Pharmaceuticals, 2006, 325, pp. 147-154.
Sakagami M et al. "Respirable microspheres for inhalation: the potential of manipulating pulmonary disposition for improved therapeutic efficacy." Clin Pharmacokinet 44(3):263-277, 2005.
Sakr, A new approach for insulin delivery via the pulmonary route: design and pharmacokinetics in non-diabetic rabbits. International Journal of Pharmaceutics, 86: 1-7 (1992).
Salib, Utilization of sodium alginate in drug microencapsulation. Pharazeutische Industrie, 40(11a): 1230-1234 (1978).
Saraceni C et al. "Effects of glucagon-like peptide-1 and long-acting analogues on cardiovascular and metabolic function." Drugs R D 8:145, 2007.
Sarrach et al., "Binding and entrapment of insulin by liposomes made of lecithin-phosphotidix acid in acid solution" Pharmazie 40:642-645, 1985 (German and English Abstract).
Savage et al., "Effects of peptide YY (PYY) on mouth to caecum intestinal transit time and on the rate of gastric emptying healthy volunteers", Gut, vol. 28, pp. 166-170, 1987.
Sawhney et al., Bioerodible hydrogels based on photopolymerized poly(ethylene glycol)-co-poly(a-hydroxy acid) diacrylate macromere. Macromolecules, 26: 581-587 (1993).
Schaffer et al. "Assembly of high-affinity insulin receptor agonists and antagonists from peptide building blocks." PNAS 100:4435-4439, 2003.
Schepp et al., Eur. J. Pharmacol., 269:183-91, 1994.
Scherbaum "Unlocking the opportunity of tight glycaemic control. Inhaled insulin: clinical efficacy." Diabetes Obesity and Metabolism 7:S9-S13, 2005.
Schirra et al. "Gastric emptying and release of incretin hormones after glucose ingestion in humans." J Clin Invest 97:92-103, 1996.
Schluter et al., "Pulmonary Administration of Human Insulin in volunteers and Type I Diabetics", Diabetes, 33, (Suppl) 298 (1984).
Schneider et al., "Stimulation by proinsulin of expression of plasminogen activator inhibitor type 1 in endothelial cells", Diabetes 41(7):890-895 (1992).
Schon, Istvan et al. "Formation of Aminosuccinyl Peptides During Acidolytic Deprotection Followed by their Tranformation to Piperazine-2, 5-dione Derivatives in Neutral Media." International Journal of Peptide & Protein Research, 14(5), 485-494, 1979.
Schroder, "Crystallized carbohydrate spheres as a slow release matrix for biologically active substances", Biomaterials 5:100-104, 1984.
Scrocchi et al. "Glucose intolerance but normal satiety in mice with a null mutation in the glucagon-like peptide 1 receptor gene." Nature Medicine 2:1254-1258, 1996.
Seshiah & Balaji, "Early Insulin Therapy in Type 2 Diabetics", Int. J. Diabetes in Developing Countries, 2003, 23, 90-93.
Seville, P.C. et al., Preparation of dry powder dispersions for non-viral gene delivery by freeze-drying and spray drying. J. Gene Medicine 2002; 4:428-437.
Shah et al. "Lack of suprression of glucagon contributes to postprandial hyperglycemia in subjects with type 2 diabetes mellitus." J Clin Indocrinol Metab 85:4053, 2000.
Shelly et al. "Polysorbate 80 hypersensitivity." The Lancet 345:1312, 1995.
Shimada et al. Translocation pathway of the intertracheally instilled ultrafine particles from the lung into the blood circulation in the mouse. Toxicologic Pathology pp. 949-957 (2006).
Shojania et al. "Effect of quality improvement strategies for type 2 diabetes on glycemic control." JAMA 296:427, 2006.
Silverstein et al., "Care of Children and Adolescens with Type 1 Diabetes, A Statement of the American Diabetes Association", Diabetes Care, Jan. 2005, vol. 28, p. 186-212.
Singh et al., Use of 125I-[Y39]exendin-4 to characterize exendin receptors on dispersed pancreatic acini and gastric chief cells from guinea pig. Regul. Pept. 53 : 47-59 (1994).
Simms JR, Carballo I, Auge CR, et al. Assessment of immunotoxic effects on humoral and cellular immune parameters following repeated inhalation of Technosphere insulin in the rat. Diabetes 2005;54:Abstract 2078-PO.
Skyler, Pulmonary insulin: current status. Diabetes Voice, vol. 51, Issue I, p. 23-25, 2006.
Skyler "Pulmonary Insulin Delivery—State of the Art 2007" Diabetes Tecnology & Therapeutics, vol. 9, Supplement 1, pp. S1-S3. 2007.
Skyler JS et al. "Use of inhaled insulin in a basal/bolus insulin regimen in Type 1 diabetic subjects." Diabetes Care 28:1630-1635, 2005.
Smith et al. "New-onset diabetes and risk of all-cause and cardiovascular mortality." Diabetes Care 29:2012, 2006.
Smutney CC, Friedman EM, Amin N. Inspiratory efforts achieved in use of the Technosphere® insulin inhalation system. Diabetes Technology Meeting 2008; Poster SMUT8052.
Smutney CC, Friedman EM, Amin N. Inspiratory efforts achieved in use of the Technosphere® insulin inhalation system. Journal of Diabetes Science and Technology 2009 3(5):1175-1189.
Smutney CC, Polidoro JM, Adamo B, et al. In-vitro performance improvement realized in a next generation dry powder delivery system. Diabetes Technology Meeting 2009; poster.
Smutney CC, Polidoro JM, Adamo B, Shah S. In vitro performance improvement realized in a next generation dry powder delivery system. Third International Conference on Advanced Technologies and Treatments for Diabetes 2010; Poster 122.
Smutney CC, Polidoro JM. Easy-to-use next-generation pulmonary insulin delivery system. ADA 2010; Abstract 2093.
Smutney CC, Polidoro JM. Improvements realized in a next-generation pulmonary insulin delivery system. ADA 2010; Abstract 2097.
Sodium chloride is a natural product from http://www.wqpmag.com/potassium-chloride-vs-sodium-chloride, pp. 1-3. Accessed on May 16, 2014 in Non-Final Office Action dated May 22, 2014 for U.S. Appl. No. 13/797,657 and in Non-Final Office Action dated May 22, 2014 for U.S. Appl. No. 12/883,369.

\* cited by examiner

Spray dried at 0.4 bar

Spray dried at 0.6 bar

Spray dried at 0.7 bar

Spray dried at 105°C, 11 gram scale

Spray dried at 120°C, 11 gram scale

Spray dried at 120°C, 45 gram scale

Spray dried at 140°C, 11 gram scale

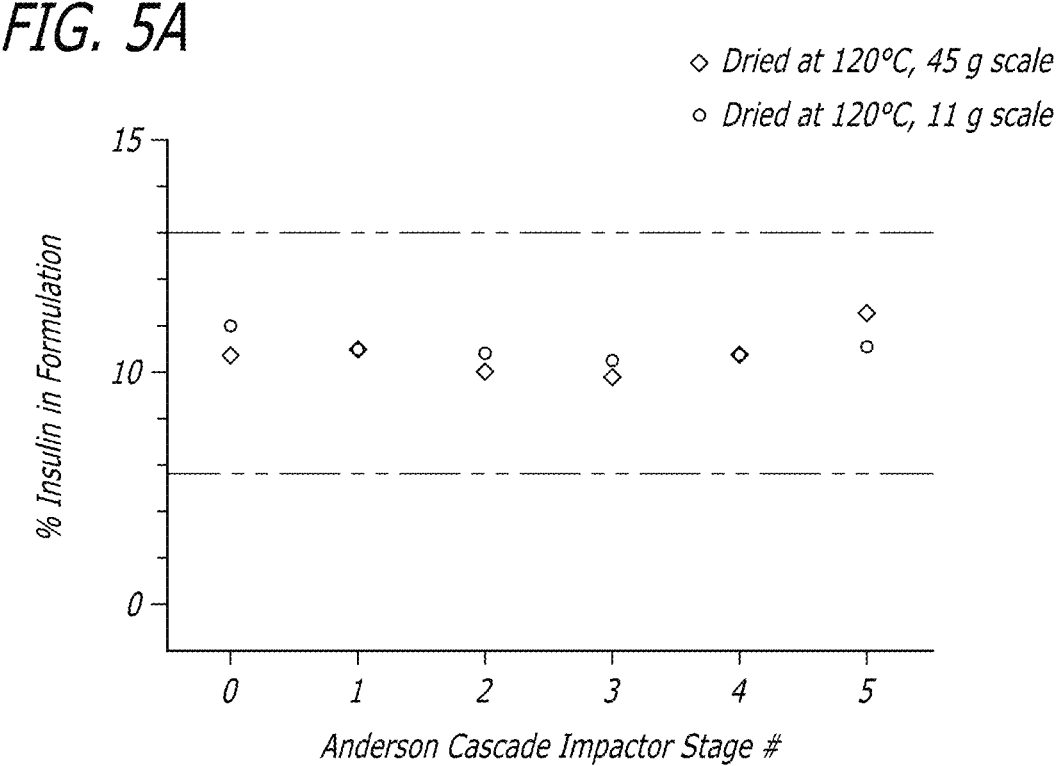

FIG. 5B
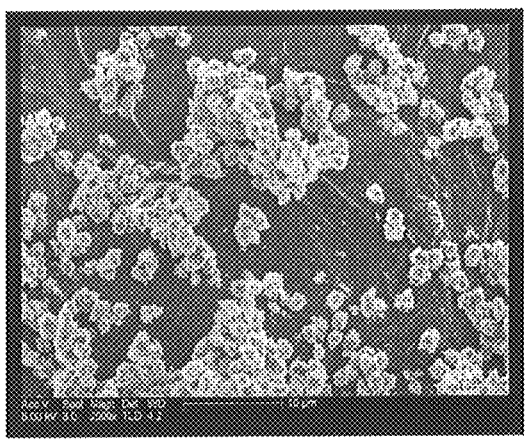
Lyophilized Formulation - 2,500 x
FIG. 5C
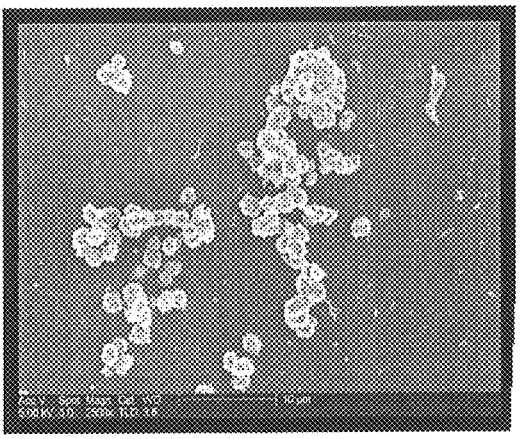
Spray Dried Formulation - 2,500 x
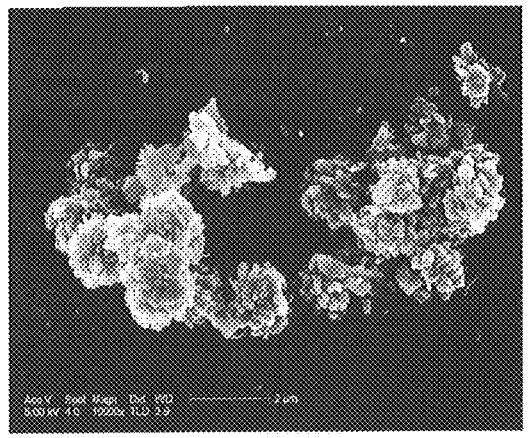
Lyophilized Formulation - 10,000 x
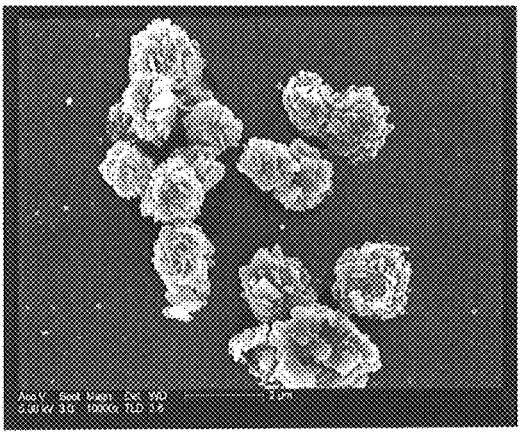
Spray Dried Formulation - 10,000 x
FIG. 5D
FIG. 5E FIG. 6A
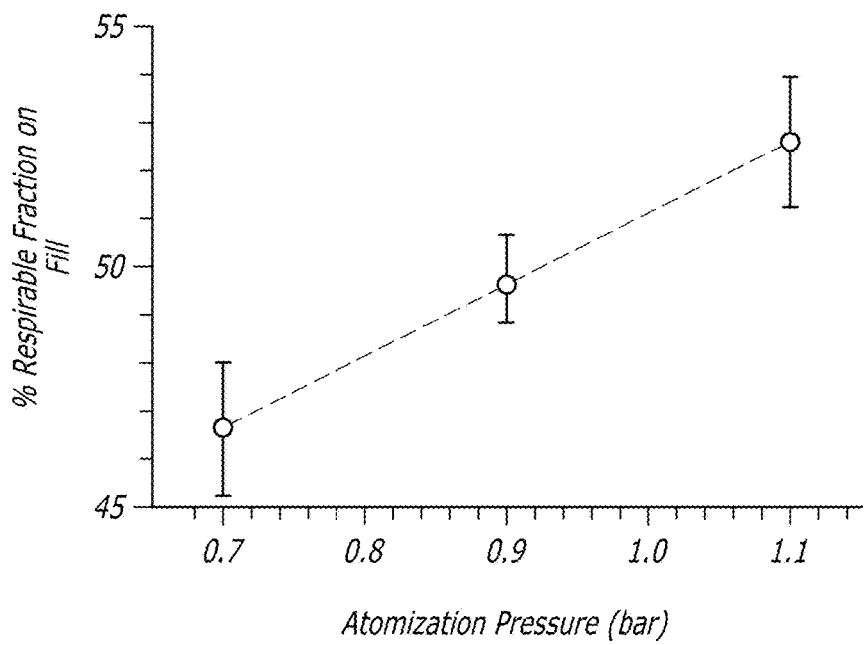
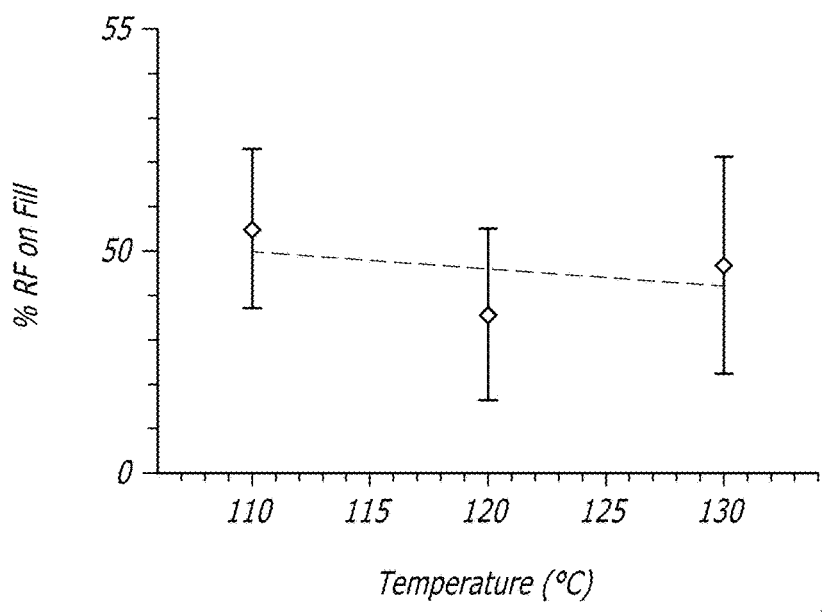
FIG. 6B Spray dried at 110°C, 0.7bar Spray dried at 110°C, 0.9bar Spray dried at 110°C, 1.1bar Spray dried at 120°C, 0.7bar Spray dried at 120°C, 0.9bar Spray dried at 120°C, 1.1bar Spray dried at 130°C, 0.7bar    Particle Size (μm)

Spray dried at 130°C, 0.9bar    Particle Size (μm)

Spray dried at 130°C, 1.1bar    Particle Size (μm)

METHOD FOR IMPROVING THE PHARMACEUTIC PROPERTIES OF MICROPARTICLES COMPRISING DIKETOPIPERAZINE AND AN ACTIVE AGENT

CROSS REFERENCE TO RELATED APPLICATIONS

The present application is a continuation of U.S. patent application Ser. No. 13/942,482 filed Jul. 15, 2013, which is a continuation of U.S. patent application Ser. No. 13/239,696 filed Sep. 22, 2011, which is a continuation of U.S. patent application Ser. No. 11/678,046 filed Feb. 22, 2007, which claims the benefit under of U.S. Provisional Application No. 60/776,605 filed Feb. 22, 2006, the contents of each of which is incorporated by reference herein in its entirety.

BACKGROUND OF THE INVENTION

Field of the Invention

The invention relates to the field of dry powder pharmaceuticals. The invention discloses methods of obtaining particles with improved aerodynamic performance or in which the active agent is more stable and efficiently delivered. More particularly, the present invention concerns methods for drying, particularly spray drying diketopiperazine-insulin (DKP-insulin) particles. The dry powders of the invention have utility as pharmaceutical formulations for pulmonary delivery.

Description of the Related Art

A number of different methodologies are employed in the art for preparing particles as a dry powder composition. These methodologies include, for example, lyophilization, evaporation, phase separation, and spray drying (see PCT Patent Application: WO 91/16038). In the manufacture of dry powder pharmaceuticals some methods start with the components in solution and form the particles of the powder by removing solvent. Other methods form particles in a separate, earlier step, such as by precipitation, and can result in a particle in suspension, which must then be dried. Methods such as lyophilization and evaporation are often used particularly for drying or removing a solvent from particles in suspension, whereas spray drying has more typically been used for particle formation from solution. For example, see U.S. Pat. Nos. 5,976,574; 5,985,248; 6,001,336; 6,051,256; 6,077,543; 6,365,190; 6,372,258; 6,423,344; 6,479,049; 6,509,006; 6,569406; 6,572,893; 6,582,728; 6,838,076; and 6,896,906.

Lyophilization, or freeze drying, involves a process in which solvent, typically water, is removed from a product after it is frozen and placed under a vacuum, allowing the ice to change directly from solid to vapor without passing through a liquid phase. The process consists of three separate, unique, and interdependent processes; freezing, primary drying (sublimation), and secondary drying (desorption). During spray drying, a (generally aqueous) solution is introduced via a nozzle (e.g., a two fluid nozzle), spinning disc, or an equivalent device into a hot gas stream. Passage through the nozzle atomizes the solution into fine droplets. The heat energy supplied by the gas stream causes the evaporation of water or other solvents, thereby producing fine particles.

Drug delivery using substituted diketopiperazine microparticles has been described in U.S. Pat. Nos. 5,352,461; 5,503,852; 6,331,318; 6,395,774 and 6,663,898. Pulmonary delivery of diketopiperazine microparticles as dry powders is described in U.S. Pat. Nos. 5,503,852; 6,428,771; 6,444,226 and 6,652,885. Various methods for forming and loading diketopiperazine particles for drug delivery are disclosed in U.S. Pat. No. 6,444,226, U.S. patent application Ser. Nos. 11/532,063 and 11/532,065 both filed on Sep. 14, 2006, and U.S. Provisional Patent Application Ser. No. 60/717,524, filed on Sep. 14, 2005. Each of these documents is incorporated herein by reference for all they contain regarding diketopiperazines, diketopiperazine microparticles and their use in drug delivery. Dry powders made according to these teachings work well for pulmonary delivery; however there remains room for improvement of various pharmaceutic properties. The present invention serves to overcome the need in the art for obtaining improved particles having superior aerodynamics and providing more efficient delivery and greater stability of the active agent.

SUMMARY OF THE INVENTION

The present invention is directed to methods of obtaining an improved particle and/or an improved dry powder. The particles and powders contemplated by the present invention are comprised of a diketopiperazine derivative combined with an active agent. In particular embodiments of the present invention, the particle is a diketopiperazine-insulin particle formulation having improved stability, aerodynamic properties, and pharmacodynamic properties when dried by the process of spray drying as compared to that of freeze drying. In other embodiments, there is provided a spray-dried diketopiperazine-insulin particle formulation or dry powder.

In a particular embodiment of the present invention, the particle comprising a diketopiperazine is prepared and provided in a suspension, typically an aqueous suspension, to which a solution of the active agent is added. Active agents of the present invention may include one or more of the following: insulin, calcitonin, parathyroid hormone 1-34, or other bioactive fragment of parathyroid hormone, octreotide, leuprolide, and RSV peptide, felbamate, cannabinoid antagonists and/or agonists, muscarinic antagonists and/or agonists, heparin, low molecular weight heparin, cromolyn, sildenafil, vardenafil, tadalafil growth hormone, zidovudine (AZT), didanosine (DDI), granulocyte-colony stimulating factor (GCSF), lamotrigine, chorionic gonadotropin releasing factor, luteinizing release hormone, β-galactosidase, GLP-1, exendins 1-4, ghrelin, and fragments thereof, but are not limited to such. In another embodiment, the active agent is a peptide or protein such as insulin or an analogue thereof.

In a particular embodiment, the active agent is insulin or an analogue thereof.

The present invention discloses methods of obtaining particles with improved aerodynamic performance and in which the active agent is more stable and efficiently delivered. More particularly, the present invention concerns methods for drying, particularly spray drying, diketopiperazine-insulin particles. The dry powders have utility as pharmaceutical formulations for pulmonary delivery. In other embodiments, the diketopiperazine-insulin dry powders may be utilized for nasal delivery.

Thus, in particular embodiments the present invention provides a method of preparing a dry powder medicament with an improved pharmaceutic property, comprising the steps of: (a) providing a solution of a diketopiperazine; (b) providing a solution of an active agent; (c) forming particles;

and (d) combining the diketopiperazine and the active agent; and thereafter (e) removing solvent by spray drying to obtain a dry powder, wherein the dry powder has an improved pharmaceutic property as compared to a dry powder obtained by removing solvent by lyophilization.

In another embodiment, the improved pharmaceutic property is selected from the group consisting of improved stability of the active agent, increased density of the dry powder, and improved aerodynamic performance of the dry powder. In still yet another embodiment, an improved aerodynamic performance of the dry powder is measured by the percentage of particles in the respirable range (respirable fraction) delivered from the inhaler. The respirable fraction, as contemplated in the present invention, may be greater than about 40% or greater than about 50%, or greater than about 60%, but is not limited to such.

In other embodiments of the present invention, it is contemplated that the insulin content of the microparticles is within the range of about 3% to about 50% by weight of the dry powder formulation. In other instances, the insulin concentration is within the range of about 7% to about 25% by weight. In preferred embodiments insulin content is about 19.0, 19.1, 19.2 19.3, 19.4, 19.5, 19.6, 19.7, 19.8, or 19.9% by weight. In another preferred embodiment, insulin concentration is at about 11% by weight. In still other preferred embodiments the insulin content is about 10, 12, 13, 14, 15, 16, 17, or 18% by weight. In various embodiments, about is defined as ±0.1, 0.2, 0.5, 1, or 2%, so long as the uncertainty does not exceed 10% of the insulin content.

In still yet another embodiment, there is provided in the present invention a diketopiperazine having the formula 2,5-diketo-3,6-di(4-X-aminobutyl)piperazine, wherein X is selected from the group consisting of succinyl, glutaryl, maleyl, and fumaryl. In a preferred embodiment, the diketopiperazine is fumaryl diketopiperazine.

In yet another particular embodiment of the present invention there is provided a dry powder prepared according to the method of preparing a dry powder medicament with an improved pharmaceutic property, comprising the steps of: (a) providing a solution of a diketopiperazine; (b) providing a solution of an active agent; (c) forming particles; and (d) combining the diketopiperazine and the active agent; and thereafter (e) removing solvent by spray drying to obtain a dry powder, wherein the dry powder has an improved pharmaceutic property as compared to a dry powder obtained by removing solvent by lyophilization. In a further embodiment, the dry powder comprises an active agent such as insulin or an analogue thereof, but is not limited to such.

In still yet another particular embodiment, the present invention provides a method for delivering insulin to a patient in need thereof, comprising administering to the patient an effective amount of the dry powder.

The present invention also provides a dry powder having an improved pharmaceutic property wherein the improved property is improved delivery of the active agent whereby greater glucose disposal is achieved.

In still yet another particular embodiment of the present invention, there is provided a method of preparing a dry powder medicament with an improved pharmaceutic property, comprising: (a) providing a diketopiperazine in solution; (b) a step for forming particles comprising the diketopiperazine; (c) and removing solvent by spray drying to obtain a dry powder, wherein the dry powder has an improved pharmaceutic property as compared to a dry powder obtained by removing solvent by lyophilization. A further step comprising loading the particle with an active agent prior to the solvent removal step is also provided.

Another particular embodiment of the present invention provides a method of optimizing the aerodynamic performance of a diketopiperazine dry powder comprising the steps of: (a) precipitating a diketopiperazine from solution under a controlled temperature to form particles; (b) selecting a drying method based on said temperature; and (c) drying the particles. A further step comprising loading the particles with an active agent is also contemplated.

In particular embodiments the inlet temperature during spray drying is 105° C., 110° C., 120° C., 130° C., 140° C., or a range bounded by any pair of these values. In other particular embodiments the atomization pressure is 0.4, 0.5, 0.6, 0.7, 0.8, 0.9, 1.0, 1.1 bar or a range bounded by any pair of these values. In further particular embodiments the spray rate is 4.4, 7.6, 12.2 g/min, or a range bounded by any pair of these values. In still another particular embodiment of the present invention the outlet temperature is 75° C.

In a further embodiment, the diketopiperazine is fumaryl diketopiperazine, wherein the controlled temperature is between about 15° C. to about 18° C. and the selected drying method is spray drying. In other embodiments the controlled temperature is about 17° C. In still other embodiments the controlled temperature is less than or equal to about 13° C. or greater than or equal to about 19° C.

In a further particular embodiments there is contemplated a particle containing about 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14.0%, 14.1%, 14.2%, 14.3%, 14.4%, 14.5%, 14.6%, 14.7%, 14.8%, 14.9%, 15.0%, 15.1%, 15.2%, 15.3%, 15.4%, 15.5%, 15.6%, 15.7%, 15.8%, 15.9%, 16.0% or greater, insulin by weight. In a particular embodiment of the present invention there is provided a particle containing about 11.4% insulin by weight. In another particular embodiment there is contemplated a particle comprising up to 50% insulin by weight.

The active agent such as, but not limited to, insulin, comprised in a solution or suspension, is mixed with a suspension of a diketopiperazine wherein, the solution or suspension is in a suitable solvent for both the active agent and the diketopiperazine In some embodiments, the present invention provides a method of obtaining a dry powder comprising a diketopiperazine and an active agent such as insulin, having improved pharmaceutical properties by precipitating the particles from a solution at a controlled temperature between about 15° C. to about 18° C. In other embodiments the controlled temperature is about 17° C. In still other embodiments the controlled temperature is less than or equal to about 13° C. or greater than or equal to about 19° C.

In other embodiments of the present invention the term 'Cartridge Fill Weight' as used herein refers to the quantity of drug product contained in a cartridge for an inhaler, typically 5-10 mg or more. In other embodiments the cartridge fill weight can vary from about 2.5 to 15 mg, 10 to 20 mg, or 5 to 30 mg.

In further embodiments the bulk or tapped density of the powder dried by spray drying is increased compared to a similar powder dried by lyophilization. In one such embodiment the density is greater by a factor of about 2 (1.7-2.3). Particular further embodiments include those limited to values disclosed in the examples or a range bounded by any pair of those values. In various embodiments the bulk density of the spray-dried powder is 0.150-0.200 g/cc.

Particular embodiments include those limited to values disclosed in the examples or a range bounded by any pair of those values. In various embodiments the tapped density of the spray-dried powder is 0.250-0.300 g/cc. Particular embodiments include those limited to values disclosed in the examples or a range bounded by any pair of those values.

In yet another embodiment of the present invention the term 'Cartridge Emptying' as used herein refers to the percentage (%) of powder that is discharged from the inhaler upon activation (or discharge). This value is typically obtained by weighing the cartridge before and after discharge. Particular embodiments include those limited to values disclosed in the examples or a range bounded by any pair of those values.

In still yet another embodiment of the present invention the term 'Respirable Fraction (RF)' as used herein refers to the percentage (%) of particles in the respirable range (0.5-5.8 μm). The 'Respirable Fraction (RF) delivered' refers to the percentage of active ingredient able to reach the airways of the lung where the pharmaceutical effect is exerted. Particular embodiments include those limited to values disclosed in the examples or a range bounded by any pair of those values.

In another embodiment of the present invention the term 'Respirable Fraction Based on Fill' ('RF Based on Fill', '% RF on Fill' or '% RF/fill') as used herein refers to the percentage (%) of powder in the respirable range normalized by the quantity of powder in the inhaler. Particular embodiments include those limited to values disclosed in the examples or a range bounded by any pair of those values.

BRIEF DESCRIPTION OF THE DRAWINGS

The following drawings form part of the present application and are included to further demonstrate certain aspects of the present invention. The invention may be better understood by reference to one or more of these drawings in combination with the detailed description of specific embodiments presented herein.

FIG. 2B depicts a corresponding decrease in the formation of A-21, the primary degradation product of insulin under these conditions. FIGS. 2C-2E demonstrate that the primary particles exhibit a decreased tendency to aggregate as the atomization pressure is increased from 0.4 bar (FIG. 2C) to 0.6 bar (FIG. 2D) to 0.7 bar (FIG. 2E). The measurements were obtained using laser diffraction.

FIG. 4A depicts the percent loss of insulin. FIG. 4B depicts formation of A-21, the most prevalent degradation product. FIG. 4C-4F depicts a trend towards increased aggregation of primary particles (as shown by the particles size distribution obtained from laser diffraction) as the inlet temperature is increased from 105° C. (FIG. 4C) to 120° C. (FIGS. 4D and 4E) to 140° C. (FIG. 4F).

FIGS. 5A-5E. Insulin distribution and particle morphology. FIG. 5A shows that insulin is evenly distributed throughout the formulation independent of particle size. FIGS. 5B-5E shows that the morphology of the spray-dried particles (FIGS. 5C and 5E) and lyophilized particles (FIGS. 5B and 5D) is the same.

FIGS. 6A-6B. Improvement in particle aerodynamics and insulin stability. FIG. 6A shows that % RF on Fill increases with atomization pressure at 0.7, 0.9 and 1.1 bar respectively. FIG. 6B shows that % RF on Fill does not change with inlet temperature at 110° C., 120° C. and 130° C. respectively.

FIG. 7A depicts measurement of the accelerated stability as percentage of insulin loss for powders spray dried at a pressure of 0.7 bar and inlet temperatures of 110° C., 120° C., and 130° C. respectively. FIG. 7B depicts measurement of the accelerated stability as percentage of insulin loss for powders spray dried at a pressure of 1.1 bar and inlet temperatures of 110° C., 120° C., and 130° C. respectively. FIGS. 7C-7K depicts minimal aggregation of primary particles (as shown by the particles size distribution obtained from laser diffraction) as the atomization pressure was varied from 0.7-1.1 bar and the inlet temperature was varied from 110° C., 120° C., and 130° C. respectively.

DETAILED DESCRIPTION OF THE EMBODIMENTS OF THE INVENTION

Figure 1:
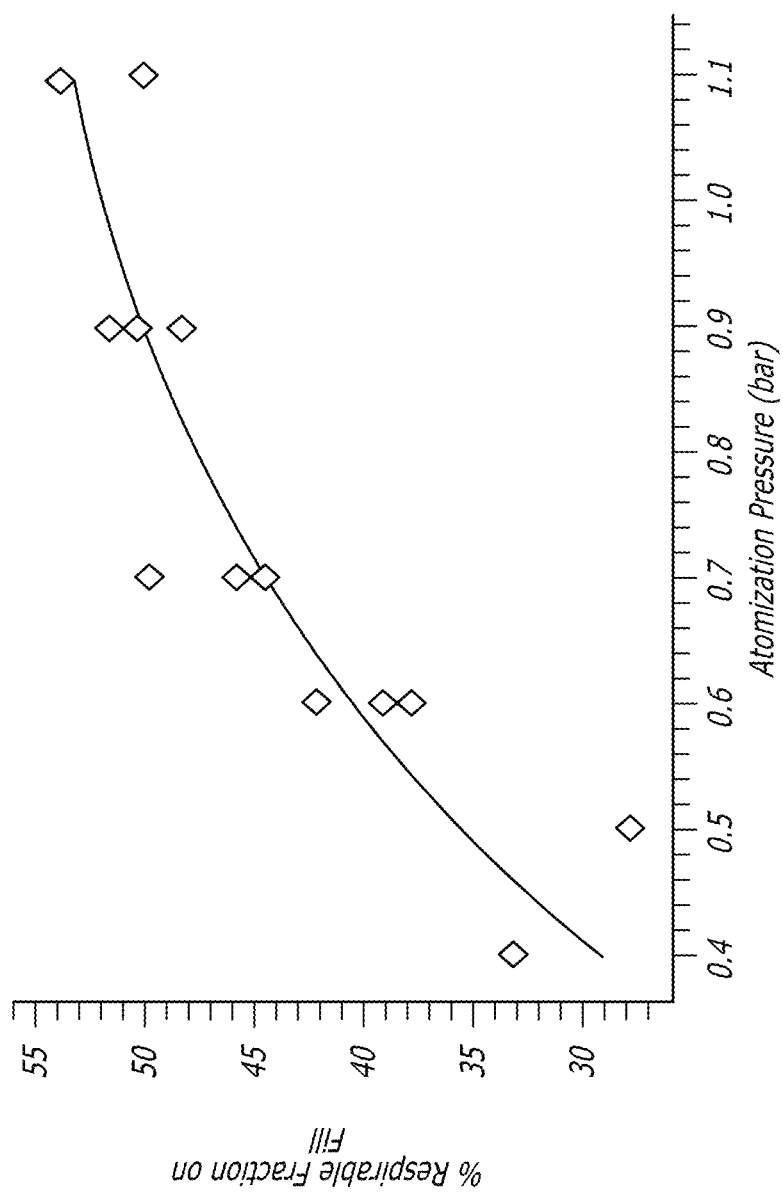
FIG. 1. Demonstration that increased atomization pressure had a positive effect on the aerodynamics of the diketopiperazine-insulin formulations. The inlet temperature ranged from 110° C. to 140° C. and the outlet temperature was held constant at 75° C.

The success of any pharmaceutic particle depends not only on its efficacy in treating a disease or condition, but also having superior pharmaceutic properties over other known therapeutics. Desirable pharmaceutic properties sought in a dry powder particle include improved aerodynamics, pharmacodynamics and stability. However, producing particles with such properties is an ongoing challenge in the art. One approach to achieving this aim in the art, lies in the methodology used to manufacture particles.

Thus, the present invention provides the novel and unexpected discovery that the pharmaceutic properties of the dry powder can be generally improved by using spray drying in preference to lyophilization to remove solvent from the particles.

The present invention serves to overcome the shortcomings in the art by providing particles of a diketopiperazine (DKP) combined with an active agent that are loaded and/or dried by a process to provide a dry powder having improved pharmaceutic properties. In particular embodiments, the present invention provides a particle, comprising a diketopiperazine combined with insulin, dried by spray drying. The invention further provides a spray-dried powder that demonstrates improved stability, aerodynamics or greater density, while maintaining at least similar pharmacodynamics as compared to the freeze-dried powder previously disclosed (see U.S. Pat. No. 6,444,226 entitled "Purification and Stabilization of Peptide and Protein Pharmaceutical Agents" and U.S. Patent Application Ser. Nos. 60/717,524, filed on Sep. 14, 2005 and Ser. No. 11/532,063 filed Sep. 14, 2006, both entitled "Method of Drug Formulation Based on Increasing the Affinity of Active Agents for Crystalline Microparticle Surfaces"), each incorporated herein by reference for all they contain regarding diketopiperazine microparticle compositions.

Diketopiperazine particles for drug delivery can be formed and loaded with active agent by a variety of methods. Diketopiperazine solutions can be mixed with solutions or suspensions of an active agent and then precipitated to form particles comprising the active agent. Alternatively the DKP can be precipitated to form particles and subsequently mixed with a solution of the active agent. Association between the particle and the active agent can occur spontaneously, be driven by solvent removal, a specific step can be included prior to drying, or any combinations of these mechanisms applied to promote the association. Further variations along these lines will be apparent to one of skill in the art.

In one particular protocol the precipitated diketopiperazine particles are washed, a solution of insulin is added, the mixture frozen by dropwise addition to liquid nitrogen and the resulting frozen droplets (pellets) lyophilized (freeze-dried) to obtain a diketopiperazine-insulin dry powder. In other embodiments, the mixture can be dispersed into the liquid nitrogen by other means, for example, by spraying. In other protocols the precipitated diketopiperazine particles of the invention are washed, a solution of insulin added, the pH of the solution adjusted to promote insulin adsorption onto the particles, and solvent removed either by spray drying or freeze drying to obtain a diketopiperazine-insulin dry powder. Previously, lyophilization had been used for solvent removal and it had been expected that the use of spray drying for this purpose would produce similar results. As disclosed herein, it was surprisingly discovered that spray-dried dry powder possessed improved pharmaceutical characteristics. In particular the spray-dried powder had an improved respirable fraction (% RF), the insulin contained in the particles had greater stability against degradation and the particles had a greater density allowing higher doses to be loaded into any particular volume. Upon pulmonary administration, at least comparable amounts of insulin were delivered into the bloodstream as evidenced by at least comparable reductions in blood glucose. The performance of the spray-dried powders was superior to the lyophilized powders whether or not the preparation of the lyophilized samples included a pH-adjustment to promote association of the drug with the particle.

In a further refinement of the methodology, the temperature of the solution from which the DKP was precipitated was controlled. Surprisingly, FDKP particles precipitated from solutions at temperatures about 13° C. or about 19° C., dry powders with greater % RF were obtained using lyophilization for solvent removal. For FDKP particles precipitated from solutions at temperatures at about 17° C., dry powders with greater % RF were obtained using spray drying for solvent removal. In the remaining portions of the tested range, aerodynamic performance was similar with either drying method. Thus aerodynamic performance of DKP particles can be optimized by selecting a solvent removal procedure on the basis of the temperature of the solution from which the particles are precipitated. The dry powders obtained were characterized for aerodynamic properties (% RF, cartridge emptying, % RF/fill, mass median aerodynamic diameter [MMAD], geometric standard deviation [GSD]) and physicochemical properties (insulin content [% load], yield, density) as described in examples provided herein.

Surprisingly, the density of the spray-dried particles was roughly twice that of freeze-dried particles. This can be advantageous in providing higher doses. Dry powder inhalers generally impose a limit on the volume of powder, and thus the dosage of active agent, that can be delivered in a single operation. A powder of higher density, but at least similar respirable fraction, allows larger doses to be administered in a single operation, rather than requiring more operations per dose, formulations with higher % loading of active agent, or alternate inhaler or inhaler cartridge designs to accommodate various volumes of powder. Any of these alternatives entail greater development and/or production costs and also introduce issues of product complexity. Product complexity and requirements for multiple operations per dose additionally create issues with product acceptance and patient compliance. Thus this unexpected increase in powder density offers multiple advantages for the use of spray-dried powders as pharmaceutical products.

1. Preparing Preformed Particles by Spray Drying

Spray drying, as employed in the present invention, is a thermal processing method used to load and/or dry particles in a suspension in a liquid medium (solvent). As disclosed in the examples herein, a suspension of diketopiperazine particles and an insulin solution are mixed. Some or all of the insulin molecules then bind to the diketopiperazine particles. In various embodiments the diketopiperazine-insulin particles are then loaded and/or dried by spray drying and a dry powder is obtained. In an alternative embodiment, the active agent is added to a diketopiperazine solution prior to precipitation of the particles.

During spray drying, the aqueous mixture of diketopiperazine particles or diketopiperazine-insulin particles, are introduced via a nozzle (e.g., a two fluid nozzle or high pressure nozzle), spinning disc, or an equivalent device into a heated gas stream. Prior to being passed through the heated gas stream, the solution or suspension is atomized into fine droplets. The heat energy supplied by the gas stream causes the evaporation of water and other solvents in which the particles are suspended, thereby producing dry powder compositions.

In obtaining a dry powder comprising a diketopiperazine combined with insulin, as in embodiments of the present invention, the inventors found that the spray drying method generally provided particles with superior pharmaceutic properties compared to similar particles obtained by freeze drying. In obtaining the particles, the inventors took into consideration a number of parameters. These parameters included temperature, atomization pressure, solids content of the suspensions, percent of insulin loss, formation of A-21, aggregation of particles, and aerodynamic and biological performance.

The inlet temperature is the temperature of the gas stream leaving its source. The outlet temperature is a measure of the final temperature of the powder formulation and an indication of the utilization of the energy in the inlet air for drying and is a function of the inlet temperature and the heat load required to dry the product, along with other factors. The outlet temperature is selected based upon the lability of the macromolecule being treated.

The diketopiperazine/active agent mixture may be a suspension. The solvent, generally water, rapidly evaporates from the droplets producing a fine dry powder.

Spray drying is performed under conditions that result in a powder of homogeneous constitution having a particle size that is respirable, with low moisture content and other characteristics that allow for aerosolization. Preferably the particle size of the resulting powder is such that more than about 98% of the particles (by mass) have a diameter of about 10 μm or less with about 90% of the particles (by mass) have a diameter less than 5 μm. Alternatively, about 95% of the particles (by mass) have a diameter of less than 10 μm with about 80% of the particles (by mass) have a diameter of less than 5 μm. In certain embodiments, the dry powder has a mean particle size of 1 to 5 μm in diameter. The preceding embodiments relate especially to use of the powder in pulmonary delivery. Mean particle size can effect where in the respiratory tract particles are deposited and can also effect their bulk handling properties. For example nasal deposition is favored for particles with mean diameters greater than 20 μm. In other embodiments, the powder may be used to form tablets, packaged in capsules, or resuspended for oral administration or injection. Thus in various embodiments, the dry powder may comprise particles having a mean particle size of greater than about 10 μm, 20 μm, 30 μm, 40 μm, 50 μm, 60 μm, 70 μm, 80 μm, 90 μm, 100 μm. In another embodiment, the dry powder may comprise particles having a mean particle size of about 100 μm to about 500 μm. In other embodiments, the dry powder may comprise particles having a mean particle size of less than about 1 mm.

Suspensions of the present invention, comprising an active agent and a diketopiperazine may be spray-dried in conventional spray drying equipment such as the PHARM-ASD™ PSD-1 Spray Dryer or the SD-Micro™ Spray Dryer, as are well known in the art and obtainable from a commercial supplier (Niro Inc., Columbia, Md.), thereby resulting in a dry powder comprised of such particles. It is noted that other conventional spray drying equipment may be used.

In conducting spray drying experimentation, methods such as rotary atomization, pressure atomization, and two-fluid atomization (for example, co-current two-fluid nozzle and/or fountain two-fluid nozzle) may be employed. Devices used in spray drying methodology are well known to one of ordinary skill in the art.

Although no special restrictions are placed on the nozzle of the atomizer used in the process of spraying, for a nozzle which can produce a spray-dry composition with a grain diameter suitable for nasal pharyngeal or pulmonary administration it is recommended in the art to use nozzles such as those in the following examples. For example, nozzle types "1A," "1," "2A," "2," "3" and the like, (manufactured by Yamato Chemical Co.), or the SB Series SprayDry® Nozzles (manufactured by Spraying Systems Co.), can be used with the spray-dryer. In addition, disks type "MC-50," "MC-65" or "MC-85," (manufactured by Okawara Kakoki Co.), can be used as rotary disks of the spray-drier atomizer.

In other embodiments, the inlet gas temperature used to dry the sprayed material is such that it does not cause heat deactivation of the active agent. The range of inlet temperatures may vary between about 50° C. to about 200° C., preferably between about 110° C. and 160° C. With well-stabilized agents, the inlet temperature can exceed 200° C. The temperature of the outlet gas used to dry the sprayed material may vary between about 35° C. and about 100° C., preferably between 55° C. and 85° C. In other embodiments, the outlet temperature may be preferably at 75° C. In another embodiment of the present invention, the inlet and outlet temperatures may be held at 120° C. and 75° C. respectively.

As disclosed above and elsewhere herein, terminology useful and applicable to the methods and compositions of the present invention are as follows:

The term "powder" means a composition that consists of fine solid particles that are capable of being dispersed in an inhalation device and inhaled by a subject. In preferred embodiments the particles reach the lungs or alveoli. Such a powder is said to be "respirable." Preferably the average particle size is less than about 10 microns (μm) in diameter with a relatively uniform spheroidal shape distribution. More preferably the diameter is less than about 7.5 μm and most preferably less than about 5.0 μm. Usually, the particle size distribution is between about 0.1 μm and about 8 μm in diameter, particularly about 0.3 μm to about 5 μm.

The term "dry" means that the powder composition is not suspended or dissolved in a propellant, carrier, or other liquid. It is not meant to imply a complete absence of water. The composition can have a moisture content such that the particles are readily dispersible in an inhalation device to form an aerosol. This moisture content is generally below about 10% by weight (% w) water, usually below about 5% weight and preferably less than about 3% weight.

The term "effective amount" is the amount that is needed to provide a desired response in the subject to be treated. The precise dosage will vary according to a variety of factors including, but not limited to, the age and size of the subject, the disease and the treatment being effected. The "effective amount" will also be determined based on the anticipated pharmacodynamic response or bioavailability.

2. Diketopiperazines

Diketopiperazines can be formed into particles that incorporate an active agent or particles onto which an active agent can be adsorbed. Diketopiperazines of the present invention include but are not limited 3,6-di(fumaryl-4 aminobutyl)-2,5-diketopiperazine also known as (E)-3,6-bis[4-(N-carboxyl-2-propenyl)amidobutyl]-2,5-diketopiperazine (which may also be referred to as fumaryl diketopiperazine or FDKP).

Other diketopiperazines that are contemplated in the present invention include 3,6-di(4-aminobutyl)-2,5-diketopiperazine; 3,6-di(succinyl-4-aminobutyl)-2,5-diketopiperazine (succinyl diketopiperazine or SDKP); 3,6-di(maleyl-4-aminobutyl)-2,5-diketopiperazine; 3,6-di(citraconyl-4-aminobutyl)-2-5-diketopiperazine; 3,6-di(glutaryl-4-aminobutyl)-2,5-diketopiperazine; 3,6-di(malonyl-4-aminobutyl)-2,5-diketopiperazine; 3,6-di(oxalyl-4-aminobutyl)-2,5-diketopiperazine and derivatives therefrom.

In brevity, diketopiperazines can be formed by cyclodimerization of amino acid ester derivatives, as described by Katchalski, et al., (J. Amer. Chem. Soc. 68:879-80; 1946), by cyclization of dipeptide ester derivatives, or by thermal dehydration of amino acid derivatives in high-boiling solvents, as described by Kopple, et al., (J. Org. Chem. 33(2): 862-64; 1968), the teachings of which are incorporated herein.

Methods for synthesis and preparation of diketopiperazines are well known to one of ordinary skill in the art and are disclosed in U.S. Pat. Nos. 5,352,461; 5,503,852; 6,071, 497; 6,331,318; and 6,428,771; and U.S. patent application Ser. No. 11/208,087 each of which is incorporated herein by reference for all they teach regarding diketopiperazines. U.S. Pat. No. 6,444,226, herein incorporated by reference for all it contains regarding diketopiperazine microparticles, describes preparing and providing microparticles of diketopiperazines in aqueous suspension to which a solution of active agent is added. This patent further describes a method of removing a liquid medium by lyophilization to yield microparticles comprising an active agent. See also U.S. Pat. No. 6,440,463 and U.S. patent application Ser. Nos. 11/532,063 and 11/532,025 both filed on Sep. 14, 2006, and U.S. Provisional Patent Application Ser. No. 60/717,524, filed on Sep. 14, 2005; each of which is incorporated herein by reference for all they teach regarding diketopiperazine microparticles.

In one embodiment, active agent is encapsulated within microparticles by dissolving a diketopiperazine with acidic side chains in bicarbonate or other basic solution, adding the active agent in solution or suspension, and then precipitating the microparticle by adding acid, such as 1 M citric acid. In another embodiment, active agent is encapsulated within microparticles by dissolving a diketopiperazine with basic side chains in an acidic solution, such as 1 M citric acid, adding the active agent in solution or suspension, and then precipitating the microparticle by adding bicarbonate or another basic solution. In still another embodiment, active agent is encapsulated within microparticles by dissolving a diketopiperazine with both acidic and basic side chains in an acidic or basic solution, adding the active agent in solution or suspension to be encapsulated, then precipitating the microparticle by neutralizing the solution. In an alternative embodiment, microparticles of diketopiperazine are prepared and provided in a suspension, typically an aqueous suspension, to which a solution of the active agent then is added.

It is further contemplated that the diketopiperazine-insulin particle formulations of the present invention can be administered by various routes of administration. As dry powders these particles can be delivered by inhalation to specific areas of the respiratory system, depending on particle size. Additionally, the particles can be made small enough for incorporation into an intravenous suspension dosage form. Oral delivery is also possible with the particles incorporated into a suspension, tablets, or capsules.

3. Active Agents

Embodiments of the present invention employ particles combining an active agent with a diketopiperazine. The term 'active agent' is referred to herein as the therapeutic agent, or molecule (such as protein or peptide or biological molecule), to be encapsulated, associated, joined, complexed or entrapped in or to the diketopiperazine of the present invention. Generally speaking, any form of an active agent can be combined with a diketopiperazine of the present invention. Active agents, as contemplated in the present invention, may or may not be charged.

Active agents contemplated for use in the compositions and methods described herein may include any polymer or large organic molecules, most preferably peptides and proteins. Examples include synthetic organic compounds, proteins and peptides, polysaccharides and other sugars, lipids, and nucleic acid sequences, having therapeutic, prophylactic, or diagnostic activities. Active agents may also include small molecules and vitamins. An active agent of the present invention may also be a vasoactive agent, a neuroactive agent, a hormone, an agent regulating metabolism, weight, or blood glucose levels, an anticoagulant, an immunomodulating agent, a cytotoxic agent, an antibiotic, an antiviral, an antisense molecule, or an antibody.

Examples of specific exemplary active agents have been listed above. In particular embodiments of the invention the active agent is insulin or an analogue thereof. Analogues with faster, slower, shorter, or longer action profiles are known in the art. Such analogues include those with altered amino acid sequences and those that have been covalently modified with other moieties, such as polyethylene glycol, or additional amino acids, such as in a fusion protein. Ultimately any molecule with a substantial portion of a wild type insulin molecule and physiologically relevant insulin activity is comprehended by this term.

Proteins as contemplated by the present invention are defined as consisting of 100 amino acid residues or more; in addition, peptides contemplated by the invention are less than 100 amino acid residues.

4. Stabilizing Agents Contemplated in the Present Invention

In further embodiments, there is contemplated by the present invention the use of stabilizing agents that may be contained in a suspension or solution comprising a diketopiperazine and an active agent which may be incorporated into the particle formulation.

Stabilizing agents may be included for conformational stability during the drying process. In addition, these stabilizing agents may further improve the aerodynamics or bioavailability of the dry powder diketopiperazine-insulin particle formulations of the present invention. Such stabilizing agents may comprise, but are not limited to, sugars, surface modifying agents, surfactants, hydrophobic amino acids such as tryptophan, tyrosine, leucine, phenylalanine, pharmaceutical carriers or excipients, and the like.

Stabilizing agents contemplated by the present invention are those preferably suitable for respiratory and pulmonary administration. In certain embodiments, it is preferred that the stabilizing agent be incorporated simultaneously into the diketopiperazine-insulin particle to produce a homogeneous powder. Alternatively, the stabilizing agent may be separately prepared in a dry powder form and combined with the spray dried diketopiperazine-insulin particle by blending.

In other instances, powder carriers may be employed such as, but not limited to carbohydrates, e.g., monosaccharides such as fructose, galactose, glucose, D-mannose, sorbose, and the like; disaccharides, such as lactose, trehalose, cellobiose, and the like; cyclodextrins, 2-hydroxypropyl-β-cyclodextrin; and polysaccharides, such as raffinose, maltodextrins, dextrans, and the like; amino acids, such as glycine, arginine, aspartic acid, glutamic acid, cysteine, lysine, and the like; organic salts prepared from organic acids and bases, such as sodium citrate, sodium ascorbate, magnesium gluconate, sodium gluconate, tromethamine hydrochloride, and the like; peptides and proteins, such as aspartame, human serum albumin, gelatin, and the like; alditols, such as xylitol, and the like. A preferred group of carriers may include trehalose, raffinose, maltodextrins, glycine, sodium citrate, tromethamine hydrochloride, human serum albumin, and mannitol. Such powder carriers will usually be crystalline (to avoid water absorption), but might in some cases be amorphous or mixtures of crystalline and amorphous forms. The size of the stabilizing agent particles may be selected to improve the flowability of the spray dried powder product.

Sugars as contemplated by the present invention include, but are not limited to, dextrose, lactose, and mannitol.

Surfactants as contemplated by the present invention include, but are not limited to, polysorbate 80 (PS80), lecithin, phosphatidylcholine, DPPC, sodium dodecylsulfate, and ionic detergents.

5. Method for Coating Microparticles

The procedure for coating crystalline microparticles, such as preformed crystalline microparticles, with active agents is described generally as follows: crystalline microparticles previously formed by precipitation, or another method, are suspended in liquid medium, such as water; and the medium is adjusted to alter the particles' surface either before or after addition of active agent. At this point the active agent will adsorb to the microparticle surface and after an interval of time (for example <1, 1, 2, 3, 4, 5, 6, 7, 8, 9, or 10 minutes; preferably from <1 to at least 5 minutes) the loading process will be complete. The liquid medium may then be removed by spray-drying.

6. Promoting Adsorption of Active Agents

Adsorbing active agent to the surface of a crystalline microparticle can involve altering the properties of the active agent in a solution or fluid suspension under various solution conditions, thereby promoting adsorption to the microparticle surface and reducing the amount of active agent remaining in solution. Alteration or modifications to the active agent may occur with the use of modifiers such as, but not limited to, chaotropes and kosmotropes, salts, organics such as, but not limited to, alcohols, osmolytes, and surfactants. These modifiers can act on the active agent to alter its chemical potential and thereby its structure, flexibility, rigidity or stability, without chemically altering the agent itself. The term "chemical potential" is well known to one of ordinary skill. In embodiments of the present invention, "chemical potential" refers to the free energy necessary to drive a chemical reaction such as, for example, interaction between an active agent and a solvent or the adsorption of active agent onto a microparticle. The term "energetically favorable" as used herein refers to the lowering of the free energy levels of the adsorbed states of the active agent onto the microparticle in relation to the free energy level of uncoated microparticle, or unbound active agent and/or the insoluble forms (including aggregation or precipitation) of the active agent. The term "structure" as used herein refers to the secondary structure of the active agent molecule and includes the alpha-helical formation, beta sheets, or random coil (unordered) of the active agent molecule, such as a protein. Additionally, the term structure may also include teritary and quaternary structures of the molecule but is not limited to such and may also refer to the self association, aggregation, multimerization, dimerization, and the like, of a molecule. The term "stability" as used herein refers to the stabilization or destabilization of the structure of the active agent in the presence of the modifier.

In addition, altering the properties of the active agent in a solution or fluid suspension are likely to affect the interactions due to hydrophobic properties, hydrogen bonding properties, and electrostatic properties of the active agent and/or microparticle.

Hydrophobic interactions are associations of non-polar groups with each other in aqueous solutions because of their insolubility in water. Hydrophobic interactions can affect a number of molecular processes including, but not limited to, structure stabilization (of single molecules, complexes of two or three molecules, or larger assemblies) and dynamics, and make important contributions to protein-protein and protein-ligand binding processes. These interactions are also known to play a role in early events of protein folding, and are involved in complex assembly and self-assembly phenomena (e.g., formation of membranes).

Hydrogen bonding interactions are especially strong dipole-dipole forces between molecules; a hydrogen atom in a polar bond (e.g., H—F, H—O or H—N) can experience an attractive force with a neighboring electronegative molecule or ion, which has an unshared pair of electrons (typically an F, O, or N atom on another molecule). Hydrogen bonds are responsible for the unique properties of water and are very important in the organization of biological molecules, especially in influencing the structure of proteins and DNA.

Electrostatic interactions are attractions between opposite charges or repulsions between like charges that grow stronger as the charges come closer to each other. Electrostatic interactions constitute a key component in understanding interactions between charged bodies in ionic solutions. For example, the stability of colloidal particles dispersed in a solvent can be explained by considering the competition between repulsive electrostatic interactions and the attractive van der Waals interactions. Electrostatic interactions are also of importance when considering interaction and adhesion between particles.

7. Manipulating Microparticle Surface Properties

As disclosed elsewhere herein, the surface properties of the microparticle can be manipulated by various means. The microparticle surface properties that can be manipulated include, but are not limited to, electrostatic, hydrophobic, and hydrogen bonding properties. In various embodiments these manipulations are carried out in the absence or presence of the active agent, or before or after the microparticles and the active agent are mixed together. When the manipulation takes place in the presence of the active agent, for example by altering solution condition, there can also be effects on the active agent that will modify its affinity for the surface. Thus in some embodiments of the present invention, coating of the microparticle can involve manipulation of surface properties and modification of properties of the active agent. Methods directed to the latter are disclosed in U.S. Pat. No. 7,803,404 entitled METHOD OF DRUG FORMULATION BASED ON INCREASING THE AFFINITY OF ACTIVE AGENTS FOR CRYSTALLINE MICROPARTICLE SURFACES and which is incorporated herein by reference in its entirety.

Electrostatic interactions are attractions between opposite charges or repulsions between like charges that grow stronger as the charges come closer to each other. Electrostatic interactions constitute a key component in understanding interactions between charged bodies in ionic solutions. For example, the stability of colloidal particles dispersed in a solvent can be explained by considering the competition between repulsive electrostatic interactions and the attractive van der Waals interactions. Also, the chemical functionality (for example, but not limited to COOH, NH, etc.) of the microparticle surface can be utilized as the counter ion to an ionized active agent such that the active agent/particle composite comprises a salt. Electrostatic interactions are also of importance when considering interaction and adhesion between particles.

Altering the pH of the surrounding solution system can change electrostatic properties of ionizable crystalline microparticles in suspension. Changing the pH of the solution changes the ionization of a microparticle such that active agent adsorbs to the microparticle surface. Microparticles composed of FDKP (3,6-bis[N-fumaryl-N-(n-butyl) amino]2,5-diketopiperazine) are ionizable. The microparticles are insoluble in water below pH 3.5 but solubility increases rapidly between pH 3.5 and 5.0, presumably due to the ionization of the carboxyl groups. The FDKP microparticle is partially ionized at pH 5 prior to complete dissolution at higher pH, which can be observed indirectly via ultrasonic spectroscopy. In one embodiment, diketopiperazine microparticles are suspended in an acidic solution, active agent is added to the suspension, and the pH of the solution is raised after the active agent and microparticles are mixed together. The increased pH alters the surface properties of the microparticles to create an environment in which the active agent has a higher affinity for the microparticle than for the solvent.

Alternatively, the pH of the microparticle suspension can be raised immediately prior to addition of active agent to the solution. The surface charge properties of the microparticle are altered by the change in pH such that active agent has a higher affinity for the microparticle than for remaining in solution and is adsorbed to the microparticle surface upon addition.

8. Other Methods of Manipulating the Surfaces of Microparticles

In addition to electrostatic properties, other properties of a microparticle surface can be exploited to control adsorption of active agent. Microparticles containing compounds with imidazole, pyridine, Schiff bases, ketone, carboxylic acid bioisosteres, amides, or other functional groups that can exist in multiple structures could be manipulated to modify surface properties.

Hydrophobic interactions are associations of non-polar groups with each other in aqueous solutions because of their insolubility in water. Hydrophobic interactions can affect a number of molecular processes including, but not limited to, structure stabilization (be it of single molecules, complexes of two or three molecules, or larger assemblies) and dynamics, and make important contributions to protein-protein and protein-ligand binding processes. These interactions are also known to play a role in early events of protein folding, and are involved in complex assembly and self-assembly phenomena (e.g., formation of membranes).

Hydrophobic interactions can be manipulated by changing the protonation of crystalline microparticles composed of histidine. Protonating the histidine will reduce the nucleophilicity of the crystalline microparticles and impart a positive charge.

Hydrogen bonding interactions are especially strong dipole-dipole forces between molecules; a hydrogen atom in a polar bond (e.g., H—F, H—O or H—N) can experience an attractive force with a neighboring electronegative molecule or ion, which has an unshared pair of electrons (usually an F, O or N atom on another molecule). Hydrogen bonds are responsible for the unique properties of water and are very important in the organization of biological molecules, especially in influencing the structure of proteins and DNA.

In the present invention, the hydrogen bonding properties of the microparticle surface can be controlled by chemical derivatization. Hydrogen bond donors/acceptors can be added chemically to alter the microparticle surface. For example, the hydrogen in an N—H bond can undergo hydrogen bonding to the oxygen in a C=O bond. If the N—H is replaced by an N—CH$_3$, then this particular hydrogen bonding interaction is removed. Likewise, replacement of the C=O group with a C=C group also removes this particular bonding interaction.

Microparticles with surfaces containing ionizable aromatic groups are polar when ionized but hydrophobic in their un-ionized state. Starting with protonated surfaces and manipulating solution conditions to reduce particle surface ionization causes hydrophobic or aromatic active agents to coat the microparticle surface.

Microparticles with ketone surface groups could be manipulated by changing the solution polarity. By reducing solvent polarity (adding low polarity organic solvents to an aqueous solution) the enol-form is made the predominant species at the particle surface. This enol-form is a hydrogen bond donor whereas the keto-form is a hydrogen bond acceptor. The adsorption of nitrogen-containing drugs onto the microparticle surface is promoted in this manner.

Microparticles with surface groups that undergo pH- or temperature-induced isomerization can also be induced to adsorb drug molecules by manipulating solution conditions. In the case of these surfaces, the introduction of a kink in a linear surface group due to isomerization increases the mobility (fluidity) of the groups at the microparticle surface. This allows the surface to form more contacts with the active agent than are possible with an ordered surface. If the additional interactions with the active agent are each favorable, then the net interaction energy becomes favorable and the drug adsorbs to the microparticle surface.

EXAMPLES

The following examples are included to demonstrate preferred embodiments of the present invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Effect of Atomization Pressure on Aerodynamics, Stability, and Aggregation

Diketopiperazine derivative, 3,6-bis[N-fumaryl-N-(n-butyl)amino]-2,5-diketopiperazine (also referred to as 3,6-di(fumaryl-4 aminobutyl)-2,5-diketopiperazine, fumaryl diketopiperazine or FDKP; also termed (E)-3,6-bis[4-(N-carboxy-2-propenyl)amidobutyl]-2,5-diketopiperazine) were precipitated and washed. Insulin was loaded onto the FDKP particles by adjustment to a pH of approximately 4.45, and the FDKP-insulin particles were spray dried to obtain a FDKP-insulin dry powder. A pH of about 4.45 was found to increase the binding of insulin to FDKP particles as disclosed in U.S. patent application Ser. Nos. 11/532,063 and 11/532,025 both filed on Sep. 14, 2006, and U.S. Provisional Patent Application Ser. No. 60/717,524, filed on Sep. 14, 2005.

The dry powders were characterized for various aerodynamic properties (% RF, cartridge emptying, % RF/fill, mass median aerodynamic diameter [MMAD], and geometric standard deviation [GSD]).

Table 1 and FIG. 1 demonstrate the effect of the atomization (nozzle) pressure on the aerodynamic performance of the particles. The nozzle pressures ranged from 0.4 bar to 1.1 bar (Table 1). The respirable fraction on fill (% RF on Fill) improved as the atomization pressure was increased from 0.4 bar to 1.1 bar.

TABLE 1

Effect of atomization pressure on aerodynamic properties. Outlet temperature was 75° C.

| Atomization Pressure (bar) | Inlet T (° C.) | % RF delivered | % Cartridge Emptying | % RF fill | MMAD (μm) | GSD |
|---|---|---|---|---|---|---|
| 0.4 | 105 | 34.7 | 95.5 | 33.1 | 2.7 | 2.2 |
| 0.5 | 105 | 30.3 | 92.1 | 27.9 | 3.3 | 2.3 |
| 0.6 | 105 | 39.4 | 95.6 | 37.7 | 2.5 | 2.3 |
|  | 120 | 45.5 | 91.9 | 41.8 | 2.7 | 2.2 |
|  | 120 | 45.4 | 92.2 | 41.9 | 2.5 | 2.2 |
|  | 140 | 42.4 | 91.4 | 38.8 | 2.5 | 2.2 |
| 0.7 | 105 | 48.2 | 92.7 | 44.7 | 2.7 | 2.2 |
|  | 110 | 71.9 | 68.9 | 49.5 | 2.3 | 2.0 |
|  | 120 | 57.7 | 77.6 | 44.8 | 2.5 | 2.0 |
|  | 130 | 63.5 | 71.6 | 45.5 | 1.9 | 2.0 |
| 0.9 | 110 | 68.4 | 70.2 | 48.0 | 2.3 | 2.0 |
|  | 120 | 68.3 | 74.9 | 51.2 | 2.1 | 2.0 |
|  | 130 | 55.4 | 90.2 | 49.9 | 2.7 | 2.0 |
| 1.1 | 110 | 64.2 | 84.0 | 54.0 | 2.5 | 1.9 |
|  | 120 | 70.4 | 70.8 | 49.8 | 2.0 | 2.0 |
|  | 130 | 71.7 | 74.9 | 53.7 | 2.2 | 2.0 |

Figure 2A:
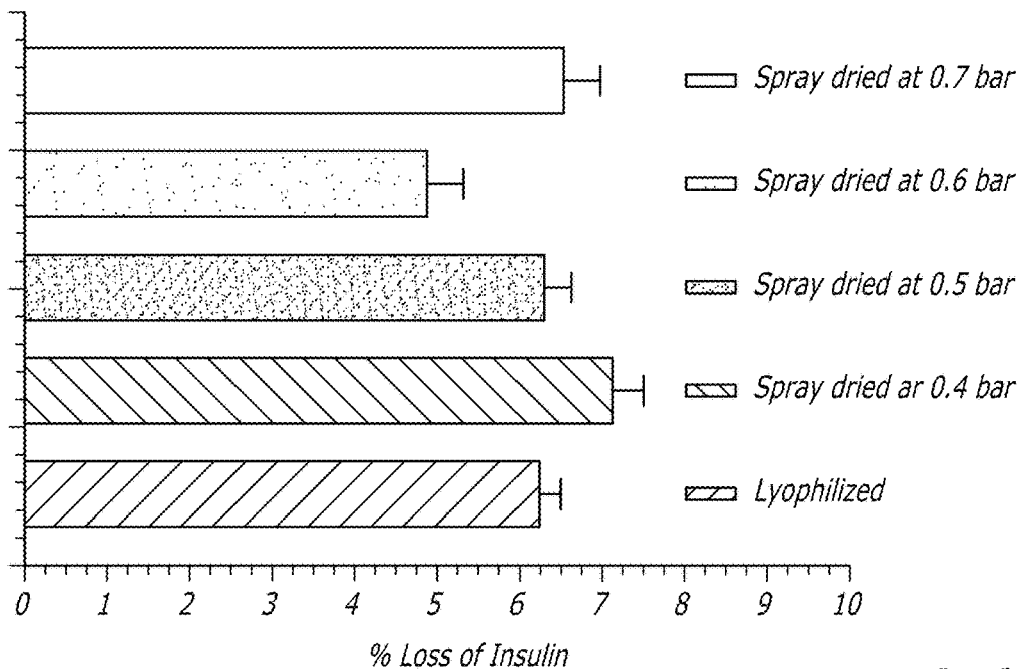
FIGS. 2A-2E. Evaluation of the accelerated stability of diketopiperazine-insulin formulations. The accelerated stability conditions were 40° C. and 75% RH (relative humidity) for 10 days. A reduction in insulin loss in the spray-dried formulations is depicted in FIG. 2A.
Figure 2B:
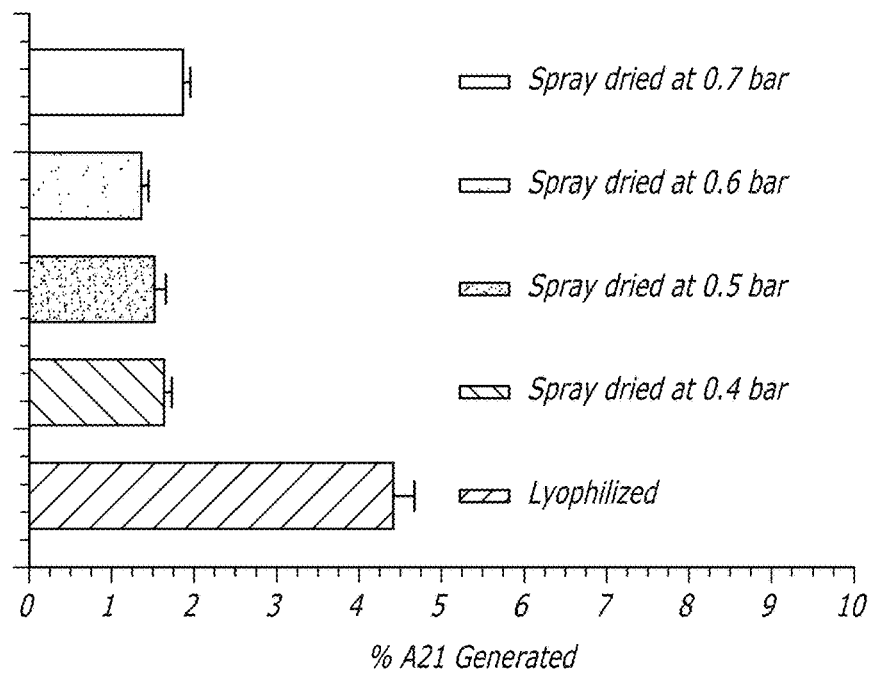

The stability of the insulin was assessed as the percent loss of insulin (FIG. 2A) and the percent conversion to insulin degradation product A21-desamido insulin (% A21) under stress conditions (10 days at 40° C., 75% RH) (see FIG. 2B). For comparison, the bottom bar in each figure represents data obtained with freeze dried particles. The data demonstrate that, as the atomization pressure was increased, there was a general trend toward increased stability of the insulin in the diketopiperazine-insulin particles. Less formation of the A21 insulin degradation product was observed in all of the spray-dried particles as compared to freeze-dried particles (FIG. 2B).

Figure 2C:
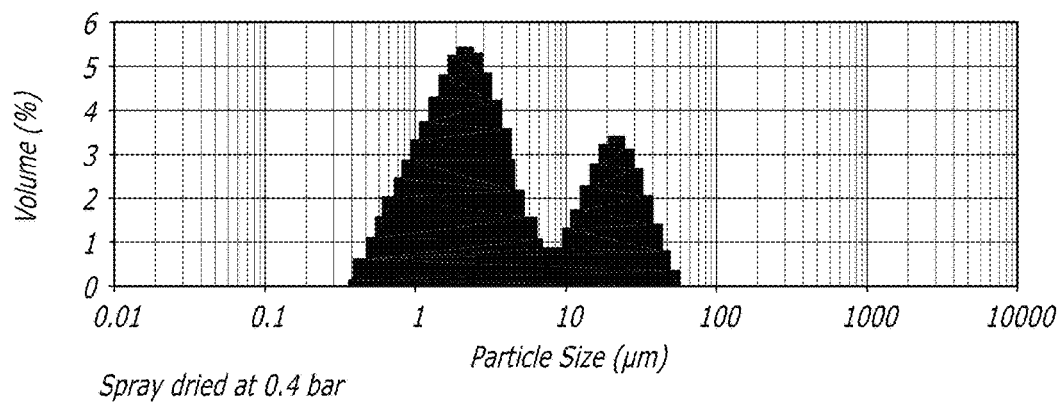
Figure 2D:
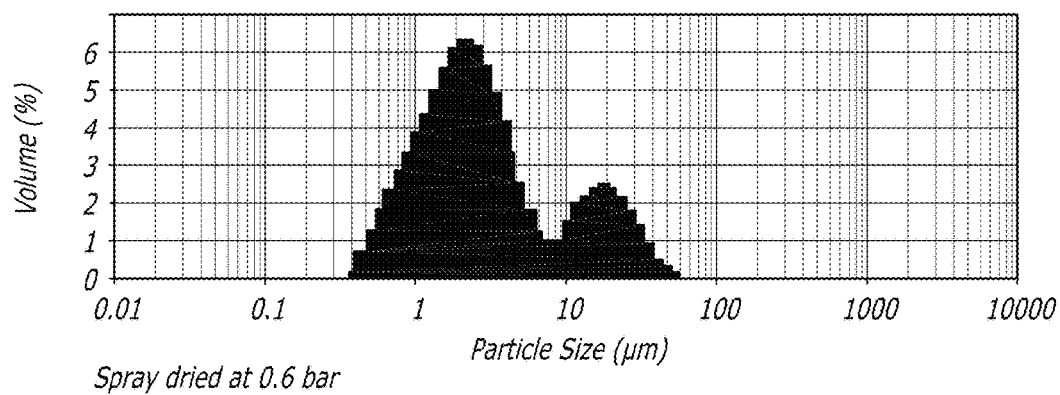
Figure 2E:
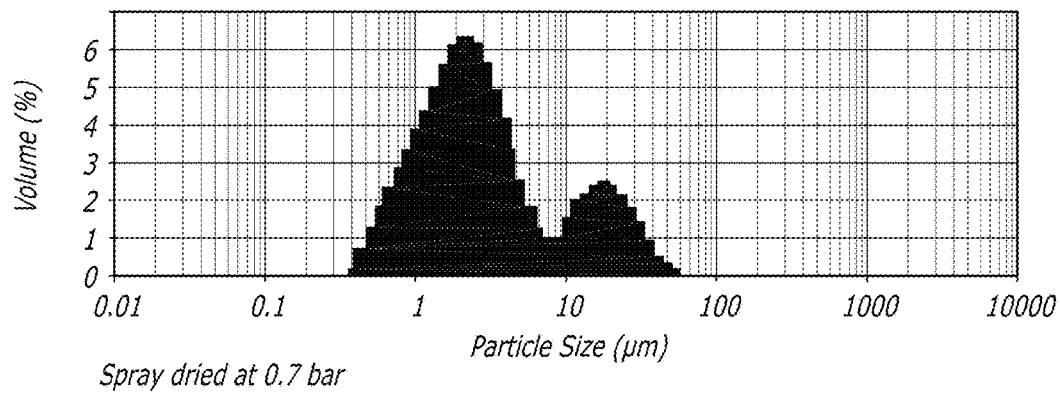

To assess aggregation of the primary particles, the particle size distribution was determined from laser diffraction of a suspension of spray-dried particles using a Malvern Mastersizer 2000. Under the above trial conditions, a trend towards decreased aggregation of the primary diketopiperazine-insulin particles was observed with increased atomization pressure (FIGS. 2C-2E). It is observed that the size of the peak to the right, representing aggregated particles, decreases as the atomization pressure increases from 0.4 bar (FIG. 2C) to 0.6 bar (FIG. 2D), to 0.7 bar (FIG. 2E).

Example 2

Effect of Inlet Temperatures on Aerodynamics, Stability, and Particle Aggregation Using particles prepared as above, spray dryer inlet temperature and process scalability were evaluated as shown in Table 2 below. In these experiments, the inlet temperature was varied from 105° C. to 140° C. and the outlet temperature was held constant at 75° C. The nozzle pressure was held constant at 0.6 bar.

Figure 3:
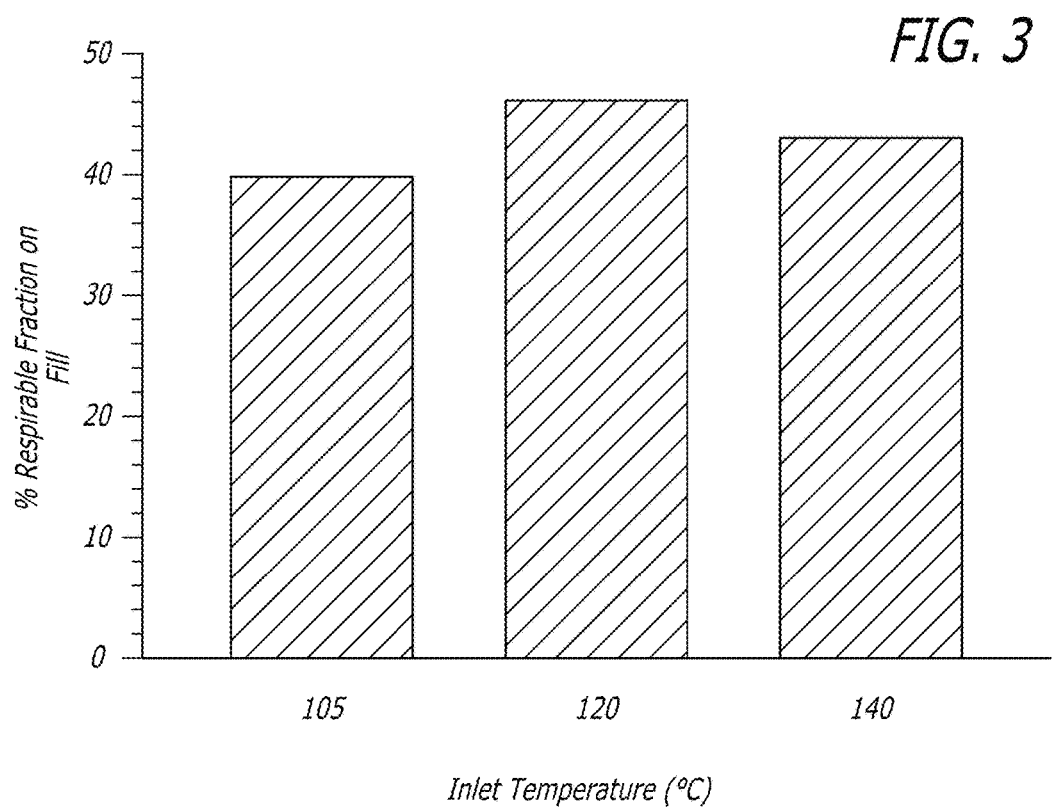
FIG. 3. Demonstration of the effect of temperature on the aerodynamics of the diketopiperazine-insulin formulations. The outlet temperature was held at 75° C. and the atomization pressure was held at 0.6 bar. The % RF on Fill (percent respirable fraction on a cartridge fill) remained relatively consistent over the temperature range.

It was observed that the increased inlet temperatures required an increase in the spray rate to maintain a consistent outlet temperature (Table 2). The increased spray rates produced dried particles at a greater production rate. The aerodynamics of the spray dried particles were assessed (Table 2). The % RF on Fill remained consistent over the temperature range studied (FIG. 3).

TABLE 2

Effect of inlet temperature on particle aerodynamics. Nozzle pressure was maintained at 0.6 bar and the outlet temperature was 75° C.

| Scale (g) | Spray Rate (g/min) | Inlet Temp. (° C.) | % RF | % cartridge emptying | % RF on Fill | MMAD (μm) | GSD |
|---|---|---|---|---|---|---|---|
| 11.3 | 4.4 | 105 | 39.4 | 95.6 | 37.7 | 2.5 | 2.3 |
| 11.3 | 7.6 | 120 | 45.5 | 91.9 | 41.8 | 2.7 | 2.2 |
| 45.2 | 7.6 | 120 | 42.4 | 91.4 | 38.8 | 2.5 | 2.2 |
| 11.3 | 12.2 | 140 | 45.4 | 92.2 | 41.9 | 2.5 | 2.2 |

Figure 4A:
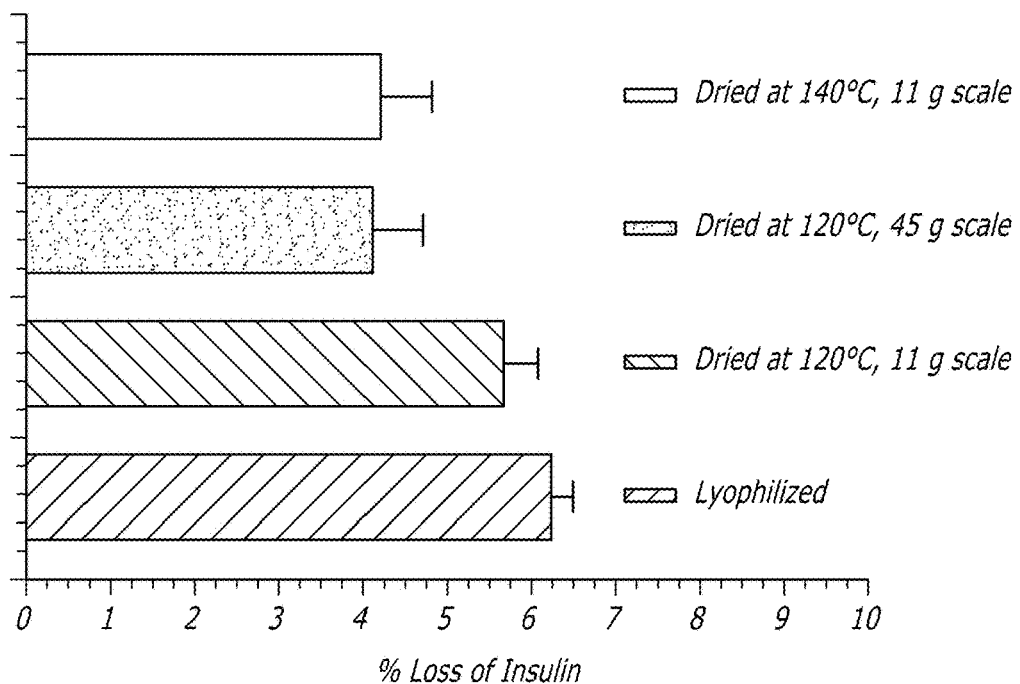
FIGS. 4A-4F. Demonstration that increased inlet temperature (drying rate) did not negatively impact the stability of the formulations. The accelerated stability conditions were 40° C. and 75% RH for 10 days.
Figure 4B:
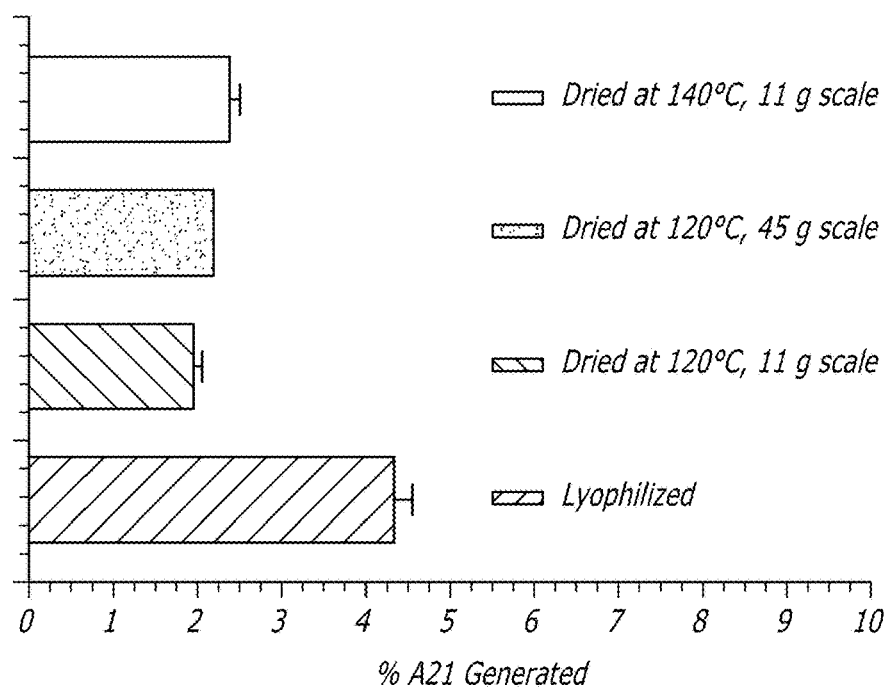
Figure 4C:
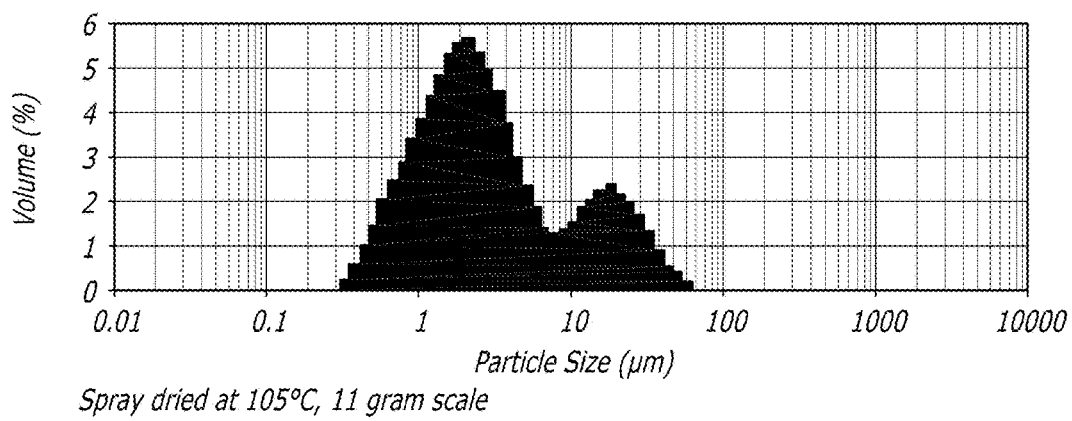
Figure 4D:
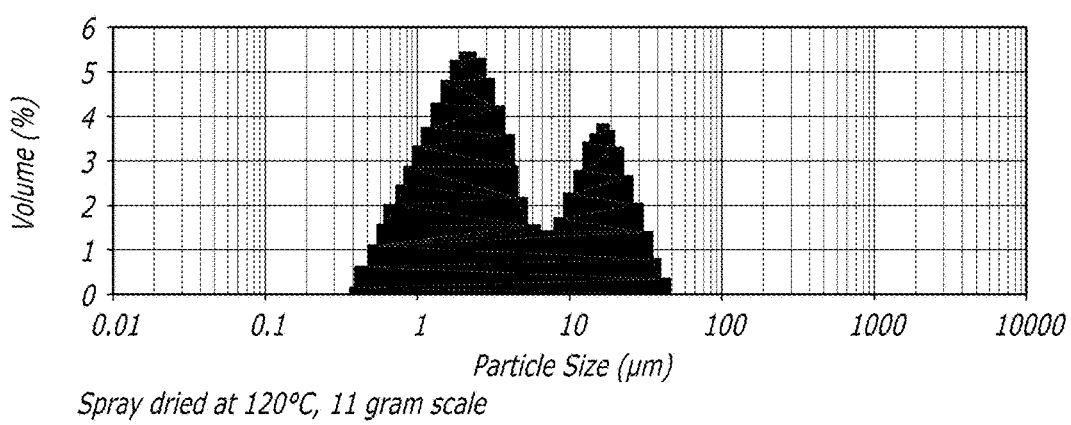
Figure 4E:
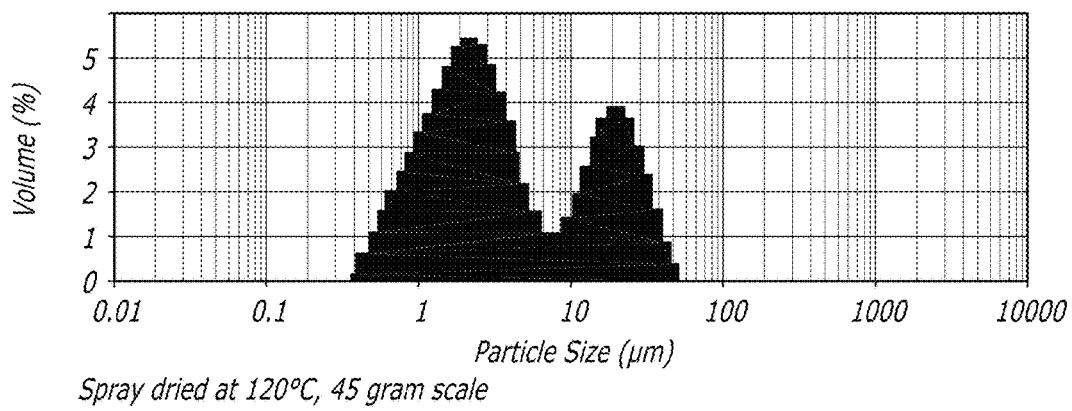
Figure 4F:
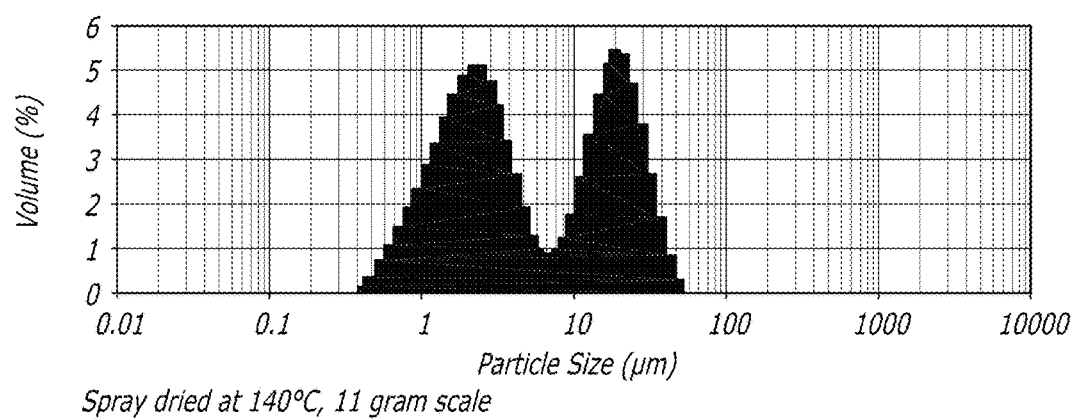

Further, the data demonstrated that increasing the inlet temperature (drying rate) did not negatively impact the stability of the insulin on the particles. There was a trend toward increased insulin stability with increasing inlet temperature. Stability was measured as insulin lost and A21 formed (FIGS. 4A and 4B) after 10 days at 40° C./75% RH. However, under the above trial conditions, a trend toward increase aggregation of the primary diketopiperazine-insulin particles was observed with an increase in the inlet temperature (FIGS. 4C-4F).

Example 3

Insulin Recovery and Distribution

In these experiments, a known mass of diketopiperazine particles was suspended in water. Enough insulin solution of known concentration was added to the suspension to give a theoretical composition of 11.4% insulin. The fumaryl diketopiperazine-insulin slurry was titrated to a pH of approximately 4.45 prior to spray drying.

Insulin distribution across particles was assessed as shown in FIG. 5A. These experiments were conducted using an Andersen Cascade Impactor. The powder was filled into cartridges and discharged through a MedTone® inhaler into the Andersen cascade impactor. (The MedTone® inhaler is described in U.S. patent application Ser. No. 10/655,153 entitled "Unit Dose Cartridge and Dry Powder Inhaler" which is incorporated herein by reference for all it contains regarding the inhaler device). The impactor classifies the particles by aerodynamic size. After discharge, the powder was recovered from each stage and assayed for insulin content (load). Insulin is shown to be evenly distributed throughout the formulation. Increasing the scale (grams of the powder), as shown in Table 2 above, by a factor of 4 was also found to be acceptable.

Particle morphology of the spray-dried and lyophilized particles was compared by scanning electron microscopy (SEM). FIG. 5B-5E shows the particle morphologies for the lyophilized formulation (FIGS. 5B and 5D) are comparable to those for the spray-dried formulation (FIGS. 5C and 5E).

Summary of Examples 1-3

The above data, show that: 1) increasing the atomization pressure decreased the aggregation of the primary particles; 2) increasing the inlet temperature had little impact on the particles aerodynamics; 3) increasing the inlet temperature was not observed to have a negative impact on the stability of the insulin; 4) increasing the inlet temperature resulted in greater aggregation of the primary particles; 5) spray-dried particles had increased insulin stability when compared to lyophilized particles of identical composition; and 6) spray-dried particles had similar morphology as lyophilized particles.

Example 4

Determination of Spray-Drying Parameters to Maximize Aerodynamic Performance Inlet temperature and atomization pressure were further evaluated using inlet temperatures of 110, 120 and 130° C. and atomization pressures of 0.7, 0.9, and 1.1 bar (Table 3).

TABLE 3

Effect of spray-drying parameters on particle aerodynamics

| Atomization pressure (bar) | Inlet Temperature (° C.) | % RF | % Cartridge emptying | % RF on fill | MMAD (µm) | GSD |
| --- | --- | --- | --- | --- | --- | --- |
| 0.7 | 110 | 71.9 | 68.9 | 49.5 | 2.3 | 2.0 |
| 0.7 | 120 | 57.7 | 77.6 | 44.8 | 2.5 | 2.0 |
| 0.7 | 130 | 63.5 | 71.6 | 45.5 | 1.9 | 2.0 |
| 0.9 | 110 | 68.4 | 70.2 | 48.0 | 2.3 | 2.0 |
| 0.9 | 120 | 68.3 | 74.9 | 51.2 | 2.1 | 2.0 |
| 0.9 | 130 | 55.4 | 90.2 | 49.9 | 2.7 | 2.0 |
| 1.1 | 110 | 64.2 | 84.0 | 54.0 | 2.5 | 1.9 |
| 1.1 | 120 | 70.4 | 70.8 | 49.8 | 2.0 | 2.0 |
| 1.1 | 130 | 71.7 | 74.9 | 53.7 | 2.2 | 2.0 |

FIG. 6A summarizes the results of Table 3 as the % RF on fill versus the atomization pressure; FIG. 6B summarizes the results as % RF on fill versus the inlet temperature. Thus, the data show that increasing atomization pressure leads to improved aerodynamic performance and inlet temperature does not affect this parameter.

Example 5

Figure 7A:
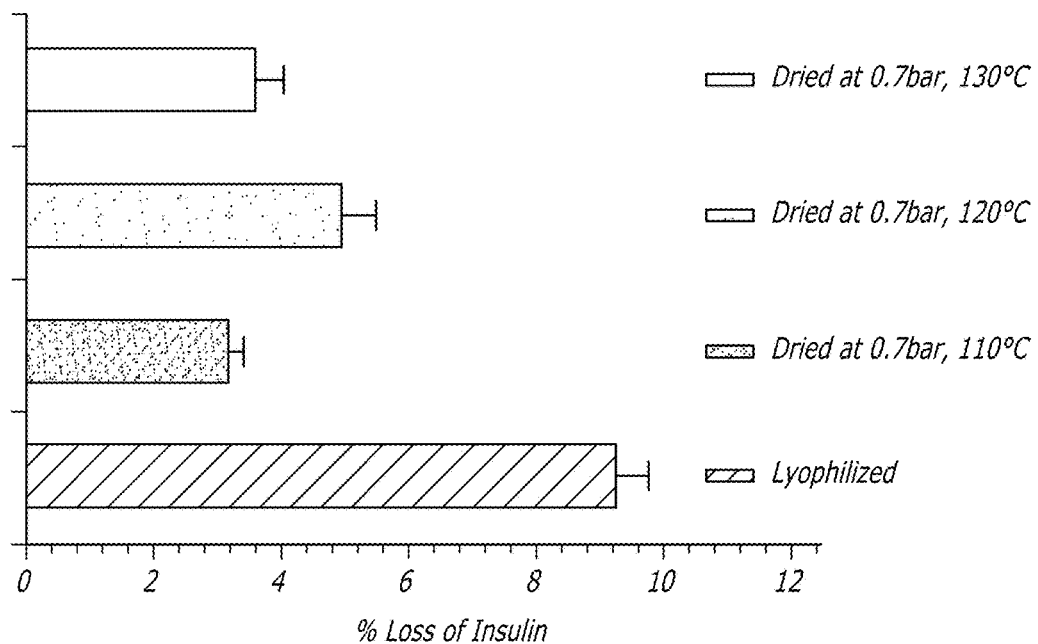
FIGS. 7A-7K. Demonstration that insulin stability increases at higher inlet temperatures and atomization pressures.
Figure 7B:
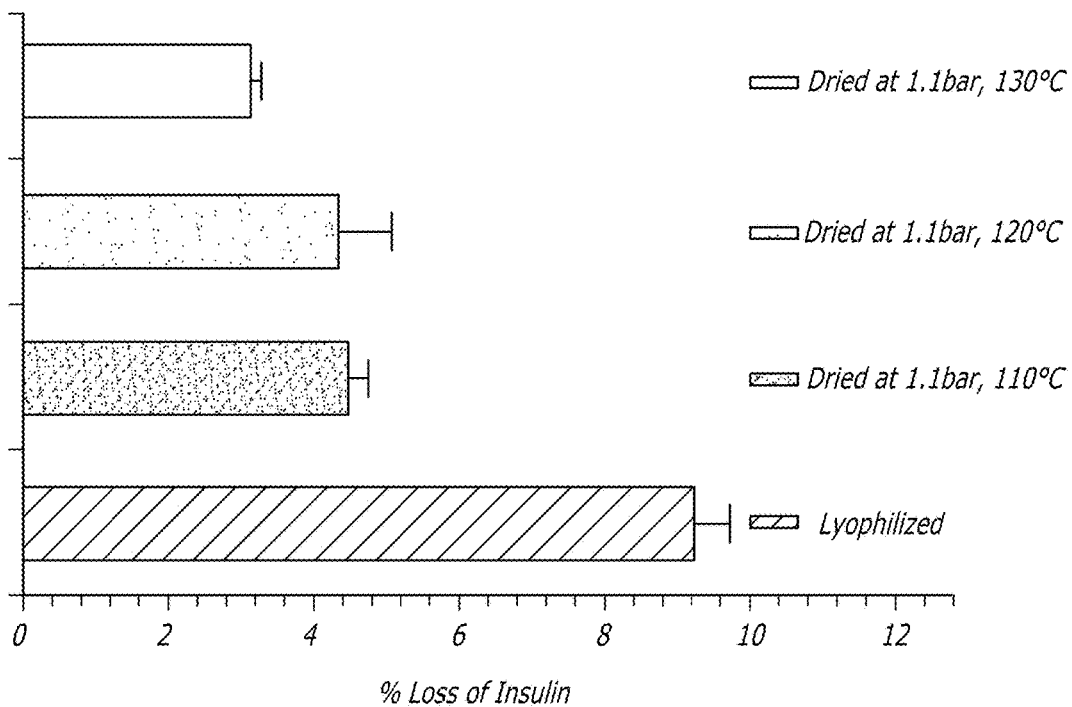
Figure 7C:
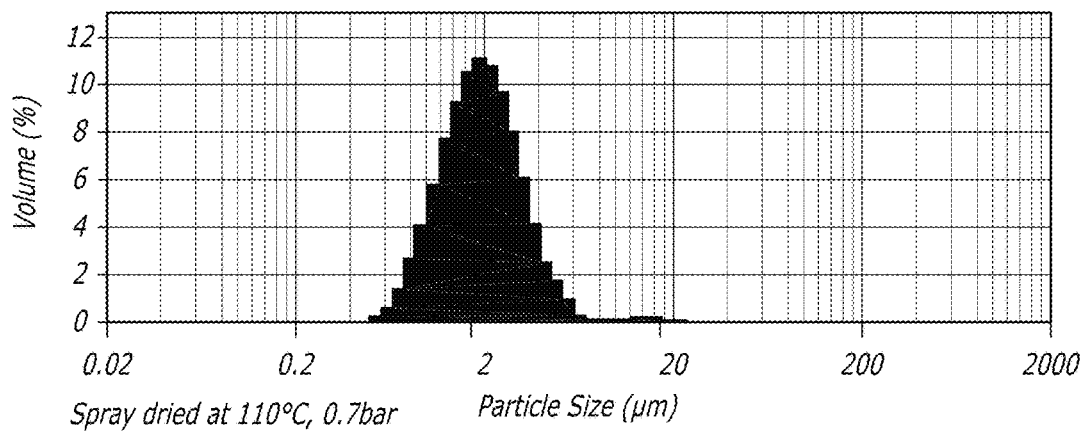
Figure 7D:
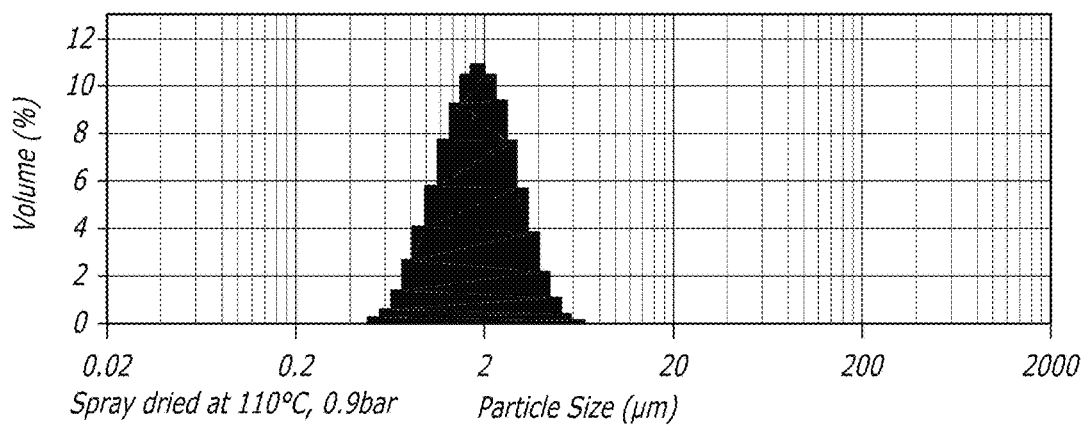
Figure 7E:
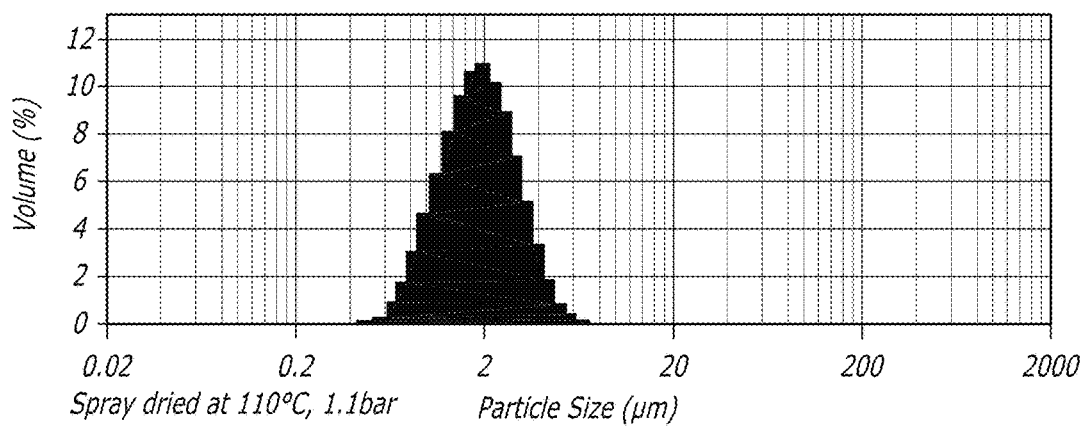
Figure 7F:
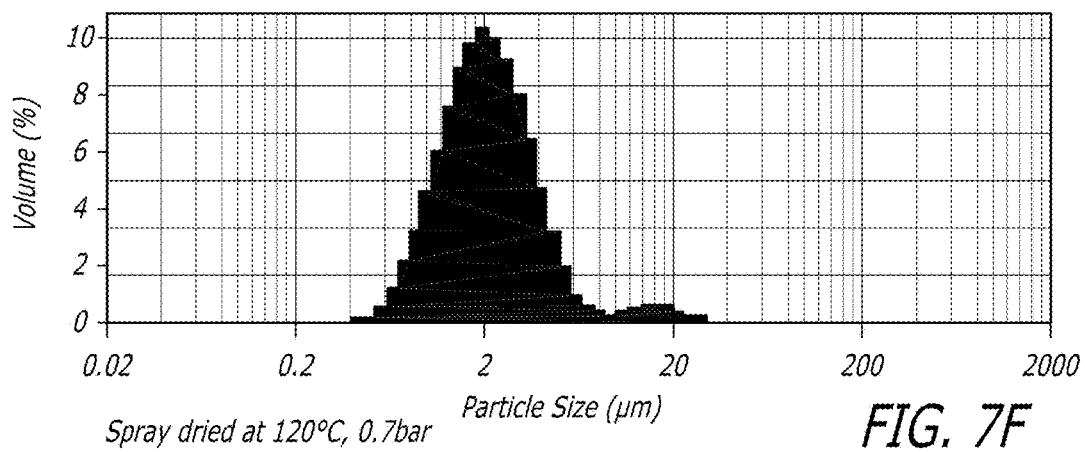
Figure 7G:
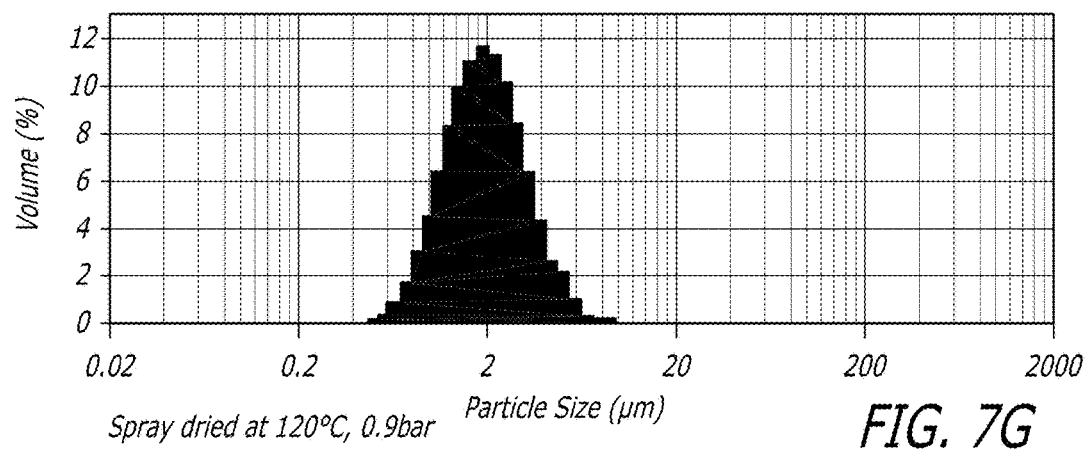
Figure 7H:
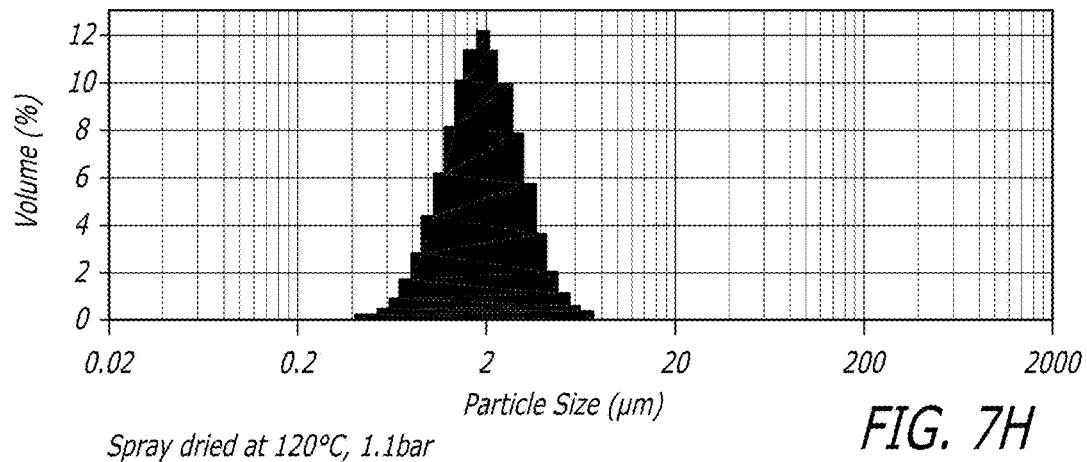
Figure 7I:
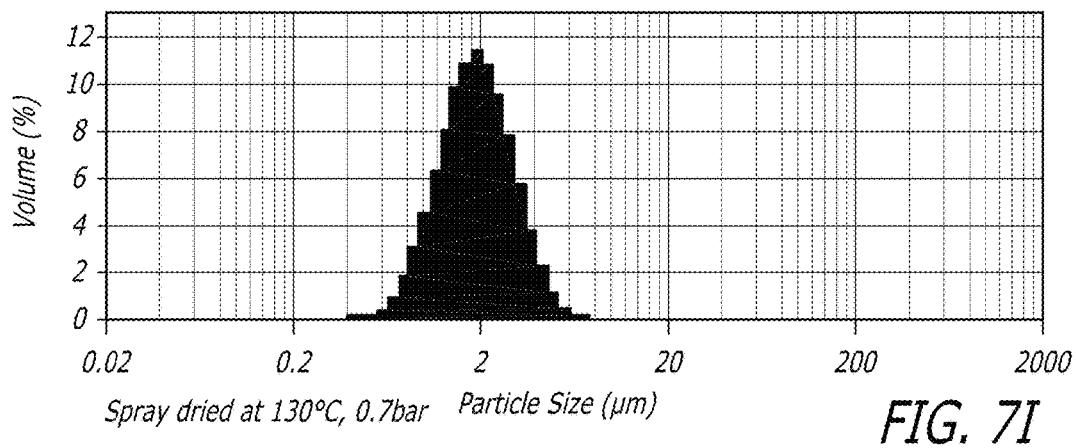
Figure 7J:
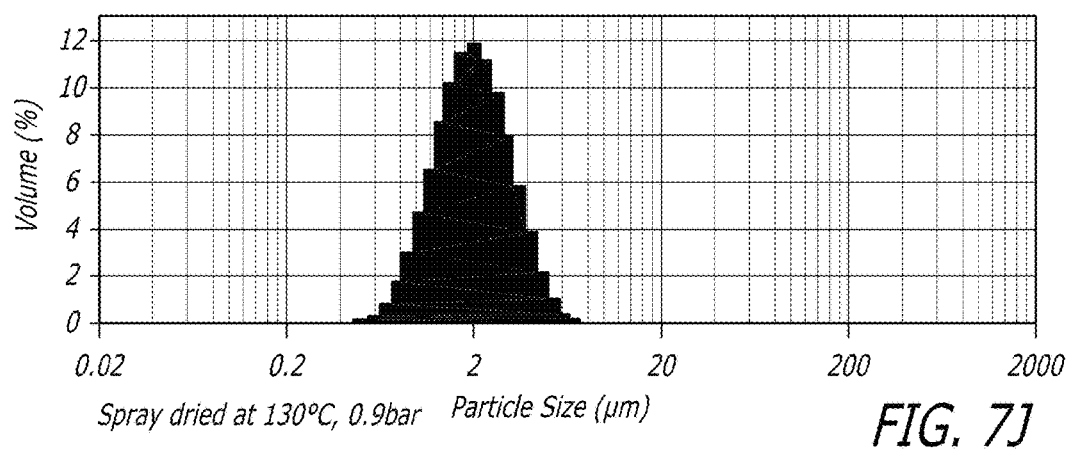
Figure 7K:
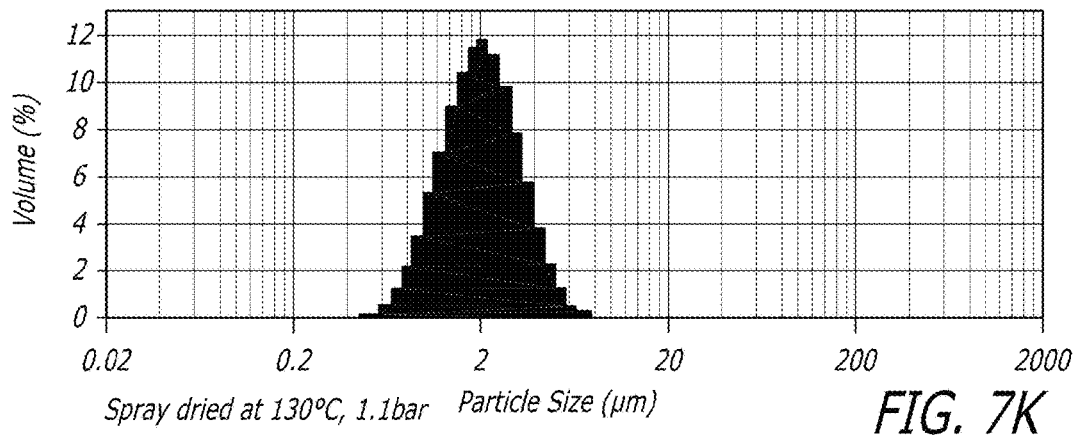

Effect of Inlet Temperature and Atomization Pressure on Stability and Aggregation The samples listed in Table 3 were analyzed for insulin stability and particle aggregation. As shown in FIGS. 7A and 7B, the results were consistent with those of Examples 1-3 in that the spray-dried samples showed less insulin loss than comparable lyophilized powders (the bottom bar in FIGS. 7A and 7B; loading of the particles used in the lyophilized samples included adjustment to pH 4.5, which as discussed in Example 1 above, increases the binding of insulin to FDKP particles).

The aggregation of the primary diketopiperazine-insulin particle was assessed under the conditions of increased inlet temperature and increased atomization pressure (FIGS. 7C-7K) The particle size distributions by laser diffraction were generally insensitive to atomization pressure and temperature over the ranges covered in this example. A small degree of aggregation was observed at 0.7 bar and inlet temperatures of 110° C. and 120° C., but a unimodal distribution was obtained at all other conditions.

The results for the spray-dried samples as compared to the lyophilized samples show: 1) the atomization pressure can be increased to improve aerodynamics; 2) the inlet temperature has negligible effect on % RF on Fill; 3) insulin stability increases with increased inlet temperature; and 4) the increased inlet temperature and atomization pressure reduced aggregation of the primary insulin particles.

Example 6

Insulin Pharmacodynamics with Spray-Dried Particles

Figure 8:
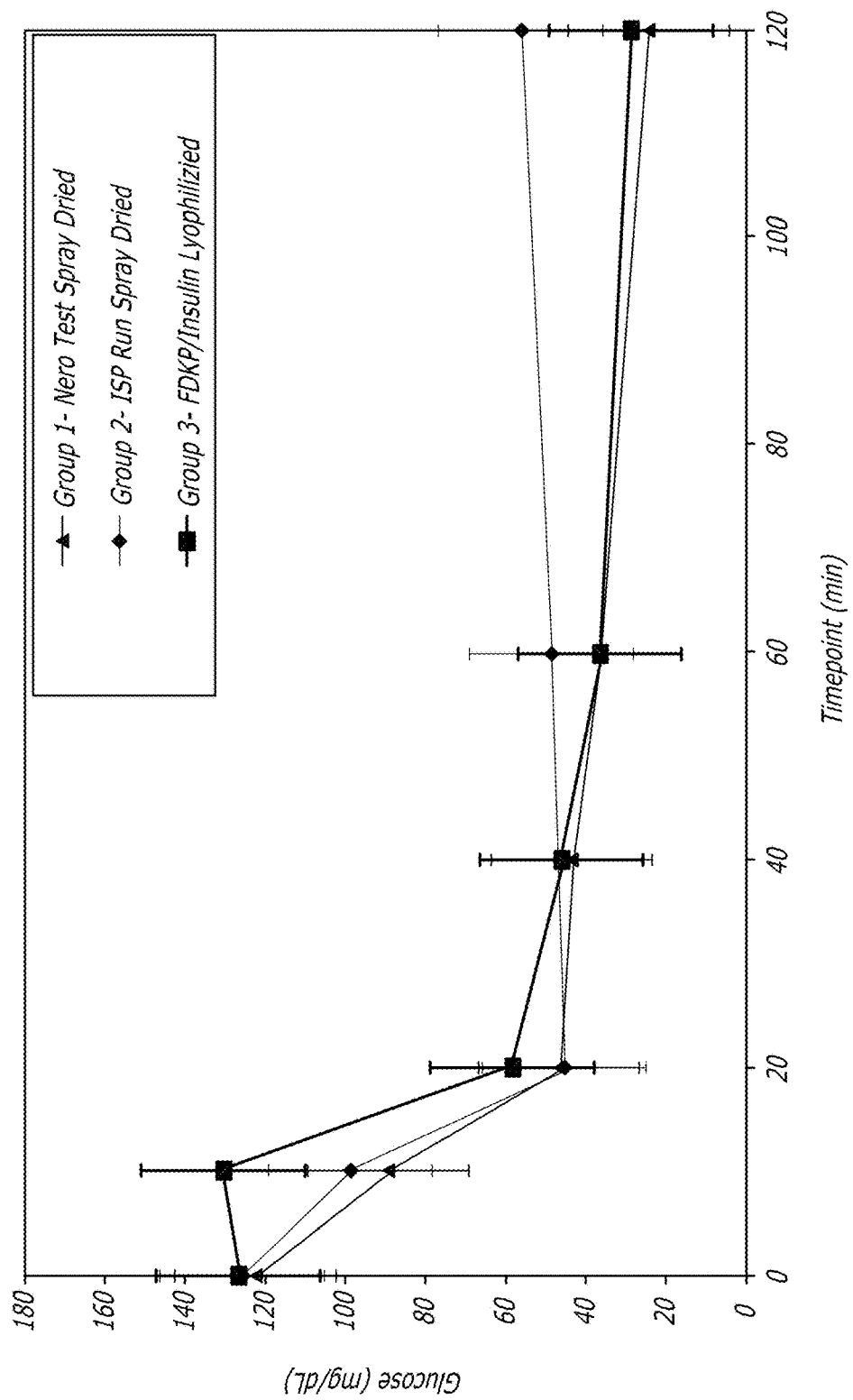
FIG. 8. Comparison of pharmacodynamic profiles (blood glucose reduction) following insufflation of 11.4% lyophilized FDKP/Insulin and 11.4% spray dried FDKP/Insulin in rats. Each animal received 3 mg of powder containing 11.4% insulin by weight. Each group contained 4 animals.

Data from a rat insufflation study indicated that spray-dried FDKP-insulin powder provides at least comparable glucose disposal as provided by lyophilized material. FIG. 8 shows a comparison of pharmacodynamic profiles (blood glucose reduction) following insufflation of lyophilized and spray-dried 11.4% FDKP-insulin particles in rats. The glucose lowering capacity of spray-dried FDKP-insulin powder was found to be equivalent to that of lyophilized FDKP-insulin powder.

Example 7

Aerodynamics and Stability of Spray-Dried FDKP-Insulin Powder

Fumaryl diketopiperazine (FDKP)-insulin particles were prepared in a manner similar to that described above. That is, particles were mixed with an insulin solution to give particles containing 11.4% insulin by weight, and then the pH adjusted to promote insulin adsorption onto the particles. The resulting particle suspensions were dried by either spray drying or lyophilization. Table 4 shows the comparison of two 200 g lots prepared using a commercial scale spray dryer with similar lyophilized samples. The bulk powders were tested for aerodynamic performance. Additional samples of bulk powders were stored at 40° C./75% RH for 15 days prior to evaluation for insulin loss and formation of A21-desamido insulin. The spray dried powder displayed an average respirable fraction on fill (% RF/fill) of 62%; compared to an average value of 54% for the lyophilized powder. The spray-dried powder also demonstrated superior stability. Insulin loss and A-21 formation of the spray-dried powder were about half that of the lyophilized powder.

TABLE 4

Aerodynamics and stability of spray dried FDKP-insulin powder

| Manufacturing Process | Andersen cascade impactor | | | Accelerated stability | |
| --- | --- | --- | --- | --- | --- |
| | % RF | % Cartridge Emptying | % RF/fill | % Insulin Lost | % A-21 Formed |
| Lyophilized (average of two lots*) | 55 | 98 | 54 | 16.98 | 6.32 |
| Spray dried (average of two lots*) | 66 | 94 | 62 | 8.83 | 2.63 |

*Lots were prepared in a similar manner.

Example 8

Characterization of Spray-Dried Vs Lyophilized FDKP-Insulin Powders

In a further refinement of the process, the feed temperature of the FDKP solution was controlled. Stock solutions of fumaryl diketopiperazine (FDKP) were prepared and cooled to 11° C., 13° C., 15° C., 17° C., or 19° C. and the FDKP particles were precipitated. Two different strategies were employed for loading and drying particles. In one strategy, the precipitated diketopiperazine particles were washed, an insulin solution was added and the pH adjusted to promote adsorption of insulin onto the particle, the mixture was frozen by dropwise addition to liquid nitrogen, and the resulting pellets were lyophilized (freeze-dried) to obtain a diketopiperazine-insulin dry powder. In another parallel protocol the precipitated diketopiperazine particles were washed, an insulin solution was added, the pH adjusted, and the diketopiperazine-insulin particle suspension was spray-dried to obtain a diketopiperazine-insulin dry powder.

Figure 9:
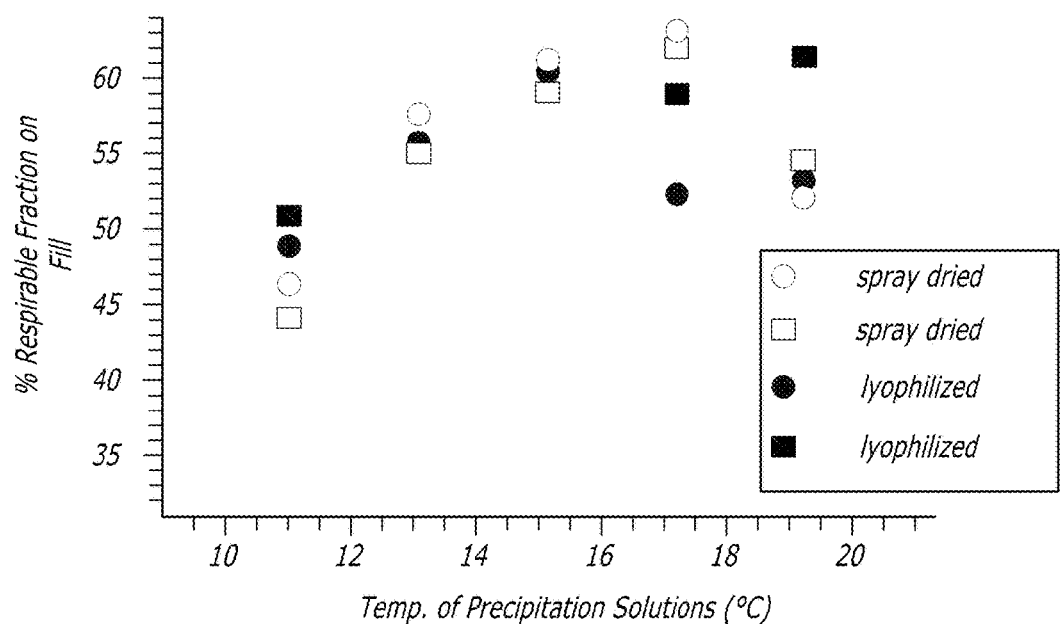
FIG. 9. Aerodynamic performance of FDKP/Insulin powders dried by spray drying or lyophilization. Two sets of suspensions (represented by squares and circles) were tested. Opened symbols represent spray-dried powders; filled symbols represent the lyophilized powders.
Figure 10A:
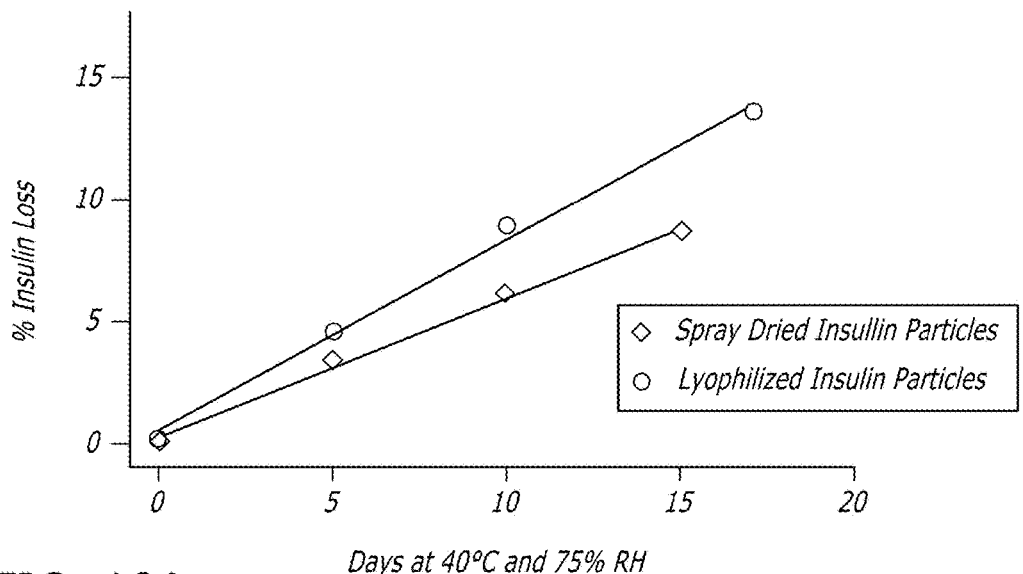
FIGS. 10A-10B. Stability data indicate that insulin loss (FIG. 10A) and A-21 formation (FIG. 10B) are reduced in the spray dried powder compared to the lyophilized powder. Both powders were adjusted to pH 4.5 prior to drying.
Figure 10B:
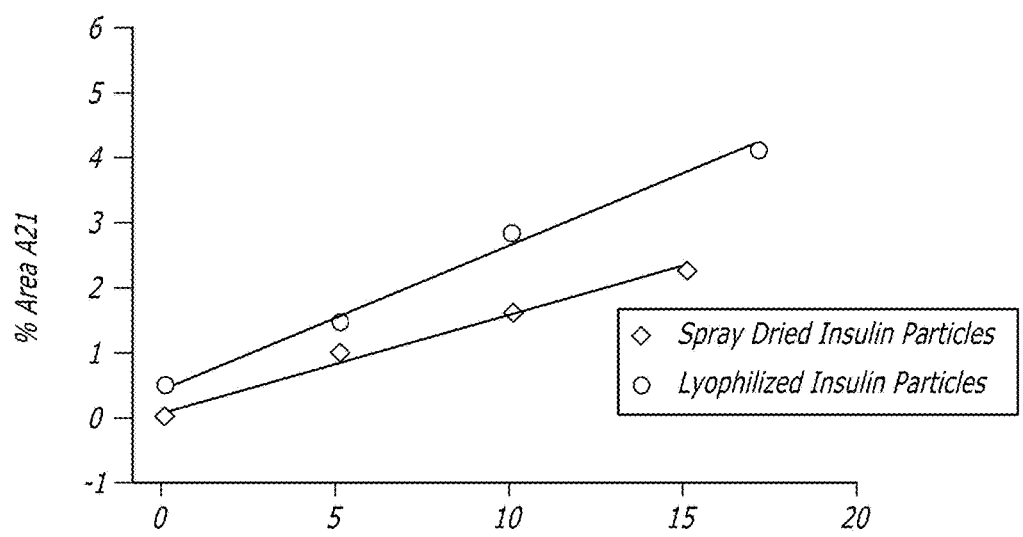

Two sets of replicates were prepared and the dry powders were characterized for aerodynamic performance (% RF/fill, cartridge emptying, mass median aerodynamic diameter [MMAD] and geometric standard deviation [GSD]). These data are summarized in Table 5. The % RF/fill for these samples is shown in FIG. 9. The stability of the powders is compared in FIGS. 10A and 10B. As noted above, the spray-dried powders showed less insulin loss and less formation of A21-desamido insulin than the lyophilized samples.

The bulk density and tapped density of the spray-dried versus the lyophilized FDKP-insulin powder were assessed. The two sets of replicates were characterized for bulk and tapped density. Table 5 shows that the spray-dried powder is more dense (by about a factor of 2) than the lyophilized powder. The bulk and tapped density for the spray-dried materials averaged 0.2 g/cc and 0.29 g/cc respectively. The bulk and tapped densities for lyophilized FDKP-insulin averaged 0.09 g/cc and 0.13 g/cc respectively. These results were unexpected and surprising. This increase in density allows more powder to be placed in a single cartridge, thereby providing for higher dosages.

TABLE 5

Effect of solution temperature on spray-dried and lyophilized FDKP-insulin particles

| Solution temperature (° C.) | Drying method | % RF/fill | % Cartridge Emptying | MMAD (μm) | GSD | Bulk Density (g/cc) | Tapped Density (g/cc) |
|---|---|---|---|---|---|---|---|
| 11 | spray-dried | 46.0 | 87.0 | 2.8 | 1.9 | 0.171 | 0.260 |
|  |  | 43.8 | 92.1 | 3.2 | 1.8 | 0.182 | 0.267 |
|  | lyophilized | 48.4 | 98.4 | 2.7 | 2.1 | 0.077 | 0.121 |
|  |  | 50.2 | 96.1 | 2.4 | 2.1 | 0.080 | 0.122 |
| 13 | spray-dried | 57.4 | 93.6 | 2.4 | 2.0 | 0.157 | 0.261 |
|  |  | 54.9 | 93.2 | 2.2 | 2.0 | 0.156 | 0.260 |
|  | lyophilized | 55.4 | 94.7 | 2.6 | 1.9 | 0.089 | 0.159 |
|  |  | 54.8 | 95.3 | 2.3 | 2.1 | 0.077 | 0.143 |
| 15 | spray-dried | 60.2 | 93.9 | 2.2 | 2.1 | 0.153 | 0.254 |
|  |  | 58.3 | 94.2 | 2.3 | 2.0 | 0.181 | 0.274 |
|  | lyophilized | NM | NM | NM | NM | 0.078 | 0.127 |
|  |  | 59.8 | 94.5 | 2.3 | 2.1 | 0.087 | 0.141 |
| 17 | spray-dried | 62.4 | 94.0 | 2.4 | 2.0 | 0.177 | 0.269 |
|  |  | 61.5 | 93.4 | 2.2 | 2.0 | 0.186 | 0.291 |
|  | lyophilized | 52.3 | 96.1 | 2.4 | 2.1 | 0.087 | 0.141 |
|  |  | 58.6 | 91.8 | 2.2 | 2.1 | 0.083 | 0.134 |
| 19 | spray-dried | 51.6 | 81.8 | 2.4 | 1.8 | 0.179 | 0.279 |
|  |  | 53.8 | 86.8 | 2.2 | 2.0 | 0.198 | 0.300 |
|  | lyophilized | 52.7 | 97.2 | 2.3 | 2.0 | 0.083 | 0.126 |
|  |  | 60.4 | 94.7 | 2.4 | 2.1 | 0.100 | 0.142 |

NM—not measured

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

It is readily apparent to one skilled in the art that various embodiments and modifications can be made to the invention disclosed herein, without departing from the scope and spirit of the invention.

Following long-standing patent law, and as used herein, the use of the word "a" or "an" when used in conjunction with the term "comprising" in the claims and/or the specification may mean "one," but it is also consistent with the meaning of "one or more," "at least one," and "one or more than one" unless specifically noted.

Recitation of ranges of values herein is merely intended to serve as a shorthand method of referring individually to each separate value falling within the range. Unless otherwise indicated herein, each individual value is incorporated into the specification as if it were individually recited herein.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Other objects, features and advantages of the present invention will become apparent from the detailed description provided herein. It should be understood, however, that the detailed description and the specific examples, while indicating specific embodiments of the invention, are given by way of illustration only, since various changes and modifications within the spirit and scope of the invention will become apparent to those skilled in the art from this detailed description.

What is claimed is:

1. A method for forming a dry powder medicament with an improved pharmaceutic property, comprising a) a step for forming microparticles comprising a diketopiperazine with acidic or basic side chains, resulting in a suspension of microparticles of the diketopiperazine with acidic or basic side chains in an appropriate solvent, and optionally a step for loading said microparticles with an active agent, then b) removing solvent by spray drying to obtain a dry powder, wherein the dry powder has an improved pharmaceutic property as compared to a dry powder obtained by removing solvent by lyophilization, and wherein the improved pharmaceutic property is increased density of the powder, and wherein said dry powder has a bulk density from 0.15 to 0.20 g/cc.

2. The method of claim 1, wherein said diketopiperazine is a diketopiperazine having the formula 3,6-di(4-X-aminobutyl)-2,5-diketopiperazine, wherein X is succinyl, glutaryl, maleyl, or fumaryl.

3. The method of claim 2, wherein X is fumaryl diketopiperazine.

4. The method of claim 1, wherein the method comprises a step for loading the microparticle with an active agent prior to the solvent removal step.

5. The method of claim 4, wherein said loading step comprises: providing a solution or a suspension of the active agent; and adding said solution or suspension of active agent to the suspension of microparticles of the diketopiperazine with acidic or basic side chains.

6. The method of claim 4, wherein the active agent is insulin, calcitonin, parathyroid hormone 1-34, bioactive fragment of parathyroid hormone, octreotide, leuprolide, RSV peptide, felbamate, cannabinoid antagonists and/or agonists, muscurinic antagon and/or agonists, heparin, low molecular weight heparin, cromolyn, sildenafil, vardenafil, tadalafil, growth hormone, AZT, DDI, GCSF, lamotrigine, chorionic gonadotropin releasing factor, luteinizing release hormone, .beta.-galactosidase, GLP-1, exendins 1-4, or ghrelin.

7. The method of claim 4, wherein the active agent is a peptide or protein.

8. The method of claim 6, wherein the active agent is insulin or an analogue thereof.

9. The method of claim 8, wherein the active agent is human insulin.

10. The method of claim 9, wherein the insulin content of the microparticle is about 3% to about 50% by weight of the dry powder formulation.

11. The method of claim 10, wherein the insulin content of the microparticle is about 7% to about 25% by weight of the dry powder formulation.

12. The method of claim 11, wherein the insulin content of the microparticle is about 11% by weight of the dry powder formulation.

13. A method for delivering an active agent to a patient in need thereof, comprising administering by inhalation to the patient an effective amount of the dry powder made by the method of claim 4.

14. The method of claim 1, wherein the step for forming microparticles comprises adjusting the pH of a solution comprising a diketopiperazine with acidic or basic side chains.

* * * * *